United States Patent
Marx et al.

(10) Patent No.: US 12,290,557 B2
(45) Date of Patent: *May 6, 2025

(54) VACCINE COMPOSITIONS FOR PORCINE EPIDEMIC DIARRHEA VIRUS AND PORCINE DELTACORONAVIRUS

(71) Applicant: Zoetis Services LLC, Parsippany, NJ (US)

(72) Inventors: Jacqueline Gayle Marx, Portage, MI (US); John Morgan Hardham, Kalamazoo, MI (US); Paul J. Dominowski, Kalamazoo, MI (US); Vicki Jon Rapp Gabrielson, Kalamazoo, MI (US); Monica Balasch Sanuy, Barcelona (ES); Marta Cabana Sumsi, Barcelona (ES); Laia Plaja Dilmé, Girona (ES); Alicia Urniza Hostench, Girona (ES); Oscar Romero Galindo, White Plains, NY (US)

(73) Assignee: Zoetis Services LLC, Parsippany, NJ (US)

( * ) Notice: Subject to any disclaimer, the term of this patent is extended or adjusted under 35 U.S.C. 154(b) by 111 days.

This patent is subject to a terminal disclaimer.

(21) Appl. No.: 17/177,724

(22) Filed: Feb. 17, 2021

(65) Prior Publication Data

US 2024/0226270 A1  Jul. 11, 2024

Related U.S. Application Data

(63) Continuation of application No. 16/282,953, filed on Feb. 22, 2019, now Pat. No. 10,953,088, which is a continuation of application No. 15/324,908, filed as application No. PCT/US2015/039475 on Jul. 8, 2015, now Pat. No. 10,251,950.

(60) Provisional application No. 62/143,412, filed on Apr. 6, 2015, provisional application No. 62/121,193, filed on Feb. 26, 2015, provisional application No. 62/115,806, filed on Feb. 13, 2015, provisional application No. 62/102,712, filed on Jan. 13, 2015, provisional application No. 62/093,657, filed on Dec. 18, 2014, provisional application No. 62/046,256, filed on Sep. 5, 2014, provisional application No. 62/037,403, filed on Aug. 14, 2014, provisional application No. 62/023,302, filed on Jul. 11, 2014.

(51) Int. Cl.
| | |
|---|---|
| *A61K 39/215* | (2006.01) |
| *A61K 39/00* | (2006.01) |
| *A61K 39/12* | (2006.01) |
| *C12N 7/00* | (2006.01) |

(52) U.S. Cl.
CPC ............ *A61K 39/215* (2013.01); *A61K 39/12* (2013.01); *C12N 7/00* (2013.01); *A61K 2039/5252* (2013.01); *A61K 2039/552* (2013.01); *A61K 2039/55505* (2013.01); *A61K 2039/55566* (2013.01); *A61K 2039/575* (2013.01); *A61K 2039/70* (2013.01); *C12N 2770/20022* (2013.01); *C12N 2770/20034* (2013.01); *C12N 2770/20063* (2013.01); *C12N 2770/20071* (2013.01)

(58) Field of Classification Search
None
See application file for complete search history.

(56) References Cited

U.S. PATENT DOCUMENTS

| | | | |
|---|---|---|---|
| 5,084,269 A | 1/1992 | Kullenberg | |
| 6,814,917 B1 * | 11/2004 | Watanabe | C04B 35/111 264/681 |
| 6,814,971 B2 | 11/2004 | Roberts et al. | |
| 10,251,950 B2 * | 4/2019 | Marx | A61K 39/215 |
| 10,953,088 B2 * | 3/2021 | Marx | A61K 39/12 |
| 11,058,763 B2 * | 7/2021 | Zhang | C07K 14/165 |
| 2002/0155128 A1 | 10/2002 | Knape et al. | |
| 2004/0258701 A1 * | 12/2004 | Dominowski | A61P 37/04 424/184.1 |
| 2015/0283229 A1 * | 10/2015 | Hernandez | A61P 43/00 435/235.1 |
| 2017/0202951 A1 | 7/2017 | Marx et al. | |
| 2019/0216919 A1 | 7/2019 | Marx | |

FOREIGN PATENT DOCUMENTS

| | | |
|---|---|---|
| CN | 104383528 | 3/2015 |
| KR | 2010-0129247 | 12/2010 |
| WO | WO 93/19779 | 10/1993 |

(Continued)

OTHER PUBLICATIONS

English translation of KR2010012947A, original document published Dec. 8, 2010.*

(Continued)

*Primary Examiner* — Shanon A. Foley

(74) *Attorney, Agent, or Firm* — Vyacheslav Vasilyev

(57) ABSTRACT

The present invention is directed to novel immunogenic compositions that protect swine from disease caused by porcine epidemic diarrhea virus (PEDV). The present invention is also directed to novel immunogenic compositions that protect swine from disease caused by porcine deltacoronavirus (PDCoV), alone or as combination vaccine to protect against PEDV. The compositions of the invention provide killed viruses whose effectiveness is enhanced by the selection of preferred adjuvants. Novel culture methods are also employed to increase reproducible yield of cultured viruses. Live vaccines are also provided from the Calaf14 PEDV isolate.

6 Claims, 31 Drawing Sheets

Specification includes a Sequence Listing.

(56) References Cited

FOREIGN PATENT DOCUMENTS

| WO | WO 2015/153425 A1 | 10/2015 |
| --- | --- | --- |
| WO | WO 2015/179412 A1 | 11/2015 |
| WO | WO 2016/022028 A1 | 2/2016 |

OTHER PUBLICATIONS

Marthaler et al. (Genome Announcements. Jul./ Aug. 2013; 1 (4): e00555-13).*

Woo et al. (Journal of Virology. 2012; 86 (7): 3995-4008).*

Pensaert, M. et al., 1978, "A New Coronavirus-Like Particle Associated With Diarrhea in Swine," Archives of Virology, vol. 58, pp. 243-247.

Chasey, D. et al., 1978, "Virus-like particles associated with porcine epidemic diarrhea," Research in Veterinary Science, vol. 25, pp. 255-256.

Wang, L. et al., 2014, "New Variant of Porcine Epidemic Diarrhea Virus, United States, 2014," Emerging Infectious Diseases, vol. 20, pp. 917-919.

Vlasova, A. et al., 2014, "Distinct Characteristics and Complex Evolution of PEDV Strains, North America, May 2013-Feb. 2014", Emerging Infectious Disease, vol. 20, pp. 1620-1628.

Park, S-J. et al., 2008, "Cloning and further sequence analysis of the ORF3 gene of wild- and attenuated-type porcine epidemic diarrhea viruses," Virus Genes, vol. 36, pp. 95-104.

Zhang, J. et al., 2014, "Reply to Classification of Emergent U.S. Strains of Porcine Epidemic Diarrhea Virus by Phylogenetic Analysis of Nucleocapsid and ORF3 Genes," Journal of Clinical Microbiology, vol. 52, pp. 3511-3514.

Song, D. S. et al., 2007, Oral efficacy of Vero cell attenuated porcine epidemic diarrhea virus DR13 strain,m Research in Veterinary Science, vol. 82, pp. 134-140.

Park, S-J. et al., 2007, "Cloning and further sequence analysis of the spike gene of attenuated porcine epidemic diarrhea virus DR13," Virus Genes, vol. 35, pp. 55-64.

Song, D. et al., 2012, "Porcine epidemic diarrhea virus: a comprehensive review of molecular epidemiology, diagnosis, and vaccines," Virus Genes, vol. 44, pp. 167-175.

Oka, T. et al., 2014, "Cell culture isolation and sequence analysis of genetically diverse US porcine epidemic diarrhea virus strains including a novel strain with a large deletion in the spike gene," Veterinary Microbiology, vol. 173, pp. 258-269.

Marthaler, D., et al., GenBank: Accession No. KF272920, Aug. 14, 2013, Porcine epidemic diarrhea virus strain USA/Colorado/2013, complete genome, National Center for Biotechnology Information (NCBI).

Collin, E. et al., 2014, "An inactivated vaccine made from a U.S. field isolate of porcine epidemic disease virus is immunogenic in pigs, Running Title: PEDV inactivated vaccine," https://www.researchgate.net/profile/Faten_Okda/publication/264934006.

PCT International Search Report and Written Opinion, International Application No. PCT/US2015/039475, International filing date Jul. 8, 2015, Date of mailing Jan. 21, 2016.

Mogler, M. A. et al., 2014, "Development of an alphavirus RNA particle-based vaccine against porcine epidemic diarrhea virus", Proceedings of the American Association of Swine Veterinarians, Annual Meeting, pp. 63-64.

Jarvis, M. C. et al., 2016, "Genomic and evolutionary inferences between American and global strains of porcine epidemic diarrhea virus", Preventive Veterinary Medicine, vol. 123, pp. 175-184.

Marthaler, D. et al., Genome Announcements, Jul./Aug. 2013; vol. 1 (4): e00555-13.

Goji, N. A. et al., 2008, "Immune Responses of Healthy Subjects to a Single Dose of Intramuscular Inactivated Influenza A/Vietnam/1203/2004 (H5N1) Vaccine after Priming with an Antigenic Variant", Journal of Infectious Diseases, vol. 198, pp. 635-641.

Nabel, G. J., 2001, "Challenges and opportunities for development of an AIDS vaccine", Nature, vol. 410, pp. 1002-1007.

Woo, P. C. Y. et al., 2012, "Discovery of Seven Novel Mammalian and Avian Coronaviruses in the Genus Deltacoronavirus Supports Bat Coronaviruses as the Gene Source of Alphacoronavirus and Betacoronavirus and Avian Coronaviruses as the Gene Source of Gammacoronavirus and Deltacoronavirus", Journal of Virology, vol. 86, pp. 3995-4008.

Gillespie et al. (Viral Immunology, 2018; 31 (1): 62-68).

Zhang et al. (Transboundary and Emerging Diseases, 2020; 67 (2): 572-583).

Tun et al. (Frontiers in Microbiology. Mar. 2016; 7 (265).

\* cited by examiner

PEDV Growth on Vero cells at High Trypsin Concentration, 4ug/ml
PEDV-infected

PEDV Growth on Vero cells at High Trypsin Concentration, 4ug/ml
PEDV-infected

PEDV Growth on Vero cells at High Trypsin Concentration, 4ug/ml
Non-infected Vero cells showing effect of high trypsin concentration
but no PEDV Infection.

FIG. 3

```
ggtggcttttctaatcatttggtcaacgtaaacaaatgaagtctttaaattacttctggttgttcttacc
agtactttcaacactcagcctaccacaagatgtcactaggtgccagtccactattaacttcaggcggttc
ttttcaaaatttaatgtgcaggcacctgctgtcgttgtgtgggtggttatctacctagtatgaactcct
ctagctggtactgtggcacaggtcttgaaactgctagtggcgtgcatggtattttcctcagttacatcga
tgctggtcagggctttgagattggcatttcacaggagccgtttgatcctagtggttaccagctttattta
cataaggccactaatggtaaccataatgctattgcacgactgcgcatttgccagtttccaaataataaaa
cattgggccctactgttaatgatgttacaacaggtcgtaactgcctattcaacaaagccattccagctta
tatgcaggatggaaaaaacatcgttgtcggcataacatgggacaatgatcgtgtcactgttttgctgac
aagatctatcattttatctcaaaaatgattggtcccgtgttgcgacaagatgttacaataaaagaagtt
gtgctatgcaatatgtttatacacctacctactacatgcttaatgttactagtgcaggtgaggatggcat
ttattatgaaccatgtacagctaattgcagtggttacgctgccaatgtgtttgccactgattctaatggc
cacataccagaaggttttagttttaataattggtttcttttgtccaatgattccactttgttgcatggta
aggtggtttccaaccaacctttgttggtcaattgtcttttggccattcctaagatttatggactaggcca
atttttctcattcaatcaaacgatggatggcgtttgtaatggagctgctgcgcagcgtgcaccagaggct
ctgaggtttaatattaatgacacctctgtcattcttgctgaaggctcaattgtacttcacactgctttag
gaacaaatctttcttttgtttgcagtaattcttcagatcctcatttagctaccttcaccatacctctggg
tgctacccaagtacctattattgttttcttaaagtggatacttacaactccactgtttataaattttg
gctgttttacctcctaccgtcagggaaattgtcatcaccaagtatggtgatgtttatgtcaatgggtttg
gatacttgcatctcggtttgttggatgctgtcacaattaatttcactggtcatggcactgacgatgatgt
ttctggttttggaccatagcatcgactaattttgttgatgcactcatcgaagttcaaggaactgccatt
cagcgtattctttattgtgatgatcctgttagccaactcaagtgttctcaggttgcttttgaccttgacg
atggttttaccctatttcttctagaaaccttctgagtcatgaacagccaatttcttttgttactctgcc
atcatttaatgatcattcttttgttaacattactgtctctgcttcctttggtggtcatagtggtgccaac
cttattgcatctgacactactatcaatgggtttagttcttttctgtgttgacactagacaatttaccattt
cactgttttataacgttacaaacagttatggttatgtgtctaaatcacaggacagtaattgccctttcac
cttgcaatctgttaatgattacctgtcttttagcaaattttgtgtttccaccaacctttggctagtgac
tgtaccatagatcttttggttaccctgagtttggtagtggtgttaagtttacgtcccttacttcaat
tcacaaagggtgagttgattactggcacgcctaaaccacttgaaggtgtcacggacgtttctttatgac
tctggatgtgtgtaccaagtatactatctatggctttaaaggtgagggtatcattacccttacaaattct
agcttttggcaggtgtttattacacatctgattctggacagttgttagcctttaagaatgtcactagtg
gtgctgtttattctgttacgccatgtcttttttcagagcaggctgcatatgttgatgatgatatagtggg
tgttatttctagtttgtctagctccacttttaacagtactagggagttgcctggtttcttctaccattct
aatgatggctctaattgtacagagcctgtgttggtgtatagtaacataggtgtttgtaaatctggcagta
ttggctacgtcccatctcagtctggccaagtcaagattgcacccacggttactgggaatatcagtattcc
caccaactttagtatgagtattaggacagaatatttacagctttacaacacgcctgttagtgttgattgt
gccacatatgtttgtaatggtaactctcgttgtaaacaattactcacccagtacactgcagcatgtaaga
ccatagagtcagcattacaactcagcgctaggcttgagtctgttgaagttaactctatgcttactatttc
tgaagaggctctacagttagctaccattagttcgtttaatggtgatggatataatttactaatgtgctg
ggtgtttctgtgtatgatcctgcaagtggcagggtggtacaaaaaggtcttttattgaagacctgctttt
ttaataaagtggttactaatggccttggtactgttgatgaagactataagcgctgttctaatggtcgctc
tgtggcagatctagtctgtgcacagtattactctggtgtcatggtactacctggtgttgttgacgctgag
aagcttcacatgtatagtgcgtctctcatcggtggtatggtgctaggaggttttacttctgcagcggcat
tgcctttagctatgctgttcaagctagactcaattatcttgctctacagacggatgttctacagcggaa
ccagcaattgcttgctgagtcttttaactctgctattggtaatataacttcagcctttgagagtgttaaa
gaggctattagtcaaacttccaaggggtttgaacactgtggctcatgcgcttactaaggttcaagaggttg
ttaactcgcagggtgcagctttgactcaacttaccgtacagctgcaacacaacttccaagccatttctag
ttctattgatgacatttactctcgactggacattctttcagccgatgttcaggttgaccgtctcatcacc
ggcagattatcagcacttaatgcttttgttgctcaaccctcactaagtatactgaggttcaggctagcag
gaagctagcacagcaaaaggttaatgagtgcgttaaatcgcaatctcagcgttatggttttgtggtggt
gatggcgagcacattttctctctggtacaggcagcacctcagggcctgctgttttacatacagtacttg
taccgggtgattttgtagatgttattgccatcgctggcttatgcgttaacgatgaaattgccttgactct
acgtgagcctggcttagtcttgtttacgcatgaacttcaaaatcatactgcgacggaatattttgtttca
tcgcgacgtatgtttgaacctagaaaaccaccgttagtgattttgttcaaattgagagttgtgtggtca
cctatgtcaatttgactagagaccaactaccagatgtaatcccagattcatcgatgttaacaaaacact
tgatgagattttagcttctctgcccaataqaactggtccaagtcttccttttagatgttttaatgccact
tatcttaatctcactggtgaaattgcagatttagagcagcgttcagagtctctccgtaatactacagagg
agctccaaagtcttatatataatatcaacaacacactagttgaccttgagtggctcaaccgagttgagac
atatatcaagtggccgtggtgggtttggttgattattttcattgttctcatctttgttgtgtcattacta
gtgttctgctgcatttccacggggttgttgtggatgctgcggctgctgctgtgcttgttttttcaggttgtt
gtaggggtcctagacttcaaccttacgaagttttgaaaaggtccacgtgcagtgatgtttcttggactt
tttcaatacacgattgacacagttgtcaaagatgtctcaaagtctgctaacttgtctttggatgctgtc
```

|  | Calaf 14 (Spanish isolate) | CV777 | ISU13-19338E-IN | OH8501 | PEDV-1CO2013 | USA-Minnesota 188-2014 |
|---|---|---|---|---|---|---|
| Calaf 14 (Spanish isolate) |  | 96 | 96 | 100 | 96 | 96 |
| CV777 |  |  | 94 | 96 | 94 | 93 |
| ISU13-19338E-IN |  |  |  | 96 | 100 | 100 |
| OH8501 |  |  |  |  | 96 | 96 |
| PEDV-1CO2013 |  |  |  |  |  | 100 |

FIG. 5

| SeqA | Name | Length | SeqB | Name | Length (nucleotides) | Score |
|---|---|---|---|---|---|---|
| 1 | Br1-87-Z25483 | 4152 | 2 | CV777-AF353511 | 4152 | 99.9 |
| 1 | Br1-87-Z25483 | 4152 | 3 | Calaf14 | 4152 | 95.71 |
| 2 | CV777-AF353511 | 4152 | 3 | Calaf14 | 4152 | 95.81 |

Scores table of complete PEDV Spike (S) gene nucleotide sequence alignment, CLUSTAL 2.1 multiple sequence alignment

FIG. 7

| SeqA | Name | Length | SeqB | Name | Length (Amino acids) | Score |
|---|---|---|---|---|---|---|
| 1 | Calaf14 | 1383 | 2 | Br1-87 | 1383 | 95.81 |
| 1 | Calaf14 | 1383 | 3 | CV777 | 1383 | 96.1 |
| 2 | Br1-87 | 1383 | 3 | CV777 | 1383 | 99.71 |

Scores table of complete PEDV Spike (S) protein alignment CLUSTAL 2.1 multiple sequence alignment

FIG. 8

```
s\protein\of\CV777_AF353511    MRSLIYFWLLLPVLPTLSLPQDVTRCQSTTNERRFFSKFNVQAPAVVVLG  50
s\protein\of\Br1-87_Z25483     MRSLIYFWLLLPVLPTLSLPQDVTRCQSTTNERRFFSKFNVQAPAVVVLG  50
s\protein\of\Calaf14           MKSLNYFWLFLPVLSTLSLPQDVTRCQSTINFRRFSKFNVQAPAVVVLG   50
                               *: ****:.********** *. ************* s\protein\of\CV777_AF353511    GYLPSMNSSSWYCGTGIETASGVHGIFLSYIDSGQGFEIGISQEPFDPSG 100
s\protein\of\Br1-87_Z25483     GYLPSMNSSSWYCGTGIETASGVHGIFLSYIDSGQGFEIGISQEPFDPSG 100
s\protein\of\Calaf14           GYLPSMNSSSWYCGTGLETASGVHGIFLSYIDAGQGFEIGISQEPFDPSG 100
                               **************:***********:************** s\protein\of\CV777_AF353511    YQLYLHKATNGNTNATARLRICQFPDNKTLGPTVNDVTTGRNCLFNKAIP 150
s\protein\of\Br1-87_Z25483     YQLYLHKATNGNTNATARLRICQFPDNKTLGPTVNDVTTGRNCLFNKAIP 150
s\protein\of\Calaf14           YQLYLHKATNGNHNAIARLRICQFPNNKTLGPTVNDVTTGRNCLFNKAIP 150
                               **********: ******:********************** s\protein\of\CV777_AF353511    AYMRDGKDIVVGITWDNDRVTVFADKIYHFYLKNDWSRVATRCYNRRSCA 200
s\protein\of\Br1-87_Z25483     AYMRDGKDIVVGITWDNDRVTVFADKIYHFYLKNDWSRVATRCYNRRSCA 200
s\protein\of\Calaf14           AYMQDGKNIVVGITWDNDRVTVFADKIYHFYLKNDWSRVATRCYNKRSCA 200
                               *:*:***********************************:* s\protein\of\CV777_AF353511    MQYVYTPTYYMLNVTSAGEDGIYYEPCTANCTGYAANVFATDSNGHIPEG 250
s\protein\of\Br1-87_Z25483     MQYVYTPTYYMLNVTSAGEDGIYYEPCTANCTGYAANVFATDSNGHIPEG 250
s\protein\of\Calaf14           MQYVYTPTYYMLNVTSAGEDGIYYEPCTANCSGYAANVFATDSNGHIPEG 250
                               *******************************:*****************
```

FIG. 9A

| | | |
|---|---|---|
| s\protein\of\CV777_AF353511 | FSFNNWFLLSNDSTLLHGKVVSNQPLLVNCLLAIPKIYGLGQFFSFNHTM | 300 |
| s\protein\of\Br1-87_225483 | FSFNNWFLLSNDSTLLHGKVVSNQPLLVNCLLAIPKIYGLGQFFSFNHTM | 300 |
| s\protein\of\Calaf14 | FSFNNWFLLSNDSTLLHGKVVSNQPLLVNCLLAIPKIYGLGQFFSFNQTM | 300 |
| | ************************************* :** | |
| s\protein\of\CV777_AF353511 | DGVCNGAAVDRAPEALRFNINDTSVILAEGSIVLHTALGTNLSFVCSNSS | 350 |
| s\protein\of\Br1-87_225483 | DGVCNGAAVDRAPEALRFNINDTSVILAEGSIVLHTALGTNLSFVCSNSS | 350 |
| s\protein\of\Calaf14 | DGVCNGAAAQRAPEALRFNINDTSVILAEGSIVLHTALGTNLSFVCSNSS | 350 |
| | ********  .:************************************* | |
| s\protein\of\CV777_AF353511 | DPHLAIFAIPLGATEVPYYCFLKVDTYNSTVYKFLAVLPPTVREIVITKY | 400 |
| s\protein\of\Br1-87_225483 | DPHLAIFAIPLGATEVPYYCFLKVDTYNSTVYKFLAVLPSTVREIVITKY | 400 |
| s\protein\of\Calaf14 | DPHLATFTIPLGATQVPYYCFLKVDTYNSTVYKFLAVLPPTVREIVITKY | 400 |
| | **  .**:*****************.*********** | |
| s\protein\of\CV777_AF353511 | GDVYVNGFGYLHLGLLDAVTINFTGHGTDDDVSGFWTIASTNFVDALIEV | 450 |
| s\protein\of\Br1-87_225483 | GDVYVNGFGYLHLGLLDAVTIYFTGHGTDDDVSGFWTIASTNFVDALIEV | 450 |
| s\protein\of\Calaf14 | GDVYVNGFGYLHLGLLDAVTINFTGHGTDDDVSGFWTIASTNFVDALIEV | 450 |
| | ********************* *************************** | |
| s\protein\of\CV777_AF353511 | QGTSIQRILYCDDPVSQLKCSQVAEDLDDGFYPISSRNLLSHEQPISFVT | 500 |
| s\protein\of\Br1-87_225483 | QGTSIQRILYCDDPVSQLKCSQVAEDLDDGFYPISSRNLLSHEQPISFVT | 500 |
| s\protein\of\Calaf14 | QGTAIQRILYCDDPVSQLKCSQVAEDLDDGFYPISSRNLLSHEQPISFVT | 500 |
| | *:******************************************* | |
| s\protein\of\CV777_AF353511 | LPSFNDHSFVNITVSAAFGGLSSANLVASDTTINGFSSECVDTRQFTITL | 550 |
| s\protein\of\Br1-87_225483 | LPSFNDHSFVNITVSAAFGGLSSANLVASDTTINGFSSECVDTRQFTITL | 550 |
| s\protein\of\Calaf14 | LPSFNDHSFVNITVSASFGGHSGANLIASDTTINGFSSECVDTRQFTISL | 550 |
| | **************:*:*.*:******************:* | |

FIG. 9 B

| | | |
|---|---|---|
| s\protein\of\CV777_AF353511 | FYNVTNSYGYVSKSQDSNCPFTLQSVNDYLSFSKFCVSTSLLAGACTIDL | 600 |
| s\protein\of\Br1-87_Z25483 | FYNVTNSYGYVSKSQDSNCPFTLQSVNDYLSFSKFCVSTSLLAGACTIDL | 600 |
| s\protein\of\Calaf14 | FYNVTNSYGYVSKSQDSNCPFTLQSVNDYLSFSKFCVSTNLLASDCTIDL | 600 |
| | ****************************.*.*.****** | |
| s\protein\of\CV777_AF353511 | EGYPAFGSGVKLTSLYFQFTKGELITGTPKPLEGITDVSEMTLDVCTKYT | 650 |
| s\protein\of\Br1-87_Z25483 | EGYPAFGSGVKLTSLYFQFTKGELITGTPKPLEGITDVSEMTLDVCTKYT | 650 |
| s\protein\of\Calaf14 | EGYPEFGSGVKFTSLYFQFTKGELITGTPKPLEGVTDVSEMTLDVCTKYT | 650 |
| | **:**:*******************:*********** | |
| s\protein\of\CV777_AF353511 | IYGFKGEGIITLTNSSILAGVYYTSDSGQLLAFKNVTSGAVYSVTPCSFS | 700 |
| s\protein\of\Br1-87_Z25483 | IYGFKGEGIITLTNSSILAGVYYTSDSGQLLAFKNVTSGAVYSVTPCSFS | 700 |
| s\protein\of\Calaf14 | IYGFKGEGIITLTNSSFLAGVYYTSDSGQLLAFKNVTSGAVYSVTPCSFS | 700 |
| | **************:****************************** | |
| s\protein\of\CV777_AF353511 | EQAAYVNDDIVGVISSLSNSTFNNTRELPGFFYHSNDGSNCTEPVLVYSN | 750 |
| s\protein\of\Br1-87_Z25483 | EQAAYVNDDIVGVISSLSNSTFNNTRELPGFFYHSNDGSNCTEPVLVYSN | 750 |
| s\protein\of\Calaf14 | EQAAYVDDDIVGVISSLSSSTFNSTRELPGFFYHSNDGSNCTEPVLVYSN | 750 |
| | ****:*******.:*.************************* | |
| s\protein\of\CV777_AF353511 | IGVCKSGSIGYVPSQYGQVKIAPTVTGNISIPTNFSMSIRTEYLQLYNTP | 800 |
| s\protein\of\Br1-87_Z25483 | IGVCKSGSIGYVPSQYGQVKIAPTVTGNISIPTNFSMSIRTEYLQLYNTP | 800 |
| s\protein\of\Calaf14 | IGVCKSGSIGYVPSQYGQVKIAPTVTGNISIPTNFSMSIRTEYLQLYNTP | 800 |
| | ************************************************* | |
| s\protein\of\CV777_AF353511 | VSVDCATYVCNGNSRCKQLLTQYTAACKTIESALQLSARLESVEVNSMLT | 850 |
| s\protein\of\Br1-87_Z25483 | VSVDCATYVCNGNSRCKQLLTQYTAACKTIESALQLSARLESVEVNSMLT | 850 |
| s\protein\of\Calaf14 | VSVDCATYVCNGNSRCKQLLTQYTAACKTIESALQLSARLESVEVNSMLT | 850 |
| | ************************************************* | |

FIG. 9C

```
S\protein\of\CV777_AF353511     ISEEALQLATISSFNGDGYNFTNVLGASVYDPASGRVVQKRSVIEDLLFN 900
S\protein\of\Br1-87_Z25483      ISEEALQLATISSFNGDGYNFTNVLGASVYDPASGRVVQKRSVIEDLLFN 900
S\protein\of\\Calaf14           ISEEALQLATISSFNGDGYNFTNVLGVSVYDPASGRVVQKRSFIEDLLFN 900
                                **************************.***************.*******

S\protein\of\CV777_AF353511     KVVTNGLGTVDEDYKRCSNGRSVADLVCAQYYSGVMVLPGVVDAEKLHMY 950
S\protein\of\Br1-87_Z25483      KVVTNGLGTVDEDYKRCSNGRSVADLVCAQYYSGVMVLPGVVDAEKLHMY 950
S\protein\of\\Calaf14           KVVTNGLGTVDEDYKRCSNGRSVADLVCAQYYSGVMVLPGVVDAEKLHMY 950
                                **************************************************

S\protein\of\CV777_AF353511     SASLIGGMALGGITAAAALPFSYAVQARLNYLALQTDVLQRNQQLLAESF 1000
S\protein\of\Br1-87_Z25483      SASLIGGMALGGITAAAALPFSYAVQARLNYLALQTDVLQRNQQLLAESF 1000
S\protein\of\\Calaf14           SASLIGGMVLGGFTSAAALPFSYAVQARLNYLALQTDVLQRNQQLLAESF 1000
                                ********.***:*:***********************************

S\protein\of\CV777_AF353511     NSAIGNITSAFESVKEAISQTSKGLNTVAHALTKVQEVVNSQGSALNQLT 1050
S\protein\of\Br1-87_Z25483      NSAIGNITSAFESVKEAISQTSKGLNTVAHALTKVQEVVNSQGSALNQLT 1050
S\protein\of\\Calaf14           NSAIGNITSAFESVKEAISQTSKGLNTVAHALTKVQEVVNSQGAALTQLT 1050
                                *******************************************:**.***

S\protein\of\CV777_AF353511     VQLQHNFQAISSSIDDIYSRLDILSADVQVDRLITGRLSALNAFVAQTLT 1100
S\protein\of\Br1-87_Z25483      VQLQHNFQAISSSIDDIYSRLDILLADVQVDRLITGRLSALNAFVAQTLT 1100
S\protein\of\\Calaf14           VQLQHNFQAISSSIDDIYSRLDILSADVQVDRLITGRLSALNAFVAQTLT 1100
                                ************************ *************************

S\protein\of\CV777_AF353511     KYTEVQASRKLAQQKVNECVKSQSQRYGFCGGDGEHIFSLVQAAPQGLLF 1150
S\protein\of\Br1-87_Z25483      KYTEVQASRKLAQQKVNECVKSQSQRYGFCGGDGEHIFSLVQAAPQGLLF 1150
S\protein\of\\Calaf14           KYTEVQASRKLAQQKVNECVKSQSQRYGFCGGDGEHIFSLVQAAPQGLLF 1150
                                **************************************************
```

FIG. 9 D

```
s\protein\of\CV777_AF353511    LHTVLVPGDFVNVLAIAGLCVNGEIALTLREPGLVLFTHELQTYTATEYF 1200
s\protein\of\Br1-87_Z25483     LHTVLVPGDFVNVLAIAGLCVNGEIALTLREPGLVLFTHELQTYTATEYF 1200
s\protein\of\Calaf14           LHTVLVPGDFVDVIAIAGLCVNDEIALTLREPGLVLFTHELQNHTATEYF 1200
                               ***********:*:*************************:.***** s\protein\of\CV777_AF353511    VSSRRMFEPRKPTVSDFVQIESCVVTYVNLTSDQLPDVIPDYIDVNKTLD 1250
s\protein\of\Br1-87_Z25483     VSSRRMFEPRKPTVSDFVQIESCVVTYVNLTSDQLPDVIPDYIDVNKTLD 1250
s\protein\of\Calaf14           VSSRRMFEPRKPTVSDFVQIESCVVTYVNLTRDQLPDVIPDYIDVNKTLD 1250
                               *****************************.*************** s\protein\of\CV777_AF353511    EILASLPNRTGPSLPLDVFNATYLNLTGEIADLEQRSESLRNTTEELRSL 1300
s\protein\of\Br1-87_Z25483     EILASLPNRTGPSLPLDVFNATYLNLTGEIADLEQRSESLRNTTEELRSL 1300
s\protein\of\Calaf14           EILASLPNRTGPSLPLDVFNATYLNLTGEIADLEQRSESLRNTTEELQSL 1300
                               ***********************************************:**

s\protein\of\CV777_AF353511    INNINNTLVDLEWLNRVETYIKWPWWVWLIIVLIFVVSLLVFCCISTG 1350
s\protein\of\Br1-87_Z25483     INNINNTLVDLEWLNRVETYIKWPWWVWLIIVLIFVVSLLVFCCISTG 1350
s\protein\of\Calaf14           IYNINNTLVDLEWLNRVETYIKWPWWVWLIIFIVLIFVVSLLVFCCISTG 1350
                               * ***************************:*:************ s\protein\of\CV777_AF353511    CCGCCGCCGACFSGCCRGPRLQPYEAFEKVHVQ 1383
s\protein\of\Br1-87_Z25483     CCGCCGCCGACFSGCCRGPRLQPYEAFEKVHVQ 1383
s\protein\of\Calaf14           CCGCCGCCCACFSGCCRGPRLQPYEVFEKVHVQ 1383
                               ********.****************:*******
```

Complete spike protein amino acid sequences, strain CV777 (SEQ ID NO:6), strain Br1-87 (SEQ ID NO:5), and strain Calaf14 (SEQ ID NO:4)

FIG. 9 E

```
CV777-AF353511    ATGAGGTCTCTTAATTTACTTCTGGTTGCTCTCTTACCAGTACTTCCAACACTCAGCCTACCA   60
Br1/87-Z25483     ATGAGGTCTCTTAATTTACTTCTGGTTGCTCTCTTACCAGTACTTCCAACACTCAGCCTACCA   60
Calaf14-Spanish   ATGAAGTCTCTTAAATTACTTCTGGTTGTCTCTTACCAGTACTTCAACACTCAGCCTACCA    60
                  ****.*********.************.*******************************

CV777-AF353511    CAAGATGTCACTAGGTGCCAGTCTACTACTACTTTAGGCGGTTCTTTTCAAAATTTAAT      120
Br1/87-Z25483     CAAGATGTCACTAGGTGCCAGTCTACTACTACTTTAGGCGGTTCTTTTCAAAATTTAAT      120
Calaf14-Spanish   CAAGATGTCACTAGGTGCCAGTCCACTATTAACTTCAGGCGGTTCTTTTCAAAATTTAAT    120
                  ***********************.*****:.***.**:*********************

CV777-AF353511    GTTCAGGCCACCTGCCGTCGTCGTTTGGGTGGTTACCTAGTATGAACTCTTCTAGC        180
Br1/87-Z25483     GTTCAGGCCACCTGCCGTCGTCGTTTGGGTGGTTACCTAGTATGAACTCTTCTAGC        180
Calaf14-Spanish   GTGCAGGCCACCTGCCGTCGTGTTTGTGTGGTTATCTACCTAGTATGAACTCCCTCTAGC   180
                  ** *********************:*****    ** ** ***********  ******

CV777-AF353511    TGGTACTGTGGCACAGGCATTGAAACTGCTAGTGGCGTTCATGGTATTTTTCTCAGCTAC   240
Br1/87-Z25483     TGGTACTGTGGCACAGGCATTGAAACTGCTAGTGGCGTTCATGGTATTTTTCTCAGCTAC   240
Calaf14-Spanish   TGGTACTGTGGCACAGGTCTTGAAACTGCTAGTGGCGTGCATGGTATTTCCCTCAGTTAC   240
                  *****************  ****************** ********** ***** ***
```

FIG. 10 A

```
CV777-AF353511      ATCGATTCTGGTCAGGGCTTTGAGATTGGCATTTCGCAAGAGCCGTTTGATCCTAGTGGT 300
Br1/87-Z25483       ATCGATTCTGGTCAGGGCTTTGAGATTGGCATTTCGCAAGAGCCGTTTGATCCTAGTGGT 300
Calaf14-Spanish     ATCGATGCTGGTCAGGGCTTTGAGATTGGCATTTCACAGGAGCCGTTTGATCCTAGTGGT 300
                    ****** ****************************.**.*********************

CV777-AF353511      TACCAGCTTTATTTACATAAGGCCACTAATGGTAACACTAATGCTATTGCACGACTGCGC 360
Br1/87-Z25483       TACCAGCTTTATTTACATAAGGCCACTAATGGTAACACTAATGCTACTGCACGACTGCGC 360
Calaf14-Spanish     TACCAGCTTTATTTACATAAGGCCACTAATGGTAACCATAATGCTATTGCACGACTGCGC 360
                    ***********************************..********* *************

CV777-AF353511      ATTTGCCAGTTTCCCGATAATAAAACATTGGGCCCTACTGTTAATGATGTTACAACAGGT 420
Br1/87-Z25483       ATTTGCCAGTTTCCCGATAATAAAACATTGGGCCCTACTGTTAATGATGTTACAACAGGT 420
Calaf14-Spanish     ATTTGCCAGTTTCCAAATAATAAAACATTGGGCCCTACTGTTAATGATGTTACAACAGGT 420
                    **************..********************************************

CV777-AF353511      CGTAACTGCCTATTCAACAAAGCCATTCCAGCTTATATGCGTGATGGAAAAGATATTGTT 480
Br1/87-Z25483       CGTAACTGCCTATTCAACAAAGCCATTCCAGCTTATATGCGTGATGGAAAAGATATTGTT 480
Calaf14-Spanish     CGTAACTGCCTATTCAACAAAGCCATTCCAGCTTATATGCAGGATGGAAAAAACATCGTT 480
                    ****************************************. *********.* ** ***
```

FIG. 10 B

```
CV777-AF353511      GTCGGCATAACATGGGATAATGATCGTGTCACTGTTTTTGCTGACAAGATCTATCATTTT 540
Br1/87-Z25483       GTCGGCATAACATGGGATAATGATCGTGTCACTGTTTTTGCTGACAAGATCTATCATTTT 540
Calaf14-Spanish     GTCGGCATAACATGGGACAATGATCGTGTCACTGTTTTTGCTGACAAGATCTATCATTTT 540
                    **************** *******************************************

CV777-AF353511      TATCTTAAAAATGATTGGTCCCGCGTTGCGACAAGATGTTACAATCGCAGAAGTTGTGCT 600
Br1/87-Z25483       TATCTTAAAAATGATTGGTCCCGCGTTGCGACAAGATGTTACAATCGCAGAAGTTGTGCT 600
Calaf14-Spanish     TATCTCAAAAATGATTGGTCCCGTGTTGCGACAAGATGTTACAATAAAAGAAGTTGTGCT 600
                    ***** ***************** *********************...************

CV777-AF353511      ATGCAATATGTTTATACACCTACCTACTACATGCTTAATGTTACTAGTGCAGGTGAGGAT 660
Br1/87-Z25483       ATGCAATATGTTTATACACCTACCTACTACATGCTTAATGTTACTAGTGCAGGTGAGGAT 660
Calaf14-Spanish     ATGCAATATGTTTATACACCTACCTACTACATGCTTAATGTTACTAGTGCAGGTGAGGAT 660
                    ************************************************************

CV777-AF353511      GGCATTTATTATGAACCCTGTACAGCTAATTGCACTGGTTACGCTGCCAATGTATTTGCC 720
Br1/87-Z25483       GGCATTTATTATGAACCCTGTACAGCTAATTGCACTGGTTACGCTGCCAATGTATTTGCC 720
Calaf14-Spanish     GGCATTTATTATGAACCATGTACAGCTAATTGCAGTGGTTACGCTGCCAATGTGTTTGCC 720
                    *****************.**************** ******************.******
```

FIG. 10 C

```
CV777-AF353511    ACTGATTCCAATGGCCATATACCAGAGAAGGTTTTAGTTTTAATAATTGGTTTCTTTTATCC  780
Br1/87-Z25483     ACTGATTCCAATGGCCATATACCAGAGAAGGTTTTAGTTTTAATAATTGGTTTCTTTTATCC  780
Calaf14-Spanish   ACTGATTCTAATGGCCACATACCAGAGAAGGTTTTAGTTTTAATAATTGGTTTCTTTTGTCC  780
                  ******** ******** ***************************************.***

CV777-AF353511    AATGACTCCACTTTGTTGCATGGTAAAGTGGTTTCCAACCAACCCTTGTTGGTCAATTGT    840
Br1/87-Z25483     AATGACTCCACTTTGTTGCATGGTAAAGTGGTTTCCAACCAACCCTTGTTGGTCAATTGT    840
Calaf14-Spanish   AATGATTCCACTTTGTTGCATGGTAAGGTGGTTTCCAACCAACCTTTGTTGGTCAATTGT    840
                  ***** ******************** ***************** ***************

CV777-AF353511    CTTTTGGCCATTCCTAAGATTTATGGACTAGGCCAATTTTTCTCATTCAATCACACGATG    900
Br1/87-Z25483     CTTTTGGCCATTCCTAAGATTTATGGACTAGGCCAATTTTTCTCATTCAATCACACGATG    900
Calaf14-Spanish   CTTTTGGCCATTCCTAAGATTTATGGACTAGGCCAATTTTTCTCATTCAATCAAACGATG    900
                  *****************************************************.*****

CV777-AF353511    GATGGCGTTTGTAATGGAGCTGCTGTGCCCCAGAGAGGCTCTGAGGTTTAATATT         960
Br1/87-Z25483     GATGGCGTTTGTAATGGAGCTGCTGTGCCCCAGAGAGGCTCTGAGGTTTAATATT         960
Calaf14-Spanish   GATGGCGTTTGTAATGGAGCTGCGCAGCGTGCACCAGAGAGGCTCTGAGGTTTAATATT    960
                  *********************** *  *   **  ************************
```

FIG. 10 D

```
CV777-AF353511    AATGACACCTCCGTCATTCTTGCTGAAGGCTCAATTGTACTTCATACTGCTTTAGGAACA  1020
Br1/87-Z25483     AATGACACCTCCGTCATTCTTGCTGAAGGCTCAATTGTACTTCATACTGCTTTAGGAACA  1020
Calaf14-Spanish   AATGACACCTCTGTCATTCTTGCTGAAGGCTCAATTGTACTTCACACTGCTTTAGGAACA  1020
                  *********** ******************************** **************

CV777-AF353511    AATCTTTCTTTTGTTTGCAGTAATTCCTCAGATCCTCATTTAGCCATCCTCTTTGCCATACCT  1080
Br1/87-Z25483     AATCTTTCTTTTGTTTGCAGTAATTCCTCAGATCCTCATTTAGCCATCCTCTTTGCCATACCT  1080
Calaf14-Spanish   AATCTTTCTTTTGTTTGCAGTAATTCTTCAGATCCTCATTTAGTACCCTCACCATACCT  1080
                  ************************** *************** *  *** *********

CV777-AF353511    CTGGGTGCTACTGAAGTACCCTACTATTGCTTTCTTAAAGTGGATACTTACAACTCCACT  1140
Br1/87-Z25483     CTGGGTGCTACTGAAGTACCCTACTATTGCTTTCTTAAAGTGGATACTTACAACTCCACT  1140
Calaf14-Spanish   CTGGGTGCTACCCAAGTACCCTATTATTGTTTTCTTAAAGTGGATACTTACAACTCCACT  1140
                  ***********  ********** ***** **** ****************

CV777-AF353511    GTTTATAAATTCTTGGCTGTTTTTACCTCCTACTGTCAGGGAAATTGTCATCACCAAGTAT  1200
Br1/87-Z25483     GTTTATAAATTCTTGGCTGTTTTTACCTTCTACTGTCAGGGAAATTGTCATCACCAAGTAT  1200
Calaf14-Spanish   GTTTATAAATTTTTGGCTGTTTTTACCTCCTACCGTCAGGGAAATTGTCATCACCAAGTAT  1200
                  *********** **************** **** **************************
```

FIG. 10 E

| | | |
|---|---|---|
| CV777-AF353511 | GGTGATGTTTATGTCAATGGGTTTGGCTATTTGCATCTCGGTTTGTTGTGGATGCTGTCACA | 1260 |
| Br1/87-Z25483 | GGTGATGTTTATGTCAATGGGTTTGGCTATTTGCATCTCGGTTTGTTGTGGATGCTGTCACA | 1260 |
| Calaf14-Spanish | GGTGATGTTTATGTCAATGGGTTTGGATACTTGCATCTCGGTTTGTTGTGGATGCTGTCACA | 1260 |
| | ·· ************************************************** | |
| CV777-AF353511 | ATTAATTTCACTGGTCATGGCACTGACGATGACGTTTCAGGTTTCTGGACCATAGCATCG | 1320 |
| Br1/87-Z25483 | ATTTATTTCACTGGTCATGGCACTGACGATGACGTTTCAGGTTTCTGGACCATAGCATCG | 1320 |
| Calaf14-Spanish | ATTAATTTCACTGGTCATGGCACTGACGATGATGTTTCTGGTTTTTGGACCATAGCATCG | 1320 |
| | *** *********************** ******* * ** ******************** | |
| CV777-AF353511 | ACTAATTTTGTTGATGCACTCATCGAGGTTCAAGGAACTTCCATTCAGCGTATTCTTTAT | 1380 |
| Br1/87-Z25483 | ACTAAATTTGTTGATGCACTCATCGAGGTTCAAGGAACTTCCATTCAGCGTATTCTTTAT | 1380 |
| Calaf14-Spanish | ACTAAATTTGTTGATGCACTCATCGAAGTTCAAGGAACTGCCATTCAGCGTATTCTTTAT | 1380 |
| | ***** ******************* ************ ****************** | |
| CV777-AF353511 | TGTGATGATCCTGTTAGCCAACTCAAGTGTTCTCAGGTTGCTTTTGACCTTGACGATGGT | 1440 |
| Br1/87-Z25483 | TGTGATGATCCTGTTAGCCAACTCAAGTGTTCTCAGGTTGCTTTTGACCTTGACGATGGT | 1440 |
| Calaf14-Spanish | TGTGATGATCCTGTTAGCCAACTCAAGTGTTCTCAGGTTGCTTTTGACCTTGACGATGGT | 1440 |
| | ************************************************************ | |

FIG. 10 F

| | | |
|---|---|---|
| CV777-AF353511 | TTTTACCCCATCTCTTCTAGAAACCTTCTGAGTCACGAACAGCCAATTTCTTTTGTTACT | 1500 |
| Br1/87-Z25483 | TTTTACCCCATCTCTTCTAGAAACCTTCTGAGTCACGAACAGCCAATTTCTTTTGTTACT | 1500 |
| Calaf14-Spanish | TTTTACCCTATTCTTCTAGAAACCTTCTGAGTCATGAACAGCCAATTTCTTTTGTTACT | 1500 |
| | ******** ** ************************ ******************** | |
| CV777-AF353511 | TTGCCATCATTTAATGATCATTCTTTTGTTAATATTACTGTCTCTGCGGGCTTTTGGTGGT | 1560 |
| Br1/87-Z25483 | TTGCCATCATTTAATGATCATTCTTTTGTTAATATTACTGTCTCTGCGGGCTTTTGGTGGT | 1560 |
| Calaf14-Spanish | CTGCCATCATTTAATGATCATTCTTTTGTTAACATTACTGTCTCTGCTTCCTTGGTGGT | 1560 |
| | ********************************** ************ * ********* | |
| CV777-AF353511 | CTTAGTAGTGCCAATCTCGTTGCATCTGACACTACTATCAATGGGTTTAGTTCTTTCTGT | 1620 |
| Br1/87-Z25483 | CTTAGTAGTGCCAATCTCGTTGCATCTGACACTACTATCAATGGGTTTAGTTCTTTCTGT | 1620 |
| Calaf14-Spanish | CATAGTGGTGCCAACCTTATTGCACTTATTGCATCTGACACTACTATCAATGGGTTAGTTCTTTCTGT | 1620 |
| | * ***** ******* ** ** * ********* ** | |
| CV777-AF353511 | GTTGACACTAGACAATTACCATTACACTGTTTTATAATGTTACAAAACAGTTATGGTTAT | 1680 |
| Br1/87-Z25483 | GTTGACACTAGACAATTACCATTACACTGTTTTATAATGTTACAAACAGTTATGGTTAT | 1680 |
| Calaf14-Spanish | GTTGACACTAGACAATTACCATTTCACTGTTTTTATAACGTTACAAACAGTTATGGTTAT | 1680 |
| | *********************** ******* **** ******** *********** | |

FIG. 10 G

| | | |
|---|---|---|
| CV777-AF353511 | GTGTCTAAATCACAGGATAGTAATTGTCCTTTCACCCTTGCAATCTGTTAATGATTACCTG | 1740 |
| Br1/87-Z25483 | GTGTCTAAATCACAGGATAGTAATTGTCCTTTCACCCTTGCAATCTGTTAATGATTACCTG | 1740 |
| Calaf14-Spanish | GTGTCTAAATCACAGGACAGTAATTGCCCCTTTCACCCTTGCAATCTGTTAATGATTACCTG | 1740 |
| | ***************** ********** ************************** | |
| | | |
| CV777-AF353511 | TCTTTTAGCAAATTTTGTGTTTCAACCAGCCCTTTTGGCTGGTGCTTGTACCATAGATCTT | 1800 |
| Br1/87-Z25483 | TCTTTTAGCAAATTTTGTGTTTCAACCAGCCCTTTTGGCTGGTGCTTGTACCATAGATCTT | 1800 |
| Calaf14-Spanish | TCTTTTAGCAAATTTTGTGTTTCCACCAACCTTTTGGCTAGTGACTGTACCATAGATCTT | 1800 |
| | ********************* * ****, ,************ | |
| | | |
| CV777-AF353511 | TTTGGTTACCCTGCGTTCGGTAGTGGTGTTAAGTTGACGTCCCTTTAATTTCAATTCACA | 1860 |
| Br1/87-Z25483 | TTTGGTTACCCTGCGTTCGGTAGTGGTGTTAAGTTGACGTCCCTTTATTTTCAATTCACA | 1860 |
| Calaf14-Spanish | TTTGGTTACCCTGAGTTTGGTAGTGGTGTTAAGTTTACGTCCCCTTTACTTTACTTCACA | 1860 |
| | ************* *** ************** ****** **** *** ********* | |
| | | |
| CV777-AF353511 | AAAGGTGAGTTGATTACTGGCACGCCTAAACCACTTGAAGGTATCACAGACGTTTCTTTT | 1920 |
| Br1/87-Z25483 | AAAGGTGAGTTGATTACTGGCACGCCTAAACCACTTGAAGGTATCACAGACGTTTCTTTT | 1920 |
| Calaf14-Spanish | AAGGGTGAGTTGATTACTGGCACGCCTAAAACCACTTGAAGGTGTCACGGACGTTTCTTTT | 1920 |
| | ** ,***************************** ********** **** ********** | |

FIG. 10 H

```
CV777-AF353511    ATGACTCTGGATGTGTGTACCAAGTATACTATCTATGGCTTTAAAGGTGAGGGTATTATT 1980
Br1/87-Z25483     ATGACTCTGGATGTGTGTACCAAGTATACTATCTATGGCTTTAAAGGTGAGGGTATTATT 1980
Calaf14-Spanish   ATGACTCTGGATGTGTGTACCAAGTATACTATCTATGGCTTTAAAGGTGAGGGTATCATT 1980
                  ******************************************************* ***

CV777-AF353511    ACCCTTACAAATTCTAGCATTTTGGCAGGTGTGTTTATTATACATCTGATTCTGGACAGTTG 2040
Br1/87-Z25483     ACCCTTACAAATTCTAGCATTTTGGCAGGTGTGTTTATTATACATCTGATTCTGGACAGTTG 2040
Calaf14-Spanish   ACCCTTACAAATTCTAGCTTTTTGGCAGGTGTGTTTATTACACATCTGATTCTGGACAGTTG 2040
                  ******************  ******************* *******************

CV777-AF353511    TTAGCCTTTAAGAATGTCACTAGTGGTGCTGTTTATTCGTCACGCCATGTTCTTTTTCA 2100
Br1/87-Z25483     TTAGCCTTTAAGAATGTCACTAGTGGTGCTGTTTATTCGTCACGCCATGTTCTTTTTCA 2100
Calaf14-Spanish   TTAGCCTTTAAGAATGTCACTAGTGGTGCTGTTTATTCGTTACGCCATGTTCTTTTTCA 2100
                  **************************************** ******************

CV777-AF353511    GAGCAGGCTGCATATGTTAATGATGATATAGTGGGTGTTATTCTAGTTGTCTAACTCC 2160
Br1/87-Z25483     GAGCAGGCTGCATATGTTAATGATGATATAGTGGGTGTTATTCTAGTTGTCTAACTCC 2160
Calaf14-Spanish   GAGCAGGCTGCATATGTTGATGATGATATAGTGGGTGTTATTCTAGTTGTCTAGCTCC 2160
                  ******************.*********************************. ****
```

FIG. 10 I

```
CV777-AF353511    ACTTTTAACAATACTAGGGAGTTGCCTGGTTTCTTCTACCATTCTAATGACGGCTCCAAT  2220
Br1/87-Z25483     ACTTTTAACAATACTAGGGAGTTGCCTGGTTTCTTCTACCATTCTAATGACGGCTCCAAT  2220
Calafl4-Spanish   ACTTTTAACAGTACTAGGGAGTTGCCTGGTTTCTTCTACCATTCTAATGATGGCTCTAAT  2220
                  *********  ************************************** *****  ***

CV777-AF353511    TGTACAGAGCCTGTGTTGGTGTATAGTAACATAGGTGTTTGTAAATCTGGCAGTATTGGC  2280
Br1/87-Z25483     TGTACAGAGCCTGTGTTGGTGTATAGTAACATAGGTGTTTGTAAATCTGGCAGTATTGGC  2280
Calafl4-Spanish   TGTACAGAGCCTGTGTTGGTGTATAGTAACATAGGTGTTTGTAAATCTGGCAGTATTGGC  2280
                  ************************************************************

CV777-AF353511    TATGTTCCATCTCAGTATGGCCAAGTCAAGATTGCACCCACGGTTACTGGGAATATTAGT  2340
Br1/87-Z25483     TATGTTCCATCTCAGTATGGCCAAGTCAAGATTGCACCCACGGTTACTGGGAATATTAGT  2340
Calafl4-Spanish   TACGTCCCATCTCAGTCTCGGCCAAGTCAAGATTGCACCCACGGTTACTGGGAATATCAGT  2340
                  ** ** **********  * ************************************ ***

CV777-AF353511    ATTCCCACCAACTTTAGTATGAGTATTAGAACAGAATATTTACAGCTTTACAACACGCCT  2400
Br1/87-Z25483     ATTCCCACCAACTTTAGTATGAGTATTAGAACAGAATATTTACAGCTTTACAACACGCCT  2400
Calafl4-Spanish   ATTCCCACCAACTTTAGTATGAGTATTAGGACAGAATATTTACAGCTTTACAACACGCCT  2400
                  *****************************  *****************************
```

FIG. 10 J

```
CV777-AF353511    GTTAGTGTTGATTGTGCTACATATGTTTGTAATGGTAACTCTCGTTGTAAACAATTACTC  2460
Br1/87-Z25483     GTTAGTGTTGATTGTGCTACATATGTTTGTAATGGTAACTCTCGTTGTAAACAATTACTC  2460
Calafl4-Spanish   GTTAGTGTTGATTGTGCCACATATGTTTGTAATGGTAACTCTCGTTGTAAACAATTACTC  2460
                  ***************** ******************************************

CV777-AF353511    ACCCAGTACACTGCAGCATGTAAGACCATAGAGTCAGCATTACAACTCAGCGCTAGGCTT  2520
Br1/87-Z25483     ACCCAGTACACTGCAGCATGTAAGACCATAGAGTCAGCATTACAACTCAGCGCTAGGCTT  2520
Calafl4-Spanish   ACCCAGTACACTGCAGCATGTAAGACCATAGAGTCAGCATTACAACTCAGCGCTAGGCTT  2520
                  ************************************************************

CV777-AF353511    GAGTCTGTTGAAGTTAACTCTATGCTTACCATTTCTGAAGAGGCTTTACAGTTAGCTACC  2580
Br1/87-Z25483     GAGTCTGTTGAAGTTAACTCTATGCTTACCATTTCTGAAGAGGCTTTACAGTTAGCTACC  2580
Calafl4-Spanish   GAGTCTGTTGAAGTTAACTCTATGCTTACTATTTCTGAAGAGGCTCTACAGTTAGCTACC  2580
                  ***************************** *************** **************

CV777-AF353511    ATCAGTTCGTTTAATGGTGATGGATATAACTTTACTAATGTGCTGGGTGCTTCCGTGTAC  2640
Br1/87-Z25483     ATCAGTTCGTTTAATGGTGATGGATATAACTTTACTAATGTGCTGGGTGCTTCCGTGTAC  2640
Calafl4-Spanish   ATTAGTTCGTTTAATGGTGATGGATATAATTTTACTAATTTGCTGGGTGTGTTTCGTGTAT  2640
                  ** ************************** ********  ********  *** *****
```

FIG. 10 K

```
CV777-AF353511    GATCCTGCAAGTGGCAGGGTGTGGTACAAAAAAGGTCTGTTATTGAAGACTTGCTTTTTAAT  2700
Br1/87-Z25483     GATCCTGCAAGTGGCAGGGTGTGGTACAAAAAAGGTCTGTTATTGAAGACTTGCTTTTTAAT  2700
Calaf14-Spanish   GATCCTGCAAGTGGCAGGGTGTGGTACAAAAAAGGTCTTTTATTGAAGACCTGCTTTTTAAT  2700
                  ************************************ *  ********** **********

CV777-AF353511    AAAGTGGTTACTAATGGCCTTGGTACTGTTGATGAAGACTATAAGCGCTGTTCTAATGGT   2760
Br1/87-Z25483     AAAGTGGTTACTAATGGCCTTGGTACTGTTGATGAAGACTATAAGCGCTGTTCTAATGGT   2760
Calaf14-Spanish   AAAGTGGTTACTAATGGCCTTGGTACTGTTGATGAAGACTATAAGCGCTGTTCTAATGGT   2760
                  ************************************************************

CV777-AF353511    CGCTCTGTGGCTGATCTAGTCTGTGCGCAGTATTACTCTGGTGTCATGGTACTACCTGGC   2820
Br1/87-Z25483     CGCTCTGTGGCTGATCTAGTCTGTGCGCAGTATTACTCTGGTGTCATGGTACTACCTGGC   2820
Calaf14-Spanish   CGCTCTGTGGCAGATCTAGTCTGTGCACAGTATTACTCTGGTGTCATGGTACTACCTGGT   2820
                  *********** ************* *********************************

CV777-AF353511    GTTGTTGACGCTGAGAAGCTTCACATGTACAGTGCCTCTCTCATAGTGGTATGGCGCTA   2880
Br1/87-Z25483     GTTGTTGACGCTGAGAAGCTTCACATGTACAGTGCCTCTCTCATAGGTGGTATGGCGCTA   2880
Calaf14-Spanish   GTTGTTGACGCTGAGAAGCTTCACATGTATAGTGCCTCTCTCATCGGTGGTATGGTGCTA   2880
                  *****************************  ************ ********* ****
```

FIG. 10L

```
CV777-AF353511   GGAGGTATAACTGCTGCAGCGGCATTGCCTTTTAGCTATGCTGTTCAAGCGAGACTCAAT 2940
Br1/87-Z25483    GGAGGTATAACTGCTGCAGCGGCATTGCCTTTTAGCTATGCTGTTCAAGCGAGACTCAAT 2940
Calaf14-Spanish  GGAGGTTTTACTTCTGCAGCGGCATTGCCTTTTAGCTATGCTGTTCAAGCTAGACTCAAT 2940
                 ******::*:*** ********************************* *********

CV777-AF353511   TATCTTGCTTTACAGACGGATGTTCTACAGCGGAACCAGCAATTGCTTGCTGAGTCTTTT 3000
Br1/87-Z25483    TATCTTGCTTTACAGACGGATGTTCTACAGCGGAACCAGCAATTGCTTGCTGAGTCTTTT 3000
Calaf14-Spanish  TATCTTGCTCTACAGACGGATGTTCTACAGCGGAACCAGCAATTGCTTGCTGAGTCTTTT 3000
                 ********* **************************************************

CV777-AF353511   AACTCTGCTATTGGTAATATAACTTCAGCCTTTGAGAGTGTTAAAGAGGCTATTAGTCAA 3060
Br1/87-Z25483    AACTCTGCTATTGGTAATATAACTTCAGCCTTTGAGAGTGTTAAAGAGGCTATTAGTCAA 3060
Calaf14-Spanish  AACTCTGCTATTGGTAATATAACTTCAGCCTTTGAGAGTGTTAAAGAGGCTATTAGTCAA 3060
                 ************************************************************

CV777-AF353511   ACTTCCAAGGGTTTGAACACTGTGGCTCATGCGCTTACTAAGGTTCAAGAGGTTGTTAAT 3120
Br1/87-Z25483    ACTTCCAAGGGTTTGAACACTGTGGCTCATGCGCTTACTAAGGTTCAAGAGGTTGTTAAT 3120
Calaf14-Spanish  ACTTCCAAGGGTTTGAACACTGTGGCTCATGCGCTTACTAAGGTTCAAGAGGTTGTTAAC 3120
                 ***********************************************************
```

FIG. 10 M

```
CV777-AF353511    TCGCAGGGTTCAGCTTTGAACCAACTTACCGTACAGCTGCAACACAACTTCCAAGCCATT  3180
Br1/87-Z25483     TCGCAGGGTTCAGCTTTGAACCAACTTACCGTACAGCTGCAACACAACTTCCAAGCCATT  3180
Calaf14-Spanish   TCGCAGGGTGCAGCTTTGACTCAACTTACCGTACAGCTGCAACACAACTTCCAAGCCATT  3180
                  ********* ********* ********************************** *****

CV777-AF353511    TCTAGTTCTATTGATGACATTTATTCCCGACTGGACATTCTTTCAGCCGATGTTCAGGTT  3240
Br1/87-Z25483     TCTAGTTCTATTGATGACATTTATTCCCGACTGGACATTCTTTTAGCCGATGTTCAGGTT  3240
Calaf14-Spanish   TCTAGTTCTATTGATGACATTTACTCTCGACTGGACATTCTTTCAGCCGATGTTCAGGTT  3240
                  *********************** ** *************** ****************

CV777-AF353511    GATCGTCTCATCACCGGCAGATTATCAGCACTTAATGCTTTTGTTGCCCAAACCCTCACT  3300
Br1/87-Z25483     GATCGTCTCATCACCGGCAGATTATCAGCACTTAATGCTTTTGTTGCCCAAACCCTCACT  3300
Calaf14-Spanish   GACCGTCTCATCACCGGCAGATTATCAGCACTTAATGCTTTTGTTGCTCAAACCCTCACT  3300
                  ** ******************************************** ***********

CV777-AF353511    AAGTATACTGAGGTTCAGGCTAGCAGGAAGCTAGCACAGCAAAAGGTTAATGAGTGCGTC  3360
Br1/87-Z25483     AAGTATACTGAGGTTCAGGCTAGCAGGAAGCTAGCACAGCAAAAGGTTAATGAGTGCGTC  3360
Calaf14-Spanish   AAGTATACTGAGGTTCAGGCTAGCAGGAAGCTAGCACAGCAAAAGGTTAATGAGTGCGTT  3360
                  ********************************************************** 
```

FIG. 10 N

```
CV777-AF353511    AAATCGCAATCTCAGCGGTTACGGTTTTTGTGGTGGTGATGGCGAGCACATTTCTCTCTG  3420
Br1/87-Z25483     AAATCGCAATCTCAGCGGTTACGGTTTTTGTGGTGGTGATGGCGAGCACATTTCTCTCTG  3420
Calaf14-Spanish   AAATCGCAATCTCAGCGGTTATGGTTTTTGTGGTGGTGATGGCGAGCACATTTCTCTCTG  3420
                  ********************* ************* ***********************

CV777-AF353511    GTACAGGCCGCACCTCAGGGCCTGCTGTTCTTACATACAGTACTTGTACCGGTGATTTT   3480
Br1/87-Z25483     GTACAGGCCGCACCTCAGGGCCTGCTGTCTTCTTACATACAGTACTTGTACCGGTGATTTT  3480
Calaf14-Spanish   GTACAGGCAGCACCTCAGGGCCTGCTGTTTTACATACAGTACTTGTACCGGTGATTTT    3480
                  ******** ******************* .      *************************

CV777-AF353511    GTAAATGTCTTGCCATCGCTGGCTTATGCGTTAATGGTGAAATTGCCTTGACTCTACGT   3540
Br1/87-Z25483     GTAAATGTTCTTGCCATCGCTGGCTTATGCGTTAATGGTTGAAATTGCCTTGACTCTACGT  3540
Calaf14-Spanish   GTAGATGTTATTGCCATCGCTGGCTTATGCGTTAACGATGAAATTGCCTTGACTCTACGT   3540
                  *** . *** . ********************* .  **********************

CV777-AF353511    GAGCCTGGCTTAGTCTTGTTTACGCATGAACTTCAAACTTATACTGCCGACGGAATATTTT 3600
Br1/87-Z25483     GAGCCTGGCTTAGTCTTGTTTACGCATGAACTTCAAACTTATACTGCGACGGAATATTTT  3600
Calaf14-Spanish   GAGCCTGGCTTAGTCTTGTTTACGCATGAACTTCAAAATCATACTGCGACGCGAATATTTT 3600
                  ********************************** *  .********.*********
```

FIG. 10 O

```
CV777-AF353511      GTTTCATCGCGACGTATGTTTGAACCTAGAAAACCTACCGTTAGTGATTTTGTTCAAATT 3660
Br1/87-Z25483       GTTTCATCGCGACGTATGTTTGAACCTAGAAAACCTACCGTTAGTGATTTTGTTCAAATT 3660
Calaf14-Spanish     GTTTCATCGCGACGTATGTTTGAACCTAGAAAACCTACCGTTAGTGATTTTGTTCAAATT 3660
                    ************************************************************

CV777-AF353511      GAGAGTTGTGTGGTCACCTATGTCAATCTGACTAGCGACCAGCTACCAGATGTAATCCCA 3720
Br1/87-Z25483       GAGAGTTGTGTGGTCACCTATGTCAATCTGACTAGCGACCAGCTACCAGATGTAATCCCA 3720
Calaf14-Spanish     GAGAGTTGTGTGGTCACCTATGTCAATTTGACTAGAGACCAACTACCAGATGTAATCCCA 3720
                    *************************** *******.*****.******************

CV777-AF353511      GATTACATCGATGTTAACAAAACACTTGATGAGATTTTAGCTTCTCTGCCCAATAGAACT 3780
Br1/87-Z25483       GATTACATCGATGTTAACAAAACACTTGATGAGATTTTAGCTTCTCTGCCCAATAGAACT 3780
Calaf14-Spanish     GATTACATCGATGTTAACAAAACACTTGATGAGATTTTAGCTTCTCTGCCCAATAGAACT 3780
                    ************************************************************

CV777-AF353511      GGTCCAAGTCTTCCCCTAGATGTTTTTAATGCCACTTATCTTAATCTTACTGGTGAAATT 3840
Br1/87-Z25483       GGTCCAAGTCTTCCCCTAGATGTTTTTAATGCCACTTATCTTAATCTTACTGGTGAAATT 3840
Calaf14-Spanish     GGTCCAAGTCTTCCTTTAGATGTTTTTAATGCCACTTATCTTAATCTCACTGGTGAAATT 3840
                    **************  ******************************* ************
```

FIG. 10 P

```
CV777-AF353511    GCAGATCTAGAGCAGCAGCGGTTCAGAGTCTCTCCGTAATACTACAGAAGAGCTCCGAAGTCTC  3900
Br1/87-Z25483     GCAGATCTAGAGCAGCAGCGGTTCAGAGTCTCTCCGTAATACTACAGAAGAGCTCCGAAGTCTC  3900
Calaf14-Spanish   GCAGATTTAGAGCAGCAGCGGTTCAGAGTCTCTCCGTAATACTACAGAGGAGCTCCAAAGTCTT  3900
                  ****** *********************************************** ****** *

CV777-AF353511    ATTAACAACATCAACAACACACTTGTTGACCTTGAGTGGCTCAACCGAGTTGAGACATAC  3960
Br1/87-Z25483     ATTAACAACATCAACAACACACTTGTTGACCTTGAGTGGCTCAACCGAGTTGAGACATAC  3960
Calaf14-Spanish   ATATATAATATCAACAACACTAGTTGACCTTGAGTGGCTCAACCGAGTTGAGACATAT  3960
                  ** *  * ***********  ************************************ *

CV777-AF353511    ATCAAGTGGCCGTGGTGGGTTTGGTTGATCATTGTTATTGTTCTCATCTTTGTTGTGTCA  4020
Br1/87-Z25483     ATCAAGTGGCCGTGGTGGGTTTGGTTGATCATTGTTATTGTTCTCATCTTTGTTGTGTCA  4020
Calaf14-Spanish   ATCAAGTGGCCGTGGTGGTTGGTTTGGTTGATTATTTTCATTGTTCTCATCTTTGTTGTGTCA  4020
                  ****************** ***** *   ** *** *  * ******************

CV777-AF353511    TTACTAGTGTTCTGCTGCATTTCCACGGGTTGTTGTGGATGCTGCGGTTGCTGCGGTGCT  4080
Br1/87-Z25483     TTACTAGTGTTCTGCTGCATTTCCACGGGTTGTTGTGGATGCTGCGGTTGCTGCGGTGCT  4080
Calaf14-Spanish   TTACTAGTGTTCTGCTGCATTCCCACGGGTTGTTGTGGATGCTGCGGTTGCTGCTGTGCT  4080
                  ********************* ******************************* *****
```

FIG. 10 Q

```
CV777-AF353511    TGTTTTTCAGGTTGTGTGTAGGGGTCCTAGACTTCAACCTTACGAAGCTTTTGAAAAGGTC  4140
Br1/87-Z25483     TGTTTTTCAGGTTGTGTGTAGGGGTCCTAGACTTCAACCTTACGAAGCTTTTGAAAAGGTC  4140
Calaf14-Spanish   TGTTTTTCAGGTTGTGTGTAGGGGTCCTAGACTTCAACCTTACGAAGTTTTGAAAAGGTC   4140
                  ***********************************************  ***********

CV777-AF353511    CACGTGCAGTGA  4152
Br1/87-Z25483     CACGTGCAGTGA  4152
Calaf14-Spanish   CACGTGCAGTGA  4152
                  ************
```

Complete spike protein encoding DNA sequences, strain CV777 (SEQ ID NO:3), strain Br1-87 (SEQ ID NO:2), and strain Calaf14 (SEQ ID NO:1)

FIG. 10 R

SEQUENCE LISTING

<160> NUMBER OF SEQ ID NOS: 12

<210> SEQ ID NO 1
<211> LENGTH: 4152
<212> TYPE: DNA
<213> ORGANISM: Artificial Sequence
<220> FEATURE:
<223> OTHER INFORMATION: DNA sequence encoding spike protein of PEDV
      strain Calaf14

<400> SEQUENCE: 1

```
atgaagtctt taaattactt ctggttgttc ttaccagtac tttcaacact cagcctacca      60
caagatgtca ctaggtgcca gtccactatt aacttcaggc ggttcttttc aaaatttaat     120
gtgcaggcac ctgctgtcgt tgtgttgggt ggttatctac ctagtatgaa ctcctctagc     180
tggtactgtg gcacaggtct tgaaactgct agtggcgtgc atggtatttt cctcagttac     240
atcgatgctg gtcagggctt tgagattggc atttcacagg agccgtttga tcctagtggt     300
taccagcttt atttacataa ggccactaat ggtaaccata atgctattgc acgactgcgc     360
atttgccagt ttccaaataa taaaacattg ggccctactg ttaatgatgt tacaacaggt     420
cgtaactgcc tattcaacaa agccattcca gcttatatgc aggatggaaa aaacatcgtt     480
gtcggcataa catgggacaa tgatcgtgtc actgtttttg ctgacaagat ctatcatttt     540
tatctcaaaa atgattggtc ccgtgttgcg acaagatgtt acaataaaag aagttgtgct     600
atgcaatatg tttatacacc tacctactac atgcttaatg ttactagtgc aggtgaggat     660
ggcatttatt atgaaccatg tacagctaat tgcagtggtt acgctgccaa tgtgtttgcc     720
actgattcta atggccacat accagaaggt tttagtttta taattggtt tctttttgtcc     780 aatgattcca ctttgttgca tggtaaggtg gtttccaacc aacctttgtt ggtcaattgt     840
cttttggcca ttcctaagat ttatggacta ggccaatttt tctcattcaa tcaaacgatg     900
gatggcgttt gtaatggagc tgctgcgcag cgtgcaccag aggctctgag gtttaatatt     960
aatgacacct ctgtcattct tgctgaaggc tcaattgtac ttcacactgc tttaggaaca    1020
aatctttctt ttgtttgcag taattcttca gatcctcatt tagctacctt caccatacct    1080
ctgggtgcta cccaagtacc ctattattgt ttttcttaag tggatactta caactccact    1140
gtttataaat ttttggctgt tttacctcct accgtcaggg aaattgtcat caccaagtat    1200
```

```
ggtgatgttt atgtcaatgg gtttggatac ttgcatctcg gtttgttgga tgctgtcaca    1260
attaatttca ctggtcatgg cactgacgat gatgttctg gttttggac catagcatcg      1320 actaattttg ttgatgcact catcgaagtt caaggaactg ccattcagcg tattctttat    1380
tgtgatgatc ctgttagcca actcaagtgt tctcaggttg cttttgacct tgacgatggt    1440
ttttacccta tttcttctag aaaccttctg agtcatgaac agccaatttc ttttgttact    1500
ctgccatcat ttaatgatca ttcttttgtt aacattactg tctctgcttc ctttggtggt    1560
catagtggtg ccaaccttat tgcatctgac actactatca atgggtttag ttctttctgt    1620
gttgacacta gacaatttac catttcactg ttttataacg ttacaaacag ttatggttat    1680
gtgtctaaat cacaggacag taattgccct ttcaccttgc aatctgttaa tgattacctg    1740
tcttttagca aattttgtgt ttccaccaac cttttggcta gtgactgtac catagatctt    1800
tttggttacc ctgagtttgg tagtggtgtt aagtttacgt ccctttactt tcaattcaca    1860
aagggtgagt tgattactgg cacgcctaaa ccacttgaag gtgtcacgga cgtttctttt    1920
atgactctgg atgtgtgtac caagtatact atctatggct ttaaaggtga gggtatcatt    1980
acccttacaa attctagctt tttggcaggt gtttattaca catctgattc tggacagttg    2040
ttagccttta agaatgtcac tagtggtgct gtttattctg ttacgccatg ttcttttttca   2100 gagcaggctg catatgttga tgatgatata gtgggtgtta tttctagttt gtctagctcc    2160
acttttaaca gtactaggga gttgcctggt ttcttctacc attctaatga tggctctaat    2220
tgtacagagc ctgtgttggt gtatagtaac ataggtgttt gtaaatctgg cagtattggc    2280
tacgtcccat ctcagtctgg ccaagtcaag attgcaccca cggttactgg gaatatcagt    2340
attcccacca actttagtat gagtattagg acagaatatt tacagcttta caacacgcct    2400
gttagtgttg attgtgccac atatgtttgt aatggtaact ctcgttgtaa acaattactc    2460
acccagtaca ctgcagcatg taagaccata gagtcagcat acaactcag cgctaggctt    2520 gagtctgttg aagttaactc tatgcttact atttctgaag aggctctaca gttagctacc    2580
attagttcgt ttaatggtga tggatataat tttactaatg tgctgggtgt ttctgtgtat    2640
gatcctgcaa gtggcagggt ggtacaaaaa aggtctttta ttgaagacct gcttttttaat   2700 aaagtggtta ctaatggcct tggtactgtt gatgaagact ataagcgctg ttcaatggt    2760 cgctctgtgg cagatctagt ctgtgcacag tattactctg gtgtcatggt actacctggt    2820
gttgttgacg ctgagaagct tcacatgtat agtgcgtctc tcatcggtgg tatggtgcta    2880
ggaggtttta cttctgcagc ggcattgcct tttagctatg ctgttcaagc tagactcaat    2940
tatcttgctc tacagacgga tgttctacag cggaaccagc aattgcttgc tgagtctttt    3000
aactctgcta ttgtaatat aacttcagcc tttgagagtt taaagaggc tattagtcaa    3060 acttccaagg gtttgaacac tgtggctcat gcgcttacta aggttcaaga ggttgttaac    3120
tcgcagggtg cagctttgac tcaacttacc gtacagctgc aacacaactt ccaagccatt    3180
tctagttcta ttgatgacat ttactctcga ctggacattc tttcagccga tgttcaggtt    3240
gaccgtctca tcaccggcag attatcagca cttaatgctt tgttgctca aaccctcact    3300 aagtatactg aggttcaggc tagcaggaag ctagcacaga aaaaggttaa tgagtgcgtt    3360
aaatcgcaat ctcagcgtta tggttttttgt ggtggtgatg gcgagcacat tttctctctg    3420
gtacaggcag cacctcaggg cctgctgttt ttacatacag tacttgtacc gggtgatttt    3480
gtagatgtta ttgccatcgc tggcttatgc gttaacgatg aaattgcctt gactctacgt    3540
```

```
gagcctggct tagtcttgtt tacgcatgaa cttcaaaatc atactgcgac ggaatatttt    3600
gtttcatcgc gacgtatgtt tgaacctaga aaacctaccg ttagtgattt tgttcaaatt    3660
gagagttgtg tggtcaccta tgtcaatttg actagagacc aactaccaga tgtaatccca    3720
gattacatcg atgttaacaa aacacttgat gagattttag cttctctgcc aatagaact     3780 ggtccaagtc ttcctttaga tgtttttaat gccacttatc ttaatctcac tggtgaaatt    3840
gcagatttag agcagcgttc agagtctctc cgtaatacta cagaggagct ccaaagtctt    3900
atatataata tcaacaacac actagttgac cttgagtggc tcaaccgagt tgagacatat    3960
atcaagtggc cgtggtgggt ttggttgatt attttcattg ttctcatctt tgttgtgtca    4020
ttactagtgt tctgctgcat ttccacgggt tgttgtggat gctgcggctg ctgctgtgct    4080 tgttttcag gttgttgtag gggtcctaga cttcaacctt acgaagtttt tgaaaaggtc     4140
cacgtgcagt ga                                                        4152
```

<210> SEQ ID NO 2
<211> LENGTH: 4152
<212> TYPE: DNA
<213> ORGANISM: Artificial Sequence
<220> FEATURE:
<223> OTHER INFORMATION: DNA sequence encoding spike protein of PEDV
      strain Br1-87

<400> SEQUENCE: 2

```
atgaggtctt taatttactt ctggttgctc ttaccagtac ttccaacact cagcctacca      60
caagatgtca ctaggtgcca gtctactact aactttaggc ggttcttttc aaaatttaat     120
gttcaggcac ctgccgtcgt cgttttgggt ggttacctac ctagtatgaa ctcttctagc     180
tggtactgtg gcacaggcat tgaaactgct agtggcgttc atggtatttt tctcagctac     240
atcgattctg gtcagggctt tgagattggc atttcgcaag agccgtttga tcctagtggt     300
taccagcttt atttacataa ggccactaat ggtaacacta tgctactgc acgactgcgc     360 atttgccagt ttcccgataa taaaacattg ggccctactg ttaatgatgt tacaacaggt     420
cgtaactgcc tattcaacaa agccattcca gcttatatgc gtgatggaaa agatattgtt     480
gtcggcataa catgggataa tgatcgtgtc actgtttttg ctgacaagat ctatcatttt     540
tatcttaaaa atgattggtc ccgcgttgcg acaagatgtt acaatcgcag aagttgtgct     600
atgcaatatg tttatacacc tacctactac atgcttaatg ttactagtgc aggtgaggat     660
ggcatttatt atgaaccctg tacagctaat tgcactggtt acgctgccaa tgtatttgcc     720
actgattcca atggccatat accagaaggt tttagttttta ataattggtt tcttttatcc    780
aatgactcca ctttgttgca tggtaaagtg gtttccaacc aacccttgtt ggtcaattgt    840
cttttggcca ttcctaagat ttatggacta ggccaatttt tctcattcaa tcacacgatg    900
gatggcgttt gtaatggagc tgctgtggat cgtgccccag aggctctgag gtttaatatt    960
aatgacacct ccgtcattct tgctgaaggc tcaattgtac ttcatactgc tttaggaaca   1020
aatctttctt tgtttgcag taattcctca gatcctcatt tagccatctt tgccatacct   1080
ctgggtgcta ctgaagtacc ctactattgc tttcttaaag tggatactta caactccact   1140
gtttataaat tctggctgtg tttaccttct actgtcaggg aaattgtcat caccaagtat   1200
ggtgatgttt atgtcaatgg gtttggctat tgcatctcg gttgttgga tgctgtcaca    1260 atttatttca ctggtcatgg cactgacgat gacgtttcag gttctggac catagcatcg    1320 actaattttg ttgatgcact catcgaggtt caaggaactt ccattcagcg tattctttat    1380
```

```
tgtgatgatc ctgttagcca actcaagtgt tctcaggttg cttttgacct tgacgatggt    1440
ttttacccca tctcttctag aaaccttctg agtcacgaac agccaatttc ttttgttact    1500
ttgccatcat ttaatgatca ttcttttgtt aatattactg tctctgcggc ttttggtggt    1560
cttagtagtg ccaatctcgt tgcatctgac actactatca atgggtttag ttctttctgt    1620
gttgacacta gacaatttac cattacactg ttttataatg ttacaaacag ttatggttat    1680
gtgtctaaat cacaggatag taattgtcct ttcaccttgc aatctgttaa tgattacctg    1740
tcttttagca aattttgtgt ttcaaccagc cttttggctg gtgcttgtac catagatctt    1800
tttggttacc ctgcgttcgg tagtggtgtt aagttgacgt cccttttattt tcaattcaca    1860 aaaggtgagt tgattactgg cacgcctaaa ccacttgaag gtatcacaga cgtttctttt    1920
atgactctgg atgtgtgtac caagtatact atctatggct ttaaaggtga gggtattatt    1980
acccttacaa attctagcat tttggcaggt gtttattata catctgattc tggacagttg    2040
ttagccttta agaatgtcac tagtggtgct gtttattctg tcacgccatg ttcttttttca    2100 gagcaggctg catatgttaa tgatgatata gtgggtgtta tttctagttt gtctaactcc    2160
acttttaaca atactaggga gttgcctggt ttcttctacc attctaatga cggctccaat    2220
tgtacagagc ctgtgttggt gtatagtaac ataggtgttt gtaaatctgg cagtattggc    2280
tatgttccat ctcagtatgg ccaagtcaag attgcaccca cggttactgg gaatattagt    2340
attcccacca actttagtat gagtattaga acagaatatt tacagcttta caacacgcct    2400
gttagtgttg attgtgctac atatgtttgt aatggtaact ctcgttgtaa acaattactc    2460
acccagtaca ctgcagcatg taagaccata gagtcagcat acaactcag cgctaggctt    2520 gagtctgttg aagttaactc tatgcttacc atttctgaag aggctttaca gttagctacc    2580
atcagttcgt ttaatggtga tggatataac tttactaatg tgctgggtgc ttccgtgtac    2640
gatcctgcaa gtggcagggt ggtacaaaaa aggtctgtta ttgaagactt gcttttttaat    2700 aaagtggtta ctaatggcct tggtactgtt gatgaagact ataagcgctg ttctaatggt    2760
cgctctgtgg ctgatctagt ctgtgcgcag tattactctg gtgtcatggt actacctggc    2820
gttgttgacg ctgagaagct tcacatgtac agtgcgtctc tcataggtgg tatggcgcta    2880
ggaggtataa ctgctgcagc ggcattgcct tttagctatg ctgttcaagc gagactcaat    2940
tatcttgctt tacagacgga tgttctacag cggaaccagc aattgcttgc tgagtctttt    3000
aactctgcta ttggtaatat aacttcagcc tttgagagtg ttaaagaggc tattagtcaa    3060
acttccaagg gtttgaacac tgtggctcat gcgcttacta aggttcaaga ggttgttaat    3120
tcgcagggtt cagctttgaa ccaacttacc gtacagctgc aacacaactt ccaagccatt    3180
tctagttcta ttgatgacat ttattcccga ctggacattc ttttagccga tgttcaggtt    3240
gatcgtctca tcaccggcag attatcagca cttaatgctt ttgttgccca aacctcact    3300 aagtatactg aggttcaggc tagcaggaag ctagcacagc aaaaggttaa tgagtgcgtc    3360
aaatcgcaat ctcagcgtta cggttttgt ggtggtgatg cgagcacat tttctctctg    3420 gtacaggccg cacctcaggg cctgctgttc ttacatacag tacttgtacc gggtgatttt    3480
gtaaatgttc ttgccatcgc tggcttatgc gttaatggtg aaattgcctt gactctacgt    3540
gagcctggct tagtcttgtt tacgcatgaa cttcaaactt atactgcgac ggaatatttt    3600
gtttcatcgc gacgtatgtt tgaacctaga aaacctaccg ttagtgattt tgttcaaatt    3660
gagagttgtg tggtcaccta tgtcaatctg actagcgacc agctaccaga tgtaatccca    3720
gattacatcg atgttaacaa aacacttgat gagatttag cttctctgcc caatagaact    3780
```

| | |
|---|---:|
| ggtccaagtc ttcccctaga tgttttaat gccacttatc ttaatcttac tggtgaaatt | 3840 |
| gcagatctag agcagcgttc agagtctctc cgtaatacta cagaagagct ccgaagtctc | 3900 |
| attaacaaca tcaacaacac acttgttgac cttgagtggc tcaaccgagt tgagacatac | 3960 |
| atcaagtggc cgtggtgggt ttggttgatc attgttattg ttctcatctt tgttgtgtca | 4020 |
| ttactagtgt tctgctgcat ttccacgggt tgttgtggat gctgcggttg ctgcggtgct | 4080 |
| tgttttcag gttgttgtag gggtcctaga cttcaacctt acgaagcttt tgaaaaggtc | 4140 |
| cacgtgcagt ga | 4152 |

<210> SEQ ID NO 3
<211> LENGTH: 4152
<212> TYPE: DNA
<213> ORGANISM: Artificial Sequence
<220> FEATURE:
<223> OTHER INFORMATION: DNA sequence encoding spike protein of PEDV strain CV777

<400> SEQUENCE: 3

| | |
|---|---:|
| atgaggtctt taatttactt ctggttgctc ttaccagtac ttccaacact cagcctacca | 60 |
| caagatgtca ctaggtgcca gtctactact aactttaggc ggttctttc aaaatttaat | 120 |
| gttcaggcac ctgccgtcgt cgttttgggt ggttacctac ctagtatgaa ctcttctagc | 180 |
| tggtactgtg gcacaggcat tgaaactgct agtggcgttc atggtatttt tctcagctac | 240 |
| atcgattctg gtcagggctt tgagattggc atttcgcaag agccgtttga tcctagtggt | 300 |
| taccagcttt atttacataa ggccactaat ggtaacacta tgctattgc acgactcgc | 360 |
| atttgccagt tcccgataa taaaacattg ggccctactg ttaatgatgt tacaacaggt | 420 |
| cgtaactgcc tattcaacaa agccattcca gcttatatgc gtgatggaaa agatattgtt | 480 |
| gtcggcataa catgggataa tgatcgtgtc actgtttttg ctgacaagat ctatcatttt | 540 |
| tatcttaaaa atgattggtc ccgcgttgcg acaagatgtt acaatcgcag aagttgtgct | 600 |
| atgcaatatg tttatacacc tacctactac atgcttaatg ttactagtgc aggtgaggat | 660 |
| ggcattttatt atgaaccctg tacagctaat tgcactggtt acgctgccaa tgtatttgcc | 720 |
| actgattcca atggccatat accagaaggt tttagtttta taattggtt tcttttatcc | 780 |
| aatgactcca ctttgttgca tggtaaagtg gtttccaacc aacccttgtt ggtcaattgt | 840 |
| cttttggcca ttcctaagat ttatggacta ggccaatttt tctcattcaa tcacacgatg | 900 |
| gatgccgttt gtaatggagc tgctgtggat cgtgccccag aggctctgag gtttaatatt | 960 |
| aatgacacct ccgtcattct tgctgaaggc tcaattgtac ttcatactgc tttaggaaca | 1020 |
| aatctttctt ttgttgcag taattcctca gatcctcatt tagccatctt tgccatacct | 1080 |
| ctgggtgcta ctgaagtacc ctactattgc tttcttaaag tggatactta caactccact | 1140 |
| gttttataaat tcttggctgt tttacctcct actgtcaggg aaattgtcat caccaagtat | 1200 |
| ggtgatgttt atgtcaatgg gtttggctat ttgcatctcg gttgttgga tgctgtcaca | 1260 |
| attaatttca ctggtcatgg cactgacgat gacgtttcag gtttctggac catagcatcg | 1320 |
| actaatttg ttgatgcact catcgaggtt caaggaactt ccattcagcg tattctttat | 1380 |
| tgtgatgatc ctgttagcca actcaagtgt tctcaggttg cttttgacct tgacgatggt | 1440 |
| ttttacccca tctcttctag aaaccttctg agtcacgaac agccaatttc ttttgttact | 1500 |
| ttgccatcat ttaatgatca ttcttttgtt aatattactg tctctgcggc ttttggtggt | 1560 |
| cttagtagtg ccaatctcgt tgcatctgac actactatca atgggtttag ttctttctgt | 1620 |

```
gttgacacta gacaatttac cattacactg ttttataatg ttacaaacag ttatggttat    1680
gtgtctaaat cacaggatag taattgtcct ttcaccttgc aatctgttaa tgattacctg    1740
tcttttagca aattttgtgt ttcaaccagc cttttggctg gtgcttgtac catagatctt    1800
tttggttacc ctgcgttcgg tagtggtgtt aagttgacgt cccttttattt tcaattcaca    1860 aaaggtgagt tgattactgg cacgcctaaa ccacttgaag gtatcacaga cgtttctttt    1920
atgactctgg atgtgtgtac caagtatact atctatggct ttaaaggtga gggtattatt    1980
acccttacaa attctagcat tttggcaggt gtttattata catctgattc tggacagttg    2040
ttagccttta agaatgtcac tagtggtgct gtttattctg tcacgccatg ttcttttttca    2100 gagcaggctg catatgttaa tgatgatata gtgggtgtta tttctagttt gtctaactcc    2160
acttttaaca atactaggga gttgcctggt ttccttctacc attctaatga cggctccaat    2220
tgtacagagc ctgtgttggt gtatagtaac ataggtgttt gtaaatctgg cagtattggc    2280
tatgttccat ctcagtatgg ccaagtcaag attgcaccca cggttactgg gaatattagt    2340
attcccacca actttagtat gagtattaga acagaatatt tacagcttta caacacgcct    2400
gttagtgttg attgtgctac atatgttgt aatggtaact ctcgttgtaa acaattactc    2460
acccagtaca ctgcagcatg taagaccata gagtcagcat tacaactcag cgctaggctt    2520
gagtctgttg aagttaactc tatgcttacc atttctgaag aggctttaca gttagctacc    2580
atcagttcgt ttaatggtga tggatataac tttactaatg tgctgggtgc ttccgtgtac    2640
gatcctgcaa gtggcagggt ggtacaaaaa aggtctgtta ttgaagactt gcttttttaat    2700 aaagtggtta ctaatggcct tggtactgtt gatgaagact ataagcgctg ttctaatggt    2760
cgctctgtgg ctgatctagt ctgtgcgcag tattactctg gtgtcatggt actacctggc    2820
gttgttgacg ctgagaagct tcacatgtac agtgcgtctc tcataggtgg tatggcgcta    2880
ggaggtataa ctgctgcagc ggcattgcct tttagctatg ctgttcaagc gagactcaat    2940
tatcttgctt tacagacgga tgttctacag cggaaccagc aattgcttgc tgagtctttt    3000
aactctgcta ttggtaatat aacttcagcc tttgagagtg ttaaagaggc tattagtcaa    3060
acttccaagg gtttgaacac tgtggctcat gcgcttacta aggttcaaga ggttgttaat    3120
tcgcagggtt cagctttgaa ccaacttacc gtacagctgc aacacaactt ccaagccatt    3180
tctagttcta ttgatgacat ttattcccga ctggacattt tttcagccga tgttcaggtt    3240
gatcgtctca tcaccggcag attatcagca cttaatgctt tgttgcccca aaccctcact    3300
aagtatactg aggttcaggc tagcaggaag ctagcacagc aaaaggttaa tgagtgcgtc    3360
aaatcgcaat ctcagcgtta cggttttttgt ggtggtgatg gcgagcacat tttctctctg    3420
gtacaggccg cacctcaggg cctgctgttc ttacatacag tacttgtacc gggtgatttt    3480
gtaaatgttc ttgccatcgc tggcttatgc gttaatggtg aaattgcctt gactctacgt    3540
gagcctggct tagtcttgtt tacgcatgaa cttcaaactt atactgcgac ggaatatttt    3600
gtttcatcgc gacgtatgtt tgaacctaga aaacctaccg ttagtgattt tgttcaaatt    3660
gagagttgtg tggtcaccta tgtcaatctg actagcgacc agctaccaga tgtaatccca    3720
gattacatcg atgttaacaa acacttgat gagattttag cttctctgcc caatagaact    3780
ggtccaagtc ttcccctaga tgtttttaat gccacttatc ttaatcttac tggtgaaatt    3840
gcagatctag agcagcgttc agagtctctc cgtaatacta cagaagagct ccgaagtctc    3900
attaacaaca tcaacaacac acttgttgac cttgagtggc tcaaccgagt tgagacatac    3960
```

-continued

```
atcaagtggc cgtggtgggt ttggttgatc attgttattg ttctcatctt tgttgtgtca    4020
ttactagtgt tctgctgcat ttccacgggt tgttgtggat gctgcggttg ctgcggtgct    4080 tgttttcag gttgttgtag gggtcctaga cttcaacctt acgaagcttt tgaaaaggtc     4140
cacgtgcagt ga                                                        4152
```

<210> SEQ ID NO 4
<211> LENGTH: 1383
<212> TYPE: PRT
<213> ORGANISM: Artificial Sequence
<220> FEATURE:
<223> OTHER INFORMATION: amino acid sequence of spike protein of PEDV strain Calaf14

<400> SEQUENCE: 4

Met Lys Ser Leu Asn Tyr Phe Trp Leu Phe Leu Pro Val Leu Ser Thr
1               5                   10                  15

Leu Ser Leu Pro Gln Asp Val Thr Arg Cys Gln Ser Thr Ile Asn Phe
            20                  25                  30

Arg Arg Phe Phe Ser Lys Phe Asn Val Gln Ala Pro Ala Val Val Val
        35                  40                  45

Leu Gly Gly Tyr Leu Pro Ser Met Asn Ser Ser Trp Tyr Cys Gly
    50                  55                  60

Thr Gly Leu Glu Thr Ala Ser Gly Val His Gly Ile Phe Leu Ser Tyr
65                  70                  75                  80

Ile Asp Ala Gly Gln Gly Phe Glu Ile Gly Ile Ser Gln Glu Pro Phe
                85                  90                  95

Asp Pro Ser Gly Tyr Gln Leu Tyr Leu His Lys Ala Thr Asn Gly Asn
            100                 105                 110

His Asn Ala Ile Ala Arg Leu Arg Ile Cys Gln Phe Pro Asn Asn Lys
        115                 120                 125

Thr Leu Gly Pro Thr Val Asn Asp Val Thr Thr Gly Arg Asn Cys Leu
    130                 135                 140

Phe Asn Lys Ala Ile Pro Ala Tyr Met Gln Asp Gly Lys Asn Ile Val
145                 150                 155                 160

Val Gly Ile Thr Trp Asp Asn Asp Arg Val Thr Val Phe Ala Asp Lys
                165                 170                 175

Ile Tyr His Phe Tyr Leu Lys Asn Asp Trp Ser Arg Val Ala Thr Arg
            180                 185                 190

Cys Tyr Asn Lys Arg Ser Cys Ala Met Gln Tyr Val Tyr Thr Pro Thr
        195                 200                 205

Tyr Tyr Met Leu Asn Val Thr Ser Ala Gly Glu Asp Gly Ile Tyr Tyr
    210                 215                 220

Glu Pro Cys Thr Ala Asn Cys Ser Gly Tyr Ala Ala Asn Val Phe Ala
225                 230                 235                 240

Thr Asp Ser Asn Gly His Ile Pro Glu Gly Phe Ser Phe Asn Asn Trp
                245                 250                 255

Phe Leu Leu Ser Asn Asp Ser Thr Leu Leu His Gly Lys Val Val Ser
            260                 265                 270

Asn Gln Pro Leu Leu Val Asn Cys Leu Leu Ala Ile Pro Lys Ile Tyr
        275                 280                 285

Gly Leu Gly Gln Phe Phe Ser Phe Asn Gln Thr Met Asp Gly Val Cys
    290                 295                 300

Asn Gly Ala Ala Ala Gln Arg Ala Pro Glu Ala Leu Arg Phe Asn Ile
305                 310                 315                 320

-continued

Asn Asp Thr Ser Val Ile Leu Ala Glu Gly Ser Ile Val Leu His Thr
                325                 330                 335

Ala Leu Gly Thr Asn Leu Ser Phe Val Cys Ser Asn Ser Ser Asp Pro
                340                 345                 350

His Leu Ala Thr Phe Thr Ile Pro Leu Gly Ala Thr Gln Val Pro Tyr
                355                 360                 365

Tyr Cys Phe Leu Lys Val Asp Thr Tyr Asn Ser Thr Val Tyr Lys Phe
                370                 375                 380

Leu Ala Val Leu Pro Pro Thr Val Arg Glu Ile Val Ile Thr Lys Tyr
385                 390                 395                 400

Gly Asp Val Tyr Val Asn Gly Phe Gly Tyr Leu His Leu Gly Leu Leu
                405                 410                 415

Asp Ala Val Thr Ile Asn Phe Thr Gly His Gly Thr Asp Asp Asp Val
                420                 425                 430

Ser Gly Phe Trp Thr Ile Ala Ser Thr Asn Phe Val Asp Ala Leu Ile
                435                 440                 445

Glu Val Gln Gly Thr Ala Ile Gln Arg Ile Leu Tyr Cys Asp Asp Pro
                450                 455                 460

Val Ser Gln Leu Lys Cys Ser Gln Val Ala Phe Asp Leu Asp Asp Gly
465                 470                 475                 480

Phe Tyr Pro Ile Ser Ser Arg Asn Leu Leu Ser His Glu Gln Pro Ile
                485                 490                 495

Ser Phe Val Thr Leu Pro Ser Phe Asn Asp His Ser Phe Val Asn Ile
                500                 505                 510

Thr Val Ser Ala Ser Phe Gly Gly His Ser Gly Ala Asn Leu Ile Ala
                515                 520                 525

Ser Asp Thr Thr Ile Asn Gly Phe Ser Ser Phe Cys Val Asp Thr Arg
530                 535                 540

Gln Phe Thr Ile Ser Leu Phe Tyr Asn Val Thr Asn Ser Tyr Gly Tyr
545                 550                 555                 560

Val Ser Lys Ser Gln Asp Ser Asn Cys Pro Phe Thr Leu Gln Ser Val
                565                 570                 575

Asn Asp Tyr Leu Ser Phe Ser Lys Phe Cys Val Ser Thr Asn Leu Leu
                580                 585                 590

Ala Ser Asp Cys Thr Ile Asp Leu Phe Gly Tyr Pro Glu Phe Gly Ser
                595                 600                 605

Gly Val Lys Phe Thr Ser Leu Tyr Phe Gln Phe Thr Lys Gly Glu Leu
                610                 615                 620

Ile Thr Gly Thr Pro Lys Pro Leu Glu Gly Val Thr Asp Val Ser Phe
625                 630                 635                 640

Met Thr Leu Asp Val Cys Thr Lys Tyr Thr Ile Tyr Gly Phe Lys Gly
                645                 650                 655

Glu Gly Ile Ile Thr Leu Thr Asn Ser Ser Phe Leu Ala Gly Val Tyr
                660                 665                 670

Tyr Thr Ser Asp Ser Gly Gln Leu Leu Ala Phe Lys Asn Val Thr Ser
                675                 680                 685

Gly Ala Val Tyr Ser Val Thr Pro Cys Ser Phe Ser Glu Gln Ala Ala
                690                 695                 700

Tyr Val Asp Asp Asp Ile Val Gly Val Ile Ser Ser Leu Ser Ser Ser
705                 710                 715                 720

Thr Phe Asn Ser Thr Arg Glu Leu Pro Gly Phe Phe Tyr His Ser Asn
                725                 730                 735

Asp Gly Ser Asn Cys Thr Glu Pro Val Leu Val Tyr Ser Asn Ile Gly

```
                740             745             750
Val Cys Lys Ser Gly Ser Ile Gly Tyr Val Pro Ser Gln Ser Gly Gln
            755             760             765
Val Lys Ile Ala Pro Thr Val Thr Gly Asn Ile Ser Ile Pro Thr Asn
            770             775             780
Phe Ser Met Ser Ile Arg Thr Glu Tyr Leu Gln Leu Tyr Asn Thr Pro
785             790             795             800
Val Ser Val Asp Cys Ala Thr Tyr Val Cys Asn Gly Asn Ser Arg Cys
                805             810             815
Lys Gln Leu Leu Thr Gln Tyr Thr Ala Ala Cys Lys Thr Ile Glu Ser
            820             825             830
Ala Leu Gln Leu Ser Ala Arg Leu Glu Ser Val Glu Val Asn Ser Met
            835             840             845
Leu Thr Ile Ser Glu Glu Ala Leu Gln Leu Ala Thr Ile Ser Ser Phe
            850             855             860
Asn Gly Asp Gly Tyr Asn Phe Thr Asn Val Leu Gly Val Ser Val Tyr
865             870             875             880
Asp Pro Ala Ser Gly Arg Val Val Gln Lys Arg Ser Phe Ile Glu Asp
                885             890             895
Leu Leu Phe Asn Lys Val Val Thr Asn Gly Leu Gly Thr Val Asp Glu
            900             905             910
Asp Tyr Lys Arg Cys Ser Asn Gly Arg Ser Val Ala Asp Leu Val Cys
            915             920             925
Ala Gln Tyr Tyr Ser Gly Val Met Val Leu Pro Gly Val Val Asp Ala
            930             935             940
Glu Lys Leu His Met Tyr Ser Ala Ser Leu Ile Gly Gly Met Val Leu
945             950             955             960
Gly Gly Phe Thr Ser Ala Ala Ala Leu Pro Phe Ser Tyr Ala Val Gln
                965             970             975
Ala Arg Leu Asn Tyr Leu Ala Leu Gln Thr Asp Val Leu Gln Arg Asn
            980             985             990
Gln Gln Leu Leu Ala Glu Ser Phe Asn Ser Ala Ile Gly Asn Ile Thr
            995             1000            1005
Ser Ala Phe Glu Ser Val Lys Glu Ala Ile Ser Gln Thr Ser Lys
            1010            1015            1020
Gly Leu Asn Thr Val Ala His Ala Leu Thr Lys Val Gln Glu Val
            1025            1030            1035
Val Asn Ser Gln Gly Ala Ala Leu Thr Gln Leu Thr Val Gln Leu
            1040            1045            1050
Gln His Asn Phe Gln Ala Ile Ser Ser Ser Ile Asp Asp Ile Tyr
            1055            1060            1065
Ser Arg Leu Asp Ile Leu Ser Ala Asp Val Gln Val Asp Arg Leu
            1070            1075            1080
Ile Thr Gly Arg Leu Ser Ala Leu Asn Ala Phe Val Ala Gln Thr
            1085            1090            1095
Leu Thr Lys Tyr Thr Glu Val Gln Ala Ser Arg Lys Leu Ala Gln
            1100            1105            1110
Gln Lys Val Asn Glu Cys Val Lys Ser Gln Ser Gln Arg Tyr Gly
            1115            1120            1125
Phe Cys Gly Gly Asp Gly Glu His Ile Phe Ser Leu Val Gln Ala
            1130            1135            1140
Ala Pro Gln Gly Leu Leu Phe Leu His Thr Val Leu Val Pro Gly
            1145            1150            1155
```

```
Asp Phe Val Asp Val Ile Ala Ile Ala Gly Leu Cys Val Asn Asp
    1160                1165                1170

Glu Ile Ala Leu Thr Leu Arg Glu Pro Gly Leu Val Leu Phe Thr
    1175                1180                1185

His Glu Leu Gln Asn His Thr Ala Thr Glu Tyr Phe Val Ser Ser
    1190                1195                1200

Arg Arg Met Phe Glu Pro Arg Lys Pro Thr Val Ser Asp Phe Val
    1205                1210                1215

Gln Ile Glu Ser Cys Val Val Thr Tyr Val Asn Leu Thr Arg Asp
    1220                1225                1230

Gln Leu Pro Asp Val Ile Pro Asp Tyr Ile Asp Val Asn Lys Thr
    1235                1240                1245

Leu Asp Glu Ile Leu Ala Ser Leu Pro Asn Arg Thr Gly Pro Ser
    1250                1255                1260

Leu Pro Leu Asp Val Phe Asn Ala Thr Tyr Leu Asn Leu Thr Gly
    1265                1270                1275

Glu Ile Ala Asp Leu Glu Gln Arg Ser Glu Ser Leu Arg Asn Thr
    1280                1285                1290

Thr Glu Glu Leu Gln Ser Leu Ile Tyr Asn Ile Asn Asn Thr Leu
    1295                1300                1305

Val Asp Leu Glu Trp Leu Asn Arg Val Glu Thr Tyr Ile Lys Trp
    1310                1315                1320

Pro Trp Trp Val Trp Leu Ile Ile Phe Ile Val Leu Ile Phe Val
    1325                1330                1335

Val Ser Leu Leu Val Phe Cys Cys Ile Ser Thr Gly Cys Cys Gly
    1340                1345                1350

Cys Cys Gly Cys Cys Cys Ala Cys Phe Ser Gly Cys Cys Arg Gly
    1355                1360                1365

Pro Arg Leu Gln Pro Tyr Glu Val Phe Glu Lys Val His Val Gln
    1370                1375                1380
```

<210> SEQ ID NO 5
<211> LENGTH: 1383
<212> TYPE: PRT
<213> ORGANISM: Artificial Sequence
<220> FEATURE:
<223> OTHER INFORMATION: amino acid sequence of spike protein of PEDV
    strain Br1-87

<400> SEQUENCE: 5

```
Met Arg Ser Leu Ile Tyr Phe Trp Leu Leu Leu Pro Val Leu Pro Thr
1               5                   10                  15

Leu Ser Leu Pro Gln Asp Val Thr Arg Cys Gln Ser Thr Thr Asn Phe
                20                  25                  30

Arg Arg Phe Phe Ser Lys Phe Asn Val Gln Ala Pro Ala Val Val Val
            35                  40                  45

Leu Gly Gly Tyr Leu Pro Ser Met Asn Ser Ser Ser Trp Tyr Cys Gly
        50                  55                  60

Thr Gly Ile Glu Thr Ala Ser Gly Val His Gly Ile Phe Leu Ser Tyr
65                  70                  75                  80

Ile Asp Ser Gly Gln Gly Phe Glu Ile Gly Ile Ser Gln Glu Pro Phe
                85                  90                  95

Asp Pro Ser Gly Tyr Gln Leu Tyr Leu His Lys Ala Thr Asn Gly Asn
            100                 105                 110

Thr Asn Ala Thr Ala Arg Leu Arg Ile Cys Gln Phe Pro Asp Asn Lys
```

115                 120                 125
Thr Leu Gly Pro Thr Val Asn Asp Val Thr Gly Arg Asn Cys Leu
    130                 135                 140
Phe Asn Lys Ala Ile Pro Ala Tyr Met Arg Asp Gly Lys Asp Ile Val
145                 150                 155                 160
Val Gly Ile Thr Trp Asp Asn Asp Arg Val Thr Val Phe Ala Asp Lys
                165                 170                 175
Ile Tyr His Phe Tyr Leu Lys Asn Asp Trp Ser Arg Val Ala Thr Arg
                180                 185                 190
Cys Tyr Asn Arg Arg Ser Cys Ala Met Gln Tyr Val Tyr Thr Pro Thr
                195                 200                 205
Tyr Tyr Met Leu Asn Val Thr Ser Ala Gly Glu Asp Gly Ile Tyr Tyr
    210                 215                 220
Glu Pro Cys Thr Ala Asn Cys Thr Gly Tyr Ala Ala Asn Val Phe Ala
225                 230                 235                 240
Thr Asp Ser Asn Gly His Ile Pro Glu Gly Phe Ser Phe Asn Asn Trp
                245                 250                 255
Phe Leu Leu Ser Asn Asp Ser Thr Leu Leu His Gly Lys Val Val Ser
                260                 265                 270
Asn Gln Pro Leu Leu Val Asn Cys Leu Leu Ala Ile Pro Lys Ile Tyr
                275                 280                 285
Gly Leu Gly Gln Phe Phe Ser Phe Asn His Thr Met Asp Gly Val Cys
    290                 295                 300
Asn Gly Ala Ala Val Asp Arg Ala Pro Glu Ala Leu Arg Phe Asn Ile
305                 310                 315                 320
Asn Asp Thr Ser Val Ile Leu Ala Glu Gly Ser Ile Val Leu His Thr
                325                 330                 335
Ala Leu Gly Thr Asn Leu Ser Phe Val Cys Ser Asn Ser Ser Asp Pro
                340                 345                 350
His Leu Ala Ile Phe Ala Ile Pro Leu Gly Ala Thr Glu Val Pro Tyr
                355                 360                 365
Tyr Cys Phe Leu Lys Val Asp Thr Tyr Asn Ser Thr Val Tyr Lys Phe
    370                 375                 380
Leu Ala Val Leu Pro Ser Thr Val Arg Glu Ile Val Ile Thr Lys Tyr
385                 390                 395                 400
Gly Asp Val Tyr Val Asn Gly Phe Gly Tyr Leu His Leu Gly Leu Leu
                405                 410                 415
Asp Ala Val Thr Ile Tyr Phe Thr Gly His Gly Thr Asp Asp Asp Val
                420                 425                 430
Ser Gly Phe Trp Thr Ile Ala Ser Thr Asn Phe Val Asp Ala Leu Ile
                435                 440                 445
Glu Val Gln Gly Thr Ser Ile Gln Arg Ile Leu Tyr Cys Asp Asp Pro
    450                 455                 460
Val Ser Gln Leu Lys Cys Ser Gln Val Ala Phe Asp Leu Asp Asp Gly
465                 470                 475                 480
Phe Tyr Pro Ile Ser Ser Arg Asn Leu Leu Ser His Glu Gln Pro Ile
                485                 490                 495
Ser Phe Val Thr Leu Pro Ser Phe Asn Asp His Ser Phe Val Asn Ile
                500                 505                 510
Thr Val Ser Ala Ala Phe Gly Gly Leu Ser Ser Ala Asn Leu Val Ala
                515                 520                 525
Ser Asp Thr Thr Ile Asn Gly Phe Ser Ser Phe Cys Val Asp Thr Arg
    530                 535                 540

```
Gln Phe Thr Ile Thr Leu Phe Tyr Asn Val Thr Asn Ser Tyr Gly Tyr
545                 550                 555                 560

Val Ser Lys Ser Gln Asp Ser Asn Cys Pro Phe Thr Leu Gln Ser Val
            565                 570                 575

Asn Asp Tyr Leu Ser Phe Ser Lys Phe Cys Val Ser Thr Ser Leu Leu
            580                 585                 590

Ala Gly Ala Cys Thr Ile Asp Leu Phe Gly Tyr Pro Ala Phe Gly Ser
            595                 600                 605

Gly Val Lys Leu Thr Ser Leu Tyr Phe Gln Phe Thr Lys Gly Glu Leu
            610                 615                 620

Ile Thr Gly Thr Pro Lys Pro Leu Glu Gly Ile Thr Asp Val Ser Phe
625                 630                 635                 640

Met Thr Leu Asp Val Cys Thr Lys Tyr Thr Ile Tyr Gly Phe Lys Gly
            645                 650                 655

Glu Gly Ile Ile Thr Leu Thr Asn Ser Ser Ile Leu Ala Gly Val Tyr
            660                 665                 670

Tyr Thr Ser Asp Ser Gly Gln Leu Leu Ala Phe Lys Asn Val Thr Ser
            675                 680                 685

Gly Ala Val Tyr Ser Val Thr Pro Cys Ser Phe Ser Glu Gln Ala Ala
            690                 695                 700

Tyr Val Asn Asp Asp Ile Val Gly Val Ile Ser Ser Leu Ser Asn Ser
705                 710                 715                 720

Thr Phe Asn Asn Thr Arg Glu Leu Pro Gly Phe Phe Tyr His Ser Asn
                    725                 730                 735

Asp Gly Ser Asn Cys Thr Glu Pro Val Leu Val Tyr Ser Asn Ile Gly
                740                 745                 750

Val Cys Lys Ser Gly Ser Ile Gly Tyr Val Pro Ser Gln Tyr Gly Gln
            755                 760                 765

Val Lys Ile Ala Pro Thr Val Thr Gly Asn Ile Ser Ile Pro Thr Asn
            770                 775                 780

Phe Ser Met Ser Ile Arg Thr Glu Tyr Leu Gln Leu Tyr Asn Thr Pro
785                 790                 795                 800

Val Ser Val Asp Cys Ala Thr Tyr Val Cys Asn Gly Asn Ser Arg Cys
                805                 810                 815

Lys Gln Leu Leu Thr Gln Tyr Thr Ala Ala Cys Lys Thr Ile Glu Ser
            820                 825                 830

Ala Leu Gln Leu Ser Ala Arg Leu Glu Ser Val Glu Val Asn Ser Met
            835                 840                 845

Leu Thr Ile Ser Glu Glu Ala Leu Gln Leu Ala Thr Ile Ser Ser Phe
            850                 855                 860

Asn Gly Asp Gly Tyr Asn Phe Thr Asn Val Leu Gly Ala Ser Val Tyr
865                 870                 875                 880

Asp Pro Ala Ser Gly Arg Val Val Gln Lys Arg Ser Val Ile Glu Asp
            885                 890                 895

Leu Leu Phe Asn Lys Val Val Thr Asn Gly Leu Gly Thr Val Asp Glu
            900                 905                 910

Asp Tyr Lys Arg Cys Ser Asn Gly Arg Ser Val Ala Asp Leu Val Cys
            915                 920                 925

Ala Gln Tyr Tyr Ser Gly Val Met Val Leu Pro Gly Val Val Asp Ala
            930                 935                 940

Glu Lys Leu His Met Tyr Ser Ala Ser Leu Ile Gly Gly Met Ala Leu
945                 950                 955                 960
```

```
Gly Gly Ile Thr Ala Ala Ala Ala Leu Pro Phe Ser Tyr Ala Val Gln
                965                 970                 975

Ala Arg Leu Asn Tyr Leu Ala Leu Gln Thr Asp Val Leu Gln Arg Asn
            980                 985                 990

Gln Gln Leu Leu Ala Glu Ser Phe Asn Ser Ala Ile Gly Asn Ile Thr
        995                 1000                1005

Ser Ala Phe Glu Ser Val Lys Glu Ala Ile Ser Gln Thr Ser Lys
    1010                1015                1020

Gly Leu Asn Thr Val Ala His Ala Leu Thr Lys Val Gln Glu Val
    1025                1030                1035

Val Asn Ser Gln Gly Ser Ala Leu Asn Gln Leu Thr Val Gln Leu
    1040                1045                1050

Gln His Asn Phe Gln Ala Ile Ser Ser Ser Ile Asp Asp Ile Tyr
    1055                1060                1065

Ser Arg Leu Asp Ile Leu Leu Ala Asp Val Gln Val Asp Arg Leu
    1070                1075                1080

Ile Thr Gly Arg Leu Ser Ala Leu Asn Ala Phe Val Ala Gln Thr
    1085                1090                1095

Leu Thr Lys Tyr Thr Glu Val Gln Ala Ser Arg Lys Leu Ala Gln
    1100                1105                1110

Gln Lys Val Asn Glu Cys Val Lys Ser Gln Ser Gln Arg Tyr Gly
    1115                1120                1125

Phe Cys Gly Gly Asp Gly Glu His Ile Phe Ser Leu Val Gln Ala
    1130                1135                1140

Ala Pro Gln Gly Leu Leu Phe Leu His Thr Val Leu Val Pro Gly
    1145                1150                1155

Asp Phe Val Asn Val Leu Ala Ile Ala Gly Leu Cys Val Asn Gly
    1160                1165                1170

Glu Ile Ala Leu Thr Leu Arg Glu Pro Gly Leu Val Leu Phe Thr
    1175                1180                1185

His Glu Leu Gln Thr Tyr Thr Ala Thr Glu Tyr Phe Val Ser Ser
    1190                1195                1200

Arg Arg Met Phe Glu Pro Arg Lys Pro Thr Val Ser Asp Phe Val
    1205                1210                1215

Gln Ile Glu Ser Cys Val Val Thr Tyr Val Asn Leu Thr Ser Asp
    1220                1225                1230

Gln Leu Pro Asp Val Ile Pro Asp Tyr Ile Asp Val Asn Lys Thr
    1235                1240                1245

Leu Asp Glu Ile Leu Ala Ser Leu Pro Asn Arg Thr Gly Pro Ser
    1250                1255                1260

Leu Pro Leu Asp Val Phe Asn Ala Thr Tyr Leu Asn Leu Thr Gly
    1265                1270                1275

Glu Ile Ala Asp Leu Glu Gln Arg Ser Glu Ser Leu Arg Asn Thr
    1280                1285                1290

Thr Glu Glu Leu Arg Ser Leu Ile Asn Asn Ile Asn Asn Thr Leu
    1295                1300                1305

Val Asp Leu Glu Trp Leu Asn Arg Val Glu Thr Tyr Ile Lys Trp
    1310                1315                1320

Pro Trp Trp Val Trp Leu Ile Ile Val Ile Val Leu Ile Phe Val
    1325                1330                1335

Val Ser Leu Leu Val Phe Cys Cys Ile Ser Thr Gly Cys Cys Gly
    1340                1345                1350

Cys Cys Gly Cys Cys Gly Ala Cys Phe Ser Gly Cys Cys Arg Gly
```

-continued

```
              1355                1360                1365

Pro Arg Leu Gln Pro Tyr Glu Ala Phe Glu Lys Val His Val Gln
        1370                1375                1380
```

<210> SEQ ID NO 6
<211> LENGTH: 1383
<212> TYPE: PRT
<213> ORGANISM: Artificial Sequence
<220> FEATURE:
<223> OTHER INFORMATION: amino acid sequence of spike protein of PEDV
      strain CV777

<400> SEQUENCE: 6

```
Met Arg Ser Leu Ile Tyr Phe Trp Leu Leu Leu Pro Val Leu Pro Thr
1               5                   10                  15

Leu Ser Leu Pro Gln Asp Val Thr Arg Cys Gln Ser Thr Thr Asn Phe
            20                  25                  30

Arg Arg Phe Phe Ser Lys Phe Asn Val Gln Ala Pro Ala Val Val Val
        35                  40                  45

Leu Gly Gly Tyr Leu Pro Ser Met Asn Ser Ser Trp Tyr Cys Gly
    50                  55                  60

Thr Gly Ile Glu Thr Ala Ser Gly Val His Gly Ile Phe Leu Ser Tyr
65                  70                  75                  80

Ile Asp Ser Gly Gln Gly Phe Glu Ile Gly Ile Ser Gln Glu Pro Phe
                85                  90                  95

Asp Pro Ser Gly Tyr Gln Leu Tyr Leu His Lys Ala Thr Asn Gly Asn
            100                 105                 110

Thr Asn Ala Ile Ala Arg Leu Arg Ile Cys Gln Phe Pro Asp Asn Lys
        115                 120                 125

Thr Leu Gly Pro Thr Val Asn Asp Val Thr Thr Gly Arg Asn Cys Leu
    130                 135                 140

Phe Asn Lys Ala Ile Pro Ala Tyr Met Arg Asp Gly Lys Asp Ile Val
145                 150                 155                 160

Val Gly Ile Thr Trp Asp Asn Asp Arg Val Thr Val Phe Ala Asp Lys
                165                 170                 175

Ile Tyr His Phe Tyr Leu Lys Asn Asp Trp Ser Arg Val Ala Thr Arg
            180                 185                 190

Cys Tyr Asn Arg Arg Ser Cys Ala Met Gln Tyr Val Tyr Thr Pro Thr
        195                 200                 205

Tyr Tyr Met Leu Asn Val Thr Ser Ala Gly Glu Asp Gly Ile Tyr Tyr
    210                 215                 220

Glu Pro Cys Thr Ala Asn Cys Thr Gly Tyr Ala Ala Asn Val Phe Ala
225                 230                 235                 240

Thr Asp Ser Asn Gly His Ile Pro Glu Gly Phe Ser Phe Asn Asn Trp
                245                 250                 255

Phe Leu Leu Ser Asn Asp Ser Thr Leu Leu His Gly Lys Val Val Ser
            260                 265                 270

Asn Gln Pro Leu Leu Val Asn Cys Leu Leu Ala Ile Pro Lys Ile Tyr
        275                 280                 285

Gly Leu Gly Gln Phe Phe Ser Phe Asn His Thr Met Asp Gly Val Cys
    290                 295                 300

Asn Gly Ala Ala Val Asp Arg Ala Pro Glu Ala Leu Arg Phe Asn Ile
305                 310                 315                 320

Asn Asp Thr Ser Val Ile Leu Ala Glu Gly Ser Ile Val Leu His Thr
                325                 330                 335
```

```
Ala Leu Gly Thr Asn Leu Ser Phe Val Cys Ser Asn Ser Ser Asp Pro
                340                 345                 350

His Leu Ala Ile Phe Ala Ile Pro Leu Gly Ala Thr Glu Val Pro Tyr
            355                 360                 365

Tyr Cys Phe Leu Lys Val Asp Thr Tyr Asn Ser Thr Val Tyr Lys Phe
    370                 375                 380

Leu Ala Val Leu Pro Pro Thr Val Arg Glu Ile Val Ile Thr Lys Tyr
385                 390                 395                 400

Gly Asp Val Tyr Val Asn Gly Phe Gly Tyr Leu His Leu Gly Leu Leu
                405                 410                 415

Asp Ala Val Thr Ile Asn Phe Thr Gly His Gly Thr Asp Asp Asp Val
            420                 425                 430

Ser Gly Phe Trp Thr Ile Ala Ser Thr Asn Phe Val Asp Ala Leu Ile
        435                 440                 445

Glu Val Gln Gly Thr Ser Ile Gln Arg Ile Leu Tyr Cys Asp Asp Pro
            450                 455                 460

Val Ser Gln Leu Lys Cys Ser Gln Val Ala Phe Asp Leu Asp Asp Gly
465                 470                 475                 480

Phe Tyr Pro Ile Ser Ser Arg Asn Leu Leu Ser His Glu Gln Pro Ile
                485                 490                 495

Ser Phe Val Thr Leu Pro Ser Phe Asn Asp His Ser Phe Val Asn Ile
            500                 505                 510

Thr Val Ser Ala Ala Phe Gly Gly Leu Ser Ser Ala Asn Leu Val Ala
        515                 520                 525

Ser Asp Thr Thr Ile Asn Gly Phe Ser Ser Phe Cys Val Asp Thr Arg
    530                 535                 540

Gln Phe Thr Ile Thr Leu Phe Tyr Asn Val Thr Asn Ser Tyr Gly Tyr
545                 550                 555                 560

Val Ser Lys Ser Gln Asp Ser Asn Cys Pro Phe Thr Leu Gln Ser Val
                565                 570                 575

Asn Asp Tyr Leu Ser Phe Ser Lys Phe Cys Val Ser Thr Ser Leu Leu
            580                 585                 590

Ala Gly Ala Cys Thr Ile Asp Leu Phe Gly Tyr Pro Ala Phe Gly Ser
        595                 600                 605

Gly Val Lys Leu Thr Ser Leu Tyr Phe Gln Phe Thr Lys Gly Glu Leu
    610                 615                 620

Ile Thr Gly Thr Pro Lys Pro Leu Glu Gly Ile Thr Asp Val Ser Phe
625                 630                 635                 640

Met Thr Leu Asp Val Cys Thr Lys Tyr Thr Ile Tyr Gly Phe Lys Gly
                645                 650                 655

Glu Gly Ile Ile Thr Leu Thr Asn Ser Ser Ile Leu Ala Gly Val Tyr
            660                 665                 670

Tyr Thr Ser Asp Ser Gly Gln Leu Leu Ala Phe Lys Asn Val Thr Ser
        675                 680                 685

Gly Ala Val Tyr Ser Val Thr Pro Cys Ser Phe Ser Glu Gln Ala Ala
    690                 695                 700

Tyr Val Asn Asp Asp Ile Val Gly Val Ile Ser Ser Leu Ser Asn Ser
705                 710                 715                 720

Thr Phe Asn Asn Thr Arg Glu Leu Pro Gly Phe Phe Tyr His Ser Asn
                725                 730                 735

Asp Gly Ser Asn Cys Thr Glu Pro Val Leu Val Tyr Ser Asn Ile Gly
            740                 745                 750

Val Cys Lys Ser Gly Ser Ile Gly Tyr Val Pro Ser Gln Tyr Gly Gln
```

```
                755                 760                 765
Val Lys Ile Ala Pro Thr Val Thr Gly Asn Ile Ser Ile Pro Thr Asn
770                 775                 780

Phe Ser Met Ser Ile Arg Thr Glu Tyr Leu Gln Leu Tyr Asn Thr Pro
785                 790                 795                 800

Val Ser Val Asp Cys Ala Thr Tyr Val Cys Asn Gly Asn Ser Arg Cys
                805                 810                 815

Lys Gln Leu Leu Thr Gln Tyr Thr Ala Ala Cys Lys Thr Ile Glu Ser
            820                 825                 830

Ala Leu Gln Leu Ser Ala Arg Leu Glu Ser Val Glu Val Asn Ser Met
        835                 840                 845

Leu Thr Ile Ser Glu Glu Ala Leu Gln Leu Ala Thr Ile Ser Ser Phe
    850                 855                 860

Asn Gly Asp Gly Tyr Asn Phe Thr Asn Val Leu Gly Ala Ser Val Tyr
865                 870                 875                 880

Asp Pro Ala Ser Gly Arg Val Val Gln Lys Arg Ser Val Ile Glu Asp
                885                 890                 895

Leu Leu Phe Asn Lys Val Val Thr Asn Gly Leu Gly Thr Val Asp Glu
            900                 905                 910

Asp Tyr Lys Arg Cys Ser Asn Gly Arg Ser Val Ala Asp Leu Val Cys
        915                 920                 925

Ala Gln Tyr Tyr Ser Gly Val Met Val Leu Pro Gly Val Val Asp Ala
    930                 935                 940

Glu Lys Leu His Met Tyr Ser Ala Ser Leu Ile Gly Gly Met Ala Leu
945                 950                 955                 960

Gly Gly Ile Thr Ala Ala Ala Ala Leu Pro Phe Ser Tyr Ala Val Gln
                965                 970                 975

Ala Arg Leu Asn Tyr Leu Ala Leu Gln Thr Asp Val Leu Gln Arg Asn
            980                 985                 990

Gln Gln Leu Leu Ala Glu Ser Phe Asn Ser Ala Ile Gly Asn Ile Thr
        995                 1000                1005

Ser Ala Phe Glu Ser Val Lys Glu Ala Ile Ser Gln Thr Ser Lys
    1010                1015                1020

Gly Leu Asn Thr Val Ala His Ala Leu Thr Lys Val Gln Glu Val
    1025                1030                1035

Val Asn Ser Gln Gly Ser Ala Leu Asn Gln Leu Thr Val Gln Leu
    1040                1045                1050

Gln His Asn Phe Gln Ala Ile Ser Ser Ser Ile Asp Asp Ile Tyr
    1055                1060                1065

Ser Arg Leu Asp Ile Leu Ser Ala Asp Val Gln Val Asp Arg Leu
    1070                1075                1080

Ile Thr Gly Arg Leu Ser Ala Leu Asn Ala Phe Val Ala Gln Thr
    1085                1090                1095

Leu Thr Lys Tyr Thr Glu Val Gln Ala Ser Arg Lys Leu Ala Gln
    1100                1105                1110

Gln Lys Val Asn Glu Cys Val Lys Ser Gln Ser Gln Arg Tyr Gly
    1115                1120                1125

Phe Cys Gly Gly Asp Gly Glu His Ile Phe Ser Leu Val Gln Ala
    1130                1135                1140

Ala Pro Gln Gly Leu Leu Phe Leu His Thr Val Leu Val Pro Gly
    1145                1150                1155

Asp Phe Val Asn Val Leu Ala Ile Ala Gly Leu Cys Val Asn Gly
    1160                1165                1170
```

-continued

| | | | | | | | | | | |
|---|---|---|---|---|---|---|---|---|---|---|
|Glu|Ile|Ala|Leu|Thr|Leu|Arg|Glu|Pro|Gly|Leu|Val|Leu|Phe|Thr|
|1175| | | | |1180| | | | |1185| | | | |

His Glu Leu Gln Thr Tyr Thr Ala Thr Glu Tyr Phe Val Ser Ser
    1190            1195                1200

Arg Arg Met Phe Glu Pro Arg Lys Pro Thr Val Ser Asp Phe Val
    1205            1210                1215

Gln Ile Glu Ser Cys Val Val Thr Tyr Val Asn Leu Thr Ser Asp
    1220            1225                1230

Gln Leu Pro Asp Val Ile Pro Asp Tyr Ile Asp Val Asn Lys Thr
    1235            1240                1245

Leu Asp Glu Ile Leu Ala Ser Leu Pro Asn Arg Thr Gly Pro Ser
    1250            1255                1260

Leu Pro Leu Asp Val Phe Asn Ala Thr Tyr Leu Asn Leu Thr Gly
    1265            1270                1275

Glu Ile Ala Asp Leu Glu Gln Arg Ser Glu Ser Leu Arg Asn Thr
    1280            1285                1290

Thr Glu Glu Leu Arg Ser Leu Ile Asn Asn Ile Asn Asn Thr Leu
    1295            1300                1305

Val Asp Leu Glu Trp Leu Asn Arg Val Glu Thr Tyr Ile Lys Trp
    1310            1315                1320

Pro Trp Trp Val Trp Leu Ile Ile Val Ile Val Leu Ile Phe Val
    1325            1330                1335

Val Ser Leu Leu Val Phe Cys Cys Ile Ser Thr Gly Cys Cys Gly
    1340            1345                1350

Cys Cys Gly Cys Cys Gly Ala Cys Phe Ser Gly Cys Cys Arg Gly
    1355            1360                1365

Pro Arg Leu Gln Pro Tyr Glu Ala Phe Glu Lys Val His Val Gln
    1370            1375                1380

<210> SEQ ID NO 7
<211> LENGTH: 28062
<212> TYPE: DNA
<213> ORGANISM: Artificial Sequence
<220> FEATURE:
<223> OTHER INFORMATION: full DNA sequence corresponding to full length
      RNA of seed stock of PEDV virus USA/Colorado/2013, GenBank
      accession KF272920

<400> SEQUENCE: 7
tttttttttt tcaagcagaa gacggcatac gagattggtc agtgactggt tcagacgtgt      60
gctcttccga ttttctatct acggatagtt agctcttttt ctagactctt gtctactcaa     120
ttcaactaaa cgaaattttg tccttccggc cgcatgtcca tgctgctgga agctgacgtg     180
gaatttcatt aggtttgctt aagtagccat cgcaagtgct gtgctgtcct ctagttcctg     240
gttggcgttc cgtcgccttc tacatactag acaaacagcc ttcctccggt tccgtctggg     300
ggttgtgtgg ataactagtt ctgtctagtt tgaaaccagt aactgtcggc tatggctagc     360
aaccatgtta cattggcttt tgccaatgat gcagaaattt cagcttttgg cttttgcact     420
gctagtgaag ccgtctcata ctattctgag gccgccgcta gtggatttat gcaatgccgt     480
ttcgtgtcct tcgatctcgc tgacactgtt gagggattgc ttcccgaaga ctatgtcatg     540
gtggtggtcg gcactaccaa gcttagtgcg tatgtggaca cttttggtag ccgccccaaa     600
aacatttgtg gttggctgtt attttctaac tgtaattact tcctcgaaga gttagagctt     660
acttttggtc gtcgtggtgg taacatcgtg ccagttgacc aatacatgtg tggcgctgac     720

```
ggtaaacctg ttcttcagga atccgaatgg gagtatacag atttctttgc tgactccgaa    780
gacggtcaac tcaacattgc tggtatcact tatgtgaagg cctggattgt agagcgatcg    840
gatgtctctt atgcgagtca gaatttaaca tctattaagt ctattactta ctgttcaacc    900
tatgagcata cttttcctga tggtactgcc atgaaggttg cacgtactcc aaagattaag    960
aagactgttg tcttgtctga gccacttgct actatctaca gggaaattgg ttctcctttt   1020
gtggataatg ggagcgatgc tcgttctatc attaagagac cagtgttcct ccacgctttt   1080
gttaagtgta agtgtggtag ttatcattgg actgttggtg attggacttc ctatgtctcc   1140
acttgctgtg gctttaagtg taagccagtc cttgtggctt catgctctgc tacgcctggt   1200
tctgttgtgg ttacgcgcgc tggtgctggc actggtgtta agtattacaa caacatgttc   1260
ctgcgccatg tggcagacat tgatgggttg gcattctggc gaattctcaa ggtgcagtcc   1320
aaagacgacc tcgcttgctc tggtaaattc cttgaacacc atgaggaagg tttcacagat   1380
ccttgctact ttttgaatga ctcgagcatt gctactaagc tcaagtttga catccttagt   1440
ggcaagtttt ctgatgaagt caaacaagct atctttgctg tcatgttgt tgttggcagc   1500
gcgctcgttg acattgttga cgatgcactg gacagcctt ggtttatacg taagcttggt   1560
gaccttgcaa gtgcagcttg ggagcagctt aaggctgtcg ttagaggcct taacctcctg   1620
tctgatgagg tcgtgctctt tggcaaaaga cttagctgtg ccactcttag tatcgttaac   1680
ggtgtttttg agttcatcgc cgaagtgcct gagaagttgg ctgcggctgt tacagttttt   1740
gtcaacttct tgaatgagct ttttgagtct gcctgtgact gcttaaaggt cggaggtaaa   1800
acctttaaca aggttggctc ttatgttctt tttgacaacg cattggttaa gcttgtcaag   1860
gcaaaagttc gcggcccacg acaggcaggt gtttgtgaag ttcgttacac aagccttgtt   1920
attgggagta ctaccaaggt ggtttccaag cgcgttgaaa atgccaatgt gaatctcgtc   1980
gtcgttgacg aggatgtgac cctcaacacc actggtcgta cagttgttgt tgacggactt   2040
gcattcttcg agagtgacgg ttttacagaa atcttgctga atgctgacgt tgtcattgaa   2100
catcctgttt ataagtctgc ttgtgagctc aagccagttt ttgagtgtga cccaatacct   2160
gattttccta tgcctgtggc cgctagtgtt gcagagcttt tgtgtcaaac tgatctgttg   2220
cttaaaaatt acaacactcc ttataaaact tacagctgcg ttgtgagagg tgataagtgt   2280
tgtatcactt gcaccttaca tttcacagca ccaagttata tggaggctgc tgctaatttt   2340
gtagacctct gtaccaagaa cattggtact gctggttttc atgagttta cattacggcc   2400
catgaacaac aggatctgca agggttcgta accacttgtt gcacgatgtc aggttttgag   2460
tgttttatgc ctataatccc acagtgtcca gcagtgcttg aagagattga tggtggtagc   2520
atctggcgtt cttttatcac tggtcttaat acaatgtggg attttgcaa gcatcttaaa   2580
gtcagctttg gactagatgg cattgttgtc actgtagcac gcaaatttaa acgacttggt   2640
gctctcttgg cagaaatgta taacacttac ctttcaactg tggtggaaaa cttggtactg   2700
gccggtgtta gcttcaagta ttatgccacc agtgtcccaa aaattgtttt gggctgttgt   2760
tttcacagtg ttaaaagtgt tcttgcaagt gccttccaga ttcctgtcca ggcaggcgtt   2820
gagaagttta aagtcttcct taactgtgtt caccctgttg taccacgtgt cattgaaact   2880
tcttttgtgg aattagaaga acgacatttt aaaccaccag cactcaatgg tagtattgct   2940
attgttgatg gctttgcttt ctattatgat ggaacactat actatcccac cgatggtaat   3000
agcgttgttc ctatctgctt taagaagaaa ggtggtggtg atgtcaaatt ctctgatgaa   3060
gtctctgtta aaaccattga cccagtttat aaggtctccc ttgaatttga gttcgagtct   3120
```

```
gagactatta tggctgtgct taataaggct gttggtaatt gtatcaaggt tacaggtggt    3180
tgggacgatg ttgttgagta tatcaatgtt gccattgagg ttcttaaaga tcacatcgat    3240
gtgcctaagt actacatcta tgatgaggaa ggtggcaccg atcctaatct gcccgtaatg    3300
gtttctcagt ggccgttgaa tgatgacacg atctcacagg atctgcttga tgttgaagtt    3360
gttactgatg cgccagttga tttcgagggt gatgaagtag actcctctga ccctgataag    3420
gtggcagacg tggctaactc tgagcctgag gatgacggtc ttaatgtagc tcctgaaaca    3480
aatgtagagt ctgaagttga ggaagttgcc gcaaccttgt cctttattaa agatacacct    3540
tccacagtta ctaaggatcc ttttgctttt gactttgcaa gctatggagg acttaaggtt    3600
ttaagacaat ctcataacaa ctgctgggtt acttctacct tggtgcagct acaattgctt    3660
ggcatcgttg atgaccctgc aatggagctt tttagtgctg gtagagttgg tccaatggtt    3720
cgcaaatgct atgagtcaca aaaggctatc ttgggatctt tgggtgatgt gtcggcttgc    3780
ctagagtctc tgactaagga cctacacaca cttaagatta cctgttctgt agtctgtggt    3840
tgtggtactg gtgaacgtat ctatgatggt tgtgcttttc gtatgacgcc aactttggaa    3900
ccgttcccat atggtgcttg tgctcagtgt gctcaagttt tgatgcacac ttttaaaagt    3960
attgttggca ccggcatctt ttgtcgagat actactgctc tctccttgga ttctttggtt    4020
gtaaaacctc tttgtgcggc tgcttttata ggcaaggata gtggtcatta tgtcactaac    4080
ttttatgatg ctgctatggc tattgatggt tatggtcgtc atcagataaa gtatgacaca    4140
ctgaacacta tttgtgttaa agacgttaat tggacagcac cttttgtccc agacgttgag    4200
cctgtattgg agcttgttgt caaacctttc tattcttata agaatgttga ttttttaccaa   4260 ggagatttta gtgaccttgt taaacttcca tgtgattttg ttgttaatgc tgcaaatgag    4320
aatttgtctc acggtggcgg catagcaaag gccattgatg tttataccaa gggcatgttg    4380
cagaagtgct cgaatgatta cattaaagca cacggtccca ttaaagttgg acgtggtgtc    4440
atgttggagg cattaggtct taaggtcttt aatgttgttg gtccacgtaa gggtaagcat    4500
gcacctgagc ttcttgttaa ggcttataag tccgttttg ctaattcagg tgttgctctt    4560
acacctttga ttagtgttgg aattttttagt gttccttttgg aagaatcttt atctgctttt    4620
cttgcatgtg ttggtgatcg ccactgtaag tgcttttgtt atagtgacaa agagcgcgag    4680
gcgatcatta attacatgga tggcttggta gatgctattt tcaaagatgc acttgttgat    4740
actactcctg tccaggaaga tgttcaacaa gtttcacaaa accagttttt gcctaatttt    4800 gaaccttttca ggattgaagg tgctcatgct ttctatgagt gcaaccctga aggtttgatg    4860
tcattaggtg ctgacaagct ggtgttgttt acaaattcca atttggattt ttgtagcgtt    4920
ggtaagtgtc ttaacaatgt gactggcggt gcattgcttg aagccataaa tgtatttaaa    4980
aagagtaaca aaacagtgcc tgctggcaac tgtgttactt ttgagtgtgc agatatgatt    5040
tctattacta tggtagtatt gccatctgac ggtgatgcta attatgacaa aaattatgca    5100
cgcgccgtcg tcaaggtatc taagcttaaa ggcaagttat tgcttgctgt tggtgatgcc    5160
atgttgtatt ccaagttgtc ccacctcagc gtgttaggtt tcgtatccac acctgatgat    5220
gtggagcgtt tctacgcaaa taagagtgtg ttattaaag ttactgagga tacacgtagt    5280
gttaagactg ttaaagtaga atccactgtt acttatggac aacaaattgg accttgtctt    5340
gttaatgaca ccgttgtcac agacaacaaa cctgttgttg ctgatgttgt agctaaggtt    5400
gtaccaagtg ctaattggga ttcacattat ggttttgata aggctggtga gttccacatg    5460
```

```
ctagaccata ctgggtttgc cttttcctagt gaagttgtta acggtaggcg tgtgcttaaa    5520
accacagata ataactgttg ggttaatgtt acatgtttac aattacagtt tgctagattt    5580
aggttcaagt cagcaggtct acaggctatg tgggagtcct attgtactgg tgatgttgct    5640
atgtttgtgc attggttgta ctggcttact ggtgttgaca aaggtcagcc tagtgattca    5700
gaaaatgcac ttaacatgtt gtctaagtac attgttcctg ctggttctgt cactattgaa    5760
cgtgtcacgc atgacggttg ttgttgtagt aagcgtgttg tcactgcacc agttgtgaat    5820
gctagcgtgt tgaagcttgg cgtcgaggat ggtctttgtc cacatggtct taactacatt    5880
gacaaagttg ttgtagttaa aggtactaca attgttgtca atgttggaaa acctgtagtg    5940
gcaccatcgc acctctttct taagggtgtt tcctacacaa cattcctaga taatggtaac    6000
ggtgttgccg gccattatac tgtttttgat catgacactg gtatggtgca tgatggagat    6060 gttttttgtac caggtgatct caatgtgtct cctgttacaa atgttgtcgt ctcagagcag    6120
acggctgttg tgattaaaga ccctgtgaag aaagtagagt tagacgctac aaagctgtta    6180
gacactatga attatgcatc ggaaagattc ttttcctttg gtgattttat gtcacgtaat    6240
ttaattacag tgttttttgta catccttagt attttgggtc tctgttttag ggcctttcgt    6300
aagagggatg ttaaagttct agctggtgta ccccaacgta ctggtattat attgcgtaaa    6360
agtgtgcgct ataatgcaaa ggctttgggt gtcttcttca agctaaaact ttattggttc    6420
aaagttcttg gtaagtttag tttgggtatt tatgcattgt atgcattact attcatgaca    6480
atacgcttta cacctatagg tggccctgtt tgtgatgatg ttgttgctgg ttatgctaat    6540
tctagttttg acaagaatga gtattgcaac agtgttattt gtaaggtctg tctctatggg    6600
taccaggaac tttcggactt ctctcacaca caggtagtat ggcaacacct tagagaccca    6660
ttaattggta atgtgatgcc tttcttttat ttggcatttc tggcaatttt tggggggtgtt    6720 tatgtaaagg ctattactct ctattttatt ttccagtatc ttaacatact tggtgtgttt    6780
ttgggcctac aacagtccat ttggtttttg cagcttgtgc cttttgatgt ctttggtgac    6840
gagatcgtcg tcttttttcat cgttacacgc gtattgatgt tccttaagca tgttttcctt    6900
ggctgcgata aggcatcttg tgtggcttgc tctaagagtg ctcgccttaa gcgcgttcct    6960
gtccagacta tttttcaggg tactagcaaa tccttctacg tacatgccaa tggtggttct    7020
aagttctgta agaagcacaa tttctttttgt ttaaattgtg attcttatgg tccaggctgc    7080 actttttatta atgacgtcat tgcaactgaa gttggtaatg ttgtcaaact taatgtgcaa    7140
ccgacaggtc ctgccactat tcttattgac aaggttgaat tcagtaatgg ttttttactat    7200 ctttatagtg gtgacacatt ttggaagtac aactttgaca taacagataa caaatacact    7260
tgcaaagagt cacttaaaaa ttgtagcata atcacagact ttattgtttt taacaataat    7320
ggttccaatg taaatcaggt taagaatgca tgtgtgtatt tttcacagat gctttgtaaa    7380
cctgttaagt tagtggactc agcgttgttg gccagtttgt ctgttgattt tggtgcaagc    7440
ttacatagtg cttttgttag tgtgttgtcg aatagttttg gcaaagacct gtcaagttgt    7500
aatgacatgc aggattgcaa gagcacattg gttttgatg atgtaccatt ggatacccttt    7560 aatgctgctg ttgctgaggc tcatcgttac gatgtcctct tgactgacat gtcgttcaac    7620
aattttacca ccagttatgc aaaaccagag gaaaaacttc ccgtccatga cattgccacg    7680
tgtatgcgtg taggtgccaa gattgttaat cataacgttc ttgtcaagga tagtataccct    7740 gtggtgtggc ttgtacgtga tttcattgcc cttttctgaag aaactaggaa gtacattatt    7800
cgtacgacta aagttaaggg tatatacctc atgttgacct ttaatgattg tcgtatgcat    7860
```

```
actaccatac ctactgtttg cattgcaaat aagaagggtg caggtcttcc tagttttca    7920
aaggttaaga aattcttctg gttttgtgt ctgttcatag ttgctgtttt ctttgcacta    7980
agcttttttg atttagtac tcaggttagc agtgatagtg attatgactt caagtatatt    8040
gagagtggcc agttgaagac ttttgacaat ccacttagtt gtgtgcataa tgtctttagt    8100
aacttcgacc agtggcatga tgccaagttt ggtttcaccc ccgtcaacaa tcctagttgt    8160
cctatagtcg ttggtgtatc agacgaagcg cgcactgttc caggtatccc agcaggtgtt    8220
tatttagctg gtaaaacact tgttttgct attaacacca ttttggtac atctggtttg    8280
tgctttgatg ctagtggcgt tgctgataag ggcgcttgca tttaattc ggcttgcacc     8340
acattatctg gtttgggtgg aactgctgtc tactgttata agaatggtct agttgaaggt    8400
gctaaacttt atagtgagtt ggcacctcat agctactata aatggtaga tggtaatgct    8460
gtgtctttac ctgaaattat ctcacgcggc tttggcatcc gtactatccg tacaaaggct    8520
atgacctact gtcgcgttgg ccagtgtgtg caatctgcag aaggtgtttg ttttggcgcc    8580
gatagattct ttgtctataa tgcagaatct ggttctgact ttgtttgtgg cacagggctc    8640
tttacattgt tgatgaacgt tattagtgtt tttccaaga cagtaccagt aactgtgttg    8700
tctggtcaaa tacttttaa ttgcattatt gcttttgctg ctgttgcggt gtgtttctta    8760
tttacaaagt ttaagcgcat gttcggtgat atgtctgttg gcgttttcac tgtcggtgct    8820
tgtacttgt tgaacaatgt ttcctacatt gtaacacaga acacacttgg catgttgggc    8880
tatgcaactt tgtactttt gtgcactaaa ggtgttagat atatgtggat ttggcatttg    8940
ggatttttga tctcatatat acttattgca ccatggtggg ttttgatggt ttatgccttt    9000
tcagccattt ttgagtttat gcctaacctt tttaagctta aggtttcaac acaactttt    9060
gagggtgaca agttcgtagg ctcttttgaa aatgctgcag caggtacatt tgtgcttgat    9120
atgcatgcct atgagagact tgccaactct atctcaactg aaaaactgcg tcagtatgct    9180
agtacttaca ataagtacaa gtattattca ggcagtgctt cagaggctga ttacaggctt    9240
gcttgttttg cccatttggc caaggctatg atggattatg cttctaatca caacgacacg    9300
ttatacacac cacccactgt gagttacaat tcaactctac aggctggctt gcgtaagatg    9360
gcacaaccat ctggtgttgt tgagaagtgc atagttcgtg tttgctatgg taatatggct    9420
cttaatggcc tatggcttgg tgatactgtt atctgcccac gccatgttat agcgtctagt    9480
actactagca ctatagatta tgactatgcc ctttctgttt tacgcctcca caacttctcc    9540
atttcatctg gtaatgtttt cctaggtgtt gtgggtgtaa ccatgcgagg tgctttgttg    9600
cagataaagg ttaatcaaaa caatgtccac acgcctaagt acacctatcg cacagttaga    9660
ccgggtgaat cttttaatat cttggcgtgc tatgatggtt ctgcagctgg tgtttacggc    9720
gttaacatgc gctctaatta cactattaga ggctcgttca ttaatggcgc ttgtggttca    9780
cctggttata acattaacaa tggtaccgtt gagttttgct atttacacca gcttgaactt    9840
ggttcaggct gtcatgttgg tagcgactta gatggtgtta tgtatggtgg ttatgaggac    9900
caacctactt tgcaagttga aggcgctagt agtctgttta cagagaatgt gttggcattt    9960
ctttatgcag cactcattaa tggttctacc tggtggctta gttcttctag gattgctgta   10020
gacaggttta atgagtgggc tgttcataat ggtatgacaa cagtagttaa tactgattgc   10080
ttttctattc ttgctgctaa gactggtgtt gatgtacaac gtttgttggc ctcaatccag   10140
tctctgcata agaattttgg tggaaagcaa attcttggct atacctcgtt gacagatgag   10200
```

```
tttactacag gtgaagttat acgtcaaatg tatggcgtta atcttcagag tggttatgtt    10260
tcacgcgcct gtagaaatgt cttgctggtt ggttcttttc tgactttctt ttggtcagaa    10320
ttagtttcct acactaagtt cttttgggta atcctggtt atgtcacacc tatgtttgcg     10380
tgtttgtcat tgctgtcctc acttttgatg ttcacactca agcataagac attgtttttc    10440
caggtctttc taatacctgc tctgattgtt acatcttgca ttaatttggc atttgatgtt    10500
gaagtctaca actatttggc agagcatttt gattaccatg tttctctcat gggttttaat    10560
gcacaaggtc ttgttaacat cttttgtctgc tttgttgtta ccatttttaca cggcacatac   10620 acatggcgct ttttttaacac acctgtgagt tctgtcactt atgtggtagc tttgctgact   10680
gcggcatata actattttta cgctagtgac attcttagtt gtgctatgac actatttgct    10740
agtgtgactg gcaactggtt cgttggtgct gtttgttata agctgctgt ttatatggcc     10800 ttgagatttc ctacttttgt ggctattttt ggtgatatta agagtgttat gttctgttac    10860
cttgtgttgg gttatttttac ctgttgcttc tacggtattc tctactggtt caacaggttt    10920
tttaaggtta gtgtaggtgt ctatgactat actgttagtg ctgctgagtt taagtatatg    10980
gttgctaacg gcctacgtgc accaactgga acacttgatt cactacttct gtctgccaaa    11040
ttgattggta ttggtggtga gcggaatatt aagatttctt ccgttcagtc taaactgact    11100
gatattaagt gtagtaacgt tgtgcttttta ggctgtctct ctagcatgaa tgtctcagca    11160
aattcaacag aatgggccta ttgtgttgac ttgcataaca agatcaactt gtgtaatgac    11220
ccagaaaaag cgcaggaaat gctacttgct ttgttggcat tttttccttag taagaatagt    11280 gcttttggtt tagatgactt attggaatcc tattttaatg acaatagtat gttgcagagt    11340
gttgcatcta cttatgtcgg tttgccttct tatgtcattt atgaaaatgc acgccaacag    11400
tatgaagatg ctgttaataa tggttctcca cctcagttgg ttaagcaatt gcgccatgcc    11460
atgaatgtag caaagagcga atttgaccgt gaggcttcta ctcagcgtaa gcttgataga    11520
atggcggaac aggctgcagc acagatgtac aaagaggcac gagcagttaa taggaagtcc    11580
aaagttgtaa gtgctatgca ttcactgctt tttggtatgt tgagacgttt ggacatgtct    11640
tctgtagaca ccattctcaa cttggcaaag gatgggggttg tacctctgtc tgtcataccg    11700
gcagtcagtg ctactaagct taacattgtt acttctgata tcgattctta taatcgtatc    11760
cagcgtgagg gatgtgtcca ctacgctggt accatttgga atataattga tatcaaggac    11820
aatgatggca aggtggtaca cgttaaggag gtaaccgcac agaatgctga gtccctgtca    11880 tggccccttgg tccttgggtg tgagcgtatt gtcaagctcc agaataatga aattattccc    11940
ggtaagctga agcagcgctc cattaaggca gaaggagatg gcatagttgg agaaggtaag    12000
gcactttaca ataatgaggg tggacgtact tttatgtatg ctttcatctc ggacaaaccg    12060
gacctgcgtg tagtcaagtg ggagttcgat ggtggttgta acactattga gctagaacca    12120
ccacgtaagt tcttggtgga ttctcctaat ggtgcacaga tcaagtatct ctactttgtt    12180 cgtaaccttta acacgttacg tagggtgtgct gttctcggct acataggtgc cactgtacgc    12240
ttgcaggctg gtaaacaaac agaacaggct attaactctt cattgttgac actttgcgct    12300
ttcgctgtgg atcctgctaa gacctacatc gatgctgtca aaagtggtca caaccagta    12360 ggtaactgtg ttaagatgtt ggccaatggt tctggtaatg acaagctgt tactaatggt    12420 gtggaggcta gtactaacca ggattcatac ggtggtgcgt ccgtgtgtct atattgtaga    12480
gcacatgttg agcatccatc tatggatggt ttttgcagac tgaaaggcaa gtacgtacag    12540
gttccactag gtacagtgga tcctatacgt tttgtacttg agaatgacgt ttgcaaggtt    12600
```

```
tgtggttgtt ggctggctaa tggctgcact tgtgacagat ccattatgca aagcactgat    12660
atggcttatt taaacgagta cggggctcta gtgcagctcg actagagccc tgtaacggta    12720
ctgatacaca acatgtgtat cgtgcttttg acatctacaa caaggatgtt gcttgtctag    12780
gtaaattcct caaggtgaac tgtgttcgcc tgaagaattt ggataagcat gatgcattct    12840
atgttgtcaa aagatgtacc aagtctgcga tggaacacga gcaatccatc tatagcagac    12900
ttgaaaagtg tggagccgta gccgaacacg atttcttcac ttggaaggat ggtcgtgcca    12960
tctatggtaa cgtttgtaga aaggatctta ccgagtatac tatgatggat ttgtgttacg    13020
ctttacgtaa ctttgatgaa aacaattgcg atgttcttaa gagcatttta attaaggtag    13080
gcgcttgtga ggagtcctac ttcaataata aagtctggtt tgaccctgtt gaaaatgaag    13140
acattcatcg tgtctatgca ttgttaggta ccattgtttc acgtgctatg cttaaatgcg    13200
ttaagttctg tgatgcaatg gttgaacaag gtatagttgg tgttgtcaca ttagataatc    13260
aggatcttaa tggtgatttt tatgattttg gtgattttac ttgtagcatc aagggaatgg    13320
gtatacccat ttgcacatca tattactctt atatgatgcc tgttatgggt atgactaatt    13380
gccttgctag tgagtgtttt gttaagagtg atatatttgg tgaggatttc aagtcatatg    13440
acctgctgga atatgatttc acggagcata agacagcact cttcaacaag tatttcaagt    13500
attggggact gcaataccac cctaactgtg tggactgcag tgatgagcag tgcatagttc    13560
actgtgccaa cttcaatacg ttgttttcca ctactatacc tattacggca tttggacctt    13620
tgtgtcgcaa gtgttggatt gatggtgttc cactggtaac tacagctggt tatcatttta    13680
aacagttagg tatagtttgg aacaatgacc tcaacttaca ctctagcagg ctctctatta    13740
acgaattact ccagttttgt agtgatcctg cattgcttat agcatcatca ccagcccttg    13800
ttgatcagcg tactgtttgc ttttcagttg cagcgctagg tacaggtatg actaaccaga    13860
ctgttaaacc tggccatttc aataaggagt tttatgactt cttacttgag caaggttttct   13920 tttctgaggg ctctgagctt acttttaaagc acttcttctt tgcacagaag ggtgatgcag    13980
ctgttaagga ttttgactac tataggtata atagacctac tgttctggac atttgccaag    14040
ctcgcgtcgt gtatcaaata gtgcaacgct attttgatat ttacgaaggt ggttgtatca    14100
ctgctaaaga ggtggttgtt acaaacctta caagagcgc aggttatcct ttgaacaagt    14160
ttggtaaagc tggtctttac tatgagtctt tatcctatga ggaacaggat gaactttatg    14220
cttatactaa gcgtaacatc ctgcccacta tgacacagct caaccttaaa tatgctataa    14280
gtggcaaaga acgtgcacgc acagtgggtg gtgtttcgct tttgtcaacc atgactactc    14340
ggcagtatca tcagaaacac cttaagtcca tagttaatac tagggcgct tcggttgtta    14400 ttggtactac taagttttat ggtggttggg acaatatgct taagaacctt attgatggtg    14460
ttgaaaatcc gtgtcttatg ggttgggact acccaaagtg cgacagagca ctgcccaata    14520
tgatacgtat gatttcagcc atgatttag gctctaagca caccacatgc tgcagttcca    14580
ctgaccgctt tttcaggttg tgcaatgaat ggctcaagt ccttactgag gttgtttatt    14640
ctaatggagg ttttttatttg aagccaggtg gtactacctc tggtgatgca accaccgcat    14700
atgcaaactc agttttttaat atcttccaag cagtaagtgc caatgttaac aaacttctta    14760
gtgttgacag caatgtctgt cataatttag aagttaagca attgcagcgt aagctttatg    14820
agtgctgtta tagatcaact accgtcgatg accagttcgt cgttgagtat tatggttact    14880
tgcgtaaaca ttttccaatg atgattcttt ctgatgatgg cgttgtttgt tataacaatg    14940
```

```
actatgcatc acttggttat gtcgctgatc ttaacgcatt caaggctgtt ttgtattacc   15000
agaacaatgt cttcatgagc gcctctaaat gttggatcga gcctgacatt aataaaggtc   15060
ctcatgaatt ttgctcgcag catactatgc agattgtcga taaagatggt acttattacc   15120
ttccttaccc tgatccttca agaattctct ctgcaggtgt gtttgttgat gacgttgtta   15180
aaactgatgc agttgtattg cttgaacgtt atgtgtcatt ggctatagat gcctacccgt   15240
tatctaagca tgaaaaccct gaatataaga aggtgtttta tgtgcttttg gattgggtta   15300
agcatctgta caaaactctt aatgctggtg tgttagagtc ttttctgtc acacttttgg    15360 aagattctac tgctaaattc tgggatgaga gcttttatgc caacatgtat gagaaatctg   15420
cagttttaca atctgcaggg ctttgtgttg tttgtggctc tcaaactgtt ttacgttgtg   15480
gtgattgtct acggcgtcct atgctttgta ctaagtgtgc ttatgatcat gtcattggaa   15540
caactcacaa gttcattttg gccatcactc catatgtgtg ttgtgcttca gattgtggtg   15600
tcaatgatgt aactaagctc tacttaggtg gtcttagtta ttggtgtcat gaccacaagc   15660
cacgtcttgc attcccgttg tgctctgctg gtaatgtttt tggcttgtac aaaaattctg   15720
ctaccggctc acccgatgtt gaagacttta atcgcattgc tacatccgat tggactgatg   15780
tttctgacta caggttggca aatgatgtca aggactcatt gcgtctgttt gcagcggaaa   15840
ctatcaaggc caaggaggag agcgttaagt catcctatgc ttgtgcaaca ctacatgagg   15900
ttgtaggacc taaagagttg ttgctcaaat gggaagtcgg cagacccaaa ccacccctta   15960
atagaaattc ggttttcact tgttatcata taacgaagaa caccaaattt caaatcggtg   16020 agttgtgtt tgagaaggca gaatatgata atgatgctgt aacatataaa actaccgcca   16080
caacaaaact tgttcctggc atggttttg tgcttacctc acataatgtt cagccattgc   16140
gcgcaccgac cattgctaat caagaacgtt attccactat acataagttg catcctgctt   16200
ttaacatacc tgaagcttat tctagcttag tgccctatta ccaattgatt ggtaagcaga   16260
agattacaac tattcaggga cctcccggta gtggtaaatc tcactgtgtt atagggctag   16320
gtttgtacta tccaggtgca cgtatagtgt ttacagcttg ttctcatgca gcggtcgatt   16380
cactttgtgt gaaagcttcc actgcttata gcaatgacaa atgttcacgc atcataccac   16440
agcgcgctcg tgttgagtgt tatgatggtt tcaagtctaa taatactagt gctcagtacc   16500 tttctctac tgtcaatgct ttgccagagt gcaatgcgga cattgttgtg gtggatgagg   16560
tctctatgtg cactaattat gacttgtctg tcataaatca gcgcatcagc tataggcatg   16620
tagtctatgt tggtgaccct caacagctgc ctgcaccacg tgttatgatt tcacgtggta   16680
ctttggaacc aaaggactac aacgttgtca ctcaacgcat gtgtgccctt aagcctgatg   16740
ttttcttgca caagtgttat cgctgtcctg ctgagatagt gcgtactgtg tctgagatgg   16800
tctatgaaaa ccaattcatt cctgtgcacc cagatagcaa gcagtgtttt aaaatctttt   16860
gcaagggtaa tgttcaggtt gataatggtt caagcattaa tcgcaggcaa ttggatgttg   16920
tgcgtatgtt tttggctaaa aatcctaggt ggtcaaaggc tgtttttatt tctccttata   16980
acagccagaa ttatgttgcc agccgcatgc taggtctaca aattcagaca gttgactcat   17040
cccagggtag tgagtatgac tatgtcattt acacacaaac ttcagatact gcccatgcct   17100
gtaatgttaa caggtttaat gttgccatca caagggccaa gaaaggcata ttatgtataa   17160
tgtgcgatag gtccctttt gatgtgctta aattctttga gcttaaattg tctgatttgc   17220
aggctaatga gggttgtggt ctttttaaag actgtagcag aggtgatgat ctgttgccac   17280
catctcacgc taacacctc atgtctttag cggacaattt taagactgat caagatcttg   17340
```

```
ctgttcaaat aggtgttaat ggacccatta aatatgagca tgttatctcg tttatgggtt   17400
tccgttttga tatcaacata cccaaccatc atactctctt ttgcacacgc gactttgcca   17460
tgcgcaatgt tagaggttgg ttaggcttttg acgttgaagg agcacatgtt gttggctcta   17520
acgtcggtac aaatgtccca ttgcaattag ggttttctaa cggtgttgat tttgttgtca   17580
gacctgaagg ttgcgttgta acagagtctg gtgactacat taaacccgtc agagctcgtg   17640
ctccaccagg ggaacaattc gcacacctttt tgcctttact aaacgcggc caaccatggg   17700 atgttgtccg caaacgtata gtgcagatgt gtagtgacta cctggccaac ctatcagaca   17760 tactaattttt tgtgttgtgg gctggtggtt tggagttgac aactatgcgt tattttgtca   17820
agattggacc aagtaagagt tgtgattgtg gtaaggttgc tacttgttac aatagtgcgc   17880
tgcatacgta ctgttgtttc aaacatgccc ttggttgtga ttatctgtat aacccatact   17940
gtattgatat acagcagtgg ggatacaagg gatcacttag ccttaaccac catgagcatt   18000
gtaatgtaca tagaaacgag catgtggctt ctggtgatgc cataatgact cgctgtctgg   18060
ccatacatga ttgctttgtc aagaacgttg actggtccat cacataccca tttattggta   18120
atgaggctgt tattaataag agcggccgaa ttgtgcaatc acacactatg cggtcagttc   18180
ttaagttata caatccgaaa gccatatatg atattggcaa tcctaagggc attagatgtg   18240
ccgtaacgga tgctaagtgg ttttgcttttg acaagaatcc tactaattct aatgtcaaga   18300
cattggagta tgactatata acacatggcc aatttgatgg gttgtgcttg ttttggaatt   18360
gcaatgtaga catgtatcca gaattttctg tggtctgtcg ttttgatact cgctgtaggt   18420
caccactcaa cttggagggt tgtaatggtg gttcactgta tgttaataat catgcattcc   18480
atacaccggc ttttgacaag cgtgcttttg ctaagttgaa gccaatgcca ttttctcttt   18540
atgatgatac tgagtgtgac aagttacagg actccataaa ctatgttcct cttagggcta   18600
gtaactgcat tactaaatgt aatgttggtg gtgctgtctg tagtaagcat tgtgctatgt   18660
atcatagcta tgttaatgct tacaacactt ttacgtcggc gggctttact attttgggtgc   18720 ctacttcgtt tgacacctat aatctgtggc agacatttag taacaatttg caaggtcttg   18780
agaacattgc tttcaatgtc gtaaagaaag gatcttttgt tggtgccgaa ggtgaacttc   18840
ctgtagctgt ggttaatgac aaagtgctcg ttagagatgg tactgttgat actcttgttt   18900
ttacaaacaa gacatcacta cccactaacg tagcttttga gttgtatgcc aagcgtaagg   18960
taggactcac cccacccatt acgatcctac gtaacttggg tgtagtttgt acatctaagt   19020
gtgtcatttg ggactatgaa gccgaacgtc cacttactac ttttacaaag gatgtttgta   19080
aatataccga ctttgagggt gacgtctgta cactctttga taacagcatt gttggttcat   19140
tagagcgatt ctccatgacc caaaatgctg tgcttatgtc acttacagct gttaaaaagc   19200
ttactggcat aaagttaact tatggttatc ttaatggtgt cccagttaac acacatgaag   19260
ataaaccttt tacttggtat atttacacta ggaagaacgg caagttcgag gaccatcctg   19320
atggctattt tacccaaggt agaacaaccg ctgatttag ccctcgtagc gacatggaaa   19380
aggacttcct aagtatggat atgggtctgt ttattaacaa gtacggactt gaagattacg   19440
gctttgagca cgttgtgtat ggtgatgttt caaaaccac ccttggtggt ttgcatctac   19500
taatttcgca ggtgcgtctg gcctgtatgg gtgtgctcaa aatagacgag tttgtgtcta   19560
gtaatgatag cacgttaaag tcttgtactg ttacatatgc tgataaccct agtagtaaga   19620 tggttttgtac gtatatggat ctcctgcttg acgattttgt cagcattctt aaatctttgg   19680
```

```
atttgggcgt tgtatctaaa gttcatgaag ttatggtcga ttgtaaaatg tggaggtgga    19740
tgttgtggtg taaggatcat aaactccaga cattttatcc gcaacttcag gccagtgaat    19800
ggaagtgtgg ttattccatg ccttctattt acaagataca acgtatgtgt ttagaacctt    19860
gcaatctcta caactatggt gctggtatta agttacctga tggcattatg tttaacgtag    19920
ttaaatacac acagctttgt caatatctca atagcaccac aatgtgtgta ccccatcaca    19980
tgcgtgtgct acatcttggt gctggctccg acaagggtgt tgcacctggc acggctgtct    20040
tacgacgttg gttgccactg gatgccatta tagttgacaa tgatagtgtg gattacgtta    20100
gcgatgctga ttatagtgtt acaggagatt gctctacctt atacctgtca gataagtttg    20160
atttagttat atctgatatg tatgatggta agattaaaag ttgtgatggg gagaacgtgt    20220
ctaaagaagg cttctttccc tatattaatg gtgtcatcac cgaaaagttg gcacttggtg    20280
gtactgtagc tattaaggtg acggagttta gttggaataa gaagttgtat gaactcattc    20340
agaggtttga gtattggaca atgttctgta ccagtgttaa cacgtcatcg tcagaggcat    20400
tcttaattgg tgttcactat ttaggtgatt ttgcaagtgg cgctgtgatt gacggcaaca    20460
ctatgcatgc caattatatc ttctggcgta attccacaat tatgactatg tcttacaata    20520
gtgtacttga tttaagcaag ttcaattgta agcataaggc tacagttgtc attaatttaa    20580
aagattcatc cattagtgat gttgtgttag gtttgttgaa gaatggtaag ttgctagtgc    20640
gtaataatga cgccatttgt ggttttccta atcatttggt caacgtaaac aaatgaagtc    20700
tttaacctac ttctggttgt tcttaccagt actttcaaca cttagcctac cacaagatgt    20760
caccaggtgc tcagctaaca ctaattttag gcggttcttt tcaaaattta atgttcaggc    20820
gcctgcagtt gttgtactgg gcggttatct acctattggt gaaaaccagg gtgtcaattc    20880
aacttggtac tgtgctggcc aacatccaac tgctagtggc gttcatggta tctttgttag    20940
ccatattaga ggtggtcatg gctttgagat tggcatttcg caagagcctt ttgaccctag    21000
tggttaccag ctttatttac ataaggctac taacggtaac actaatgcta ctgcgcgact    21060
gcgcatttgc cagtttccta gcattaaaac attgggcccc actgctaata atgatgttac    21120
aacaggtcgt aattgcctat ttaacaaagc catcccagct catatgagtg aacatagtgt    21180
tgtcggcata acatgggata atgatcgtgt cactgtcttt tctgacaaga tctattattt    21240 ttatttaaa aatgattggt cccgtgttgc gacaaagtgt tacaacagtg gaggttgtgc    21300
tatgcaatat gtttacgaac ccacctatta catgcttaat gttactagtg ctggtgagga    21360
tggtatttct tatcaaccct gtacagctaa ttgcattggt tatgctgcca atgtatttgc    21420
tactgagccc aatggccaca taccagaagg ttttagtttt aataattggt ttcttttgtc    21480
caatgattcc actttggtgc atggtaaggt ggtttccaac caaccattgt tggtcaattg    21540
tcttttggcc attcctaaga tttatggact aggccaattt ttctccttta tcaaacgat    21600 cgatggtgtt tgtaatggag ctgctgtgca gcgtgcacca gaggctctga ggtttaatat    21660
taatgacatc tctgtcattc ttgctgaagg ctcaattgta cttcatactg ctttaggaac    21720
aaatttttct tttgtttgca gtaattcctc aaatcctcac ttagccacct cgccataccc    21780
tctgggtgct acccaagtac cttattattg ttttttaaa gtggatactt acaactccac    21840 tgttttataaa ttttttggctg ttttacctcc taccgtcagg gaaattgtca tcaccaagta    21900
tggtgatgtt tatgtcaatg ggtttggata cttgcatctc ggtttgttgg atgctgtcac    21960
aattaatttc actggtcatg gcactgacga tgatgtttct ggtttttgga ccatagcatc    22020
gactaatttt gttgatgcac tcatcgaagt tcaaggaacc gccattcagc gtattcttta    22080
```

```
ttgtgatgat cctgttagcc aactcaagtg ttctcaggtt gcttttgacc ttgacgatgg   22140
tttttacact atttcttcta gaaaccttct gagtcatgaa cagccaattt cttttgttac   22200
tctgccatca tttaatgatc attcttttgt taacattact gtatctgctt cctttggtgg   22260
tcatagtggt gccaacctta ttgcatctga cactactatc aatgggttta gttctttctg   22320
tgttgacact agacaattta ccatttcact gttttataac gttacaaaca gttatggtta   22380
tgtgtctaaa tcacaggaca gtaattgccc tttcaccttg caatctgtta atgattacct   22440
gtcttttagc aaattttgtg tttccaccag ccttttggct agtgcctgta ccatagatct   22500
ttttggttac cctgagtttg gtagtggtgt taagtttacg tccctttact ttcaattcac   22560
aaagggtgag ttgattactg gcacgcctaa accacttgaa ggtgtcacgg acgtttcttt   22620
tatgactctg gatgtgtgta ccaagtatac tatctatggc tttaaaggtg agggtatcat   22680
tacccttaca aattctagct ttttggcagg tgtttattac acatctgatt ctggacagtt   22740
gttagccttt aagaatgtca ctagtggtgc tgtttattct gttacgccat gttctttttc   22800
agagcaggct gcatatgttg atgatgatat agtgggtgtt atttctagtt tgtctagctc   22860
cacttttaac agtactaggg agttgcctgg tttcttctac cattctaatg atggctctaa   22920
ttgtacagag cctgtgttgg tgtatagtaa cataggtgtt tgtaaatctg gcagtattgg   22980
ctacgtccca tctcagtctg gccaagtcaa gattgcaccc acggttactg ggaatattag   23040
tattcccacc aactttagta tgagtattag gacagaatat ttacagcttt acaacacgcc   23100
tgttagtgtt gattgtgcca catatgtttg taatggtaac tctcgttgta acaattact   23160 cacccagtac actgcagcat gtaagaccat agagtcagca ttacaactca gcgctaggct   23220
tgagtctgtt gaagttaact ctatgcttac tatttctgat gaggctctac agttagctac   23280
cattagttcg tttaatggtg atggatataa ttttactaat gtgctgggtg tttctgtgta   23340
tgatcctgca cgtggcaggg tggtacaaaa aaggtctttt attgaagacc tgcttttaa    23400 taaagtggtt actaatggcc ttggtactgt tgatgaagac tataagcgct gttctaatgg   23460
tcgctctgtg gcagatctag tctgtgcaca gtattactct ggtgtcatgg tactacctgg   23520
tgttgttgac gctgagaagc ttcacatgta tagtgcgtct ctcatcggtg gtatggtgct   23580
aggaggtttt acttctgcag cggcattgcc ttttagctat gctgttcaag ctagactcaa   23640
ttatcttgct ctacagacgg atgttctaca gcggaaccag caattgcttg ctgagtcttt   23700
taactctgct attggtaata taacttcagc cttttgagagt gttaaagagg ctattagtca   23760
aacttccaag ggtttgaaca ctgtggctca tgcgcttact aaggttcaag aggttgttaa   23820
ctcgcagggt gcagctttga ctcaacttac cgtacagctg caacacaact tccaagccat   23880
ttctagttct attgatgaca tttactctcg actggacatt ctttcagccg atgctcaggt   23940
tgaccgtctc atcaccggca gattatcagc acttaatgct tttgttgctc aaaccctcac   24000
taagtatact gaggttcagg ctagcaggaa gttagcacag caaaaggtta atgagtgcgt   24060
taaatcgcaa tctcagcgtt atggttttg tggtggtgat ggcgagcaca ttttctctct   24120
ggtacaggca gcacctcagg gcctgctgtt tttacataca gtacttgtac cgagtgattt   24180
tgtagatgtt attgccatcg ctggcttatg cgttaacgat gaaattgcct tgactctacg   24240
tgagcctggc ttagtcttgt ttacgcatga acttcaaaat catactgcga cggaatattt   24300
tgtttcatcg cgacgtatgt ttgaacctag aaaacctacc gttagtgatt ttgttcaaat   24360
tgagagttgt gtggtcacct atgtcaattt gactagagac caactaccag atgtaatccc   24420
```

```
agattacatc gatgttaaca aaacacttga tgagatttta gcttctctgc ccaatagaac   24480
tggtccaagt cttcctttag atgtttttaa tgccacttat cttaatctca ctggtgaaat   24540
tgcagattta gagcagcgtt cagagtctct ccgtaatact acagaggagc tccaaagtct   24600
tatatataat atcaacaaca cactagttga ccttgagtgg ctcaaccgag ttgagacata   24660
tatcaagtgg ccgtggtggg tttggttgat tattttcatt gttctcatct ttgttgtgtc   24720
attactagtg ttctgctgca tttccacggg ttgttgtgga tgctgcggct gctgctgtgc   24780
ttgtttctca ggttgttgta ggggtcctag acttcaacct tacgaagttt ttgaaaaggt   24840
ccacgtgcag tgatgtttct tggactttt caatacacga ttgacacagt tgtcaaagat   24900
gtctcaaagt ctgctaactt gtctttggat gctgtccaag agttggagct caatgtagtt   24960
ccaattagac aagcttcaaa tgtgacgggt tttcttttca ccagtgtttt tatctacttc   25020
tttgcactgt ttaaagcgtc ttcttgagg cgcaattata ttatgttggc agcgcgtttt   25080
gctgtcattg tttagatgca actattattt gttgcacact tattggcagg ctttgtttag   25140
tctgctttta ctcctggcgc tataaaaatg cgctctttat tattttttaat actacgacac   25200 tttctttcct caatggtaaa gcagcttatg acggcaaatc cattgtgatt ttagaaggtg   25260
gtgaccatta atcacttttt ggcaactctt ttgttgcttt tgttagtagc atcgacttgt   25320
atctagctat acgtgggcgg caagaagctg acctacagct gttgcgaact gttgagcttc   25380
ttgatggcaa gaagctttat gtcttttcgc aacatcaaat tgttggcatt actaatgctg   25440
catttgactc aattcaacta gacgagtatg ctacaattag tgaatgataa tggtctagta   25500
gttaatgtta tactttggct tttcgtactc ttttcctgc ttattataag cattactttc   25560
gtccaattgg ttaatctgtg cttcacttgt caccggttgt gtaatagcgc agtttacaca   25620
cctatagggc gtttgtatag agtttataag tcttacatgc aaatagaccc cctccctagt   25680
actgttattg acgtataaac gaaatatgtc taacggttct attcccgttg atgaggtgat   25740
tcaacacctt agaaactgga atttcacatg gaatatcata ctgacgatac tacttgtagt   25800
gcttcagtat ggccattaca agtactctgc gttcttgtat ggtgtcaaga tggctattct   25860
atggatactt tggcctcttg tgttagcact gtcacttttt gatgcatggg ctagctttca   25920
ggtcaattgg gtctttttg ctttcagcat ccttatggct tgcatcactc ttatgctgtg   25980
gataatgtac tttgtcaata gcattcggtt gtggcgcagg acacattctt ggtggtcttt   26040
caatcctgaa acagacgcgc ttctcactac ttctgtgatg ggccgacagg tctgcattcc   26100
agtgcttgga gcaccaactg gtgtaacgct aacactcctt agtggtacat tgcttgtaga   26160
gggctataag gttgctactg gcgtacaggt aagtcaatta cctaatttcg tcacagtcgc   26220
caaggccact acaacaattg tctacggacg tgttggtcgt tcagtcaatg cttcatctgg   26280
cactggttgg gctttctatg tccggttcaa acacggcgac tactcagctg tgagtaatcc   26340
gagttcggtt ctcacagata gtgagaaagt gcttcattta gtctaaacag aaactttatg   26400
gcttctgtca gttttcagga tcgtggccgc aaacgggtgc cattatcccct ctatgcccct   26460 cttagggtta ctaatgacaa accccttct aaggtacttg caaataatgc tgtacccact   26520
aataaaggaa ataaggacca gcaaattgga tactggaatg agcaaattcg ctggcgcatg   26580
cgccgtggtg agcgaattga acaaccttcc aattggcatt tctactacct cggaacagga   26640
cctcacgccg acctccgcta taggactcgt actgagggtg ttttctgggt tgctaaagaa   26700
ggcgcaaaga ctgaacccac taacctgggt gtcagaaagg cgtctgaaaa gccaattatt   26760
ccaaatttct ctcaacagct tcccagcgta gttgagattg ttgaacctaa cacacctcct   26820
```

```
acttcacgtg caaattcacg tagcaggagt cgtggtaatg gcaacaacag gtccagatct    26880
ccaagtaaca acagaggcaa taaccagtcc cgcggtaatt cacagaatcg tggaaataac    26940
cagggtcgtg gagcttctca gaacagagga ggcaataata ataacaataa caagtctcgt    27000
aaccagtcca agaacagaaa ccagtcaaat gaccgtggtg gtgtaacatc acgcgatgat    27060
ctggtggctg ctgtcaagga tgcccttaaa tctttgggta ttggcgaaaa ccctgacaag    27120
cttaagcaac agcagaagcc caaacaggaa aggtctgaca gcagcggcaa aaatacacct    27180
aagaagaaca aatccagagc cacttcgaaa gaacgtgacc tcaaagacat cccagagtgg    27240
aggagaattc ccaagggcga aaatagcgta gcagcttgct tcggacccag gggaggcttc    27300
aaaaattttg gagatgcgga atttgtcgaa aaggtgttg atgcctcagg ctatgctcag     27360
atcgccagtt tagcaccaaa tgttgcagca ttgctctttg gtggtaatgt ggctgttcgt    27420
gagctagcgg actcttacga gattacatat aattataaaa tgactgtgcc aaagtctgat    27480
ccaaatgtag agcttcttgt ttcacaggtg gatgcattta aaactgggaa tgcaaaaccc    27540
cagagaaaga aggaaaagaa gaacaagcgt gaaaccacgc agcagctgaa tgaagaggcc    27600
atctacgatg atgtgggtgt gccatctgat gtgactcatg ccaatttgga atgggacaca    27660
gctgttgatg gtggtgacac ggccgttgaa attatcaacg agatcttcga cacaggaaat    27720
taaacaatgt ttgactggct tatcctggct atgtcccagg gtagtgccat tacactgtta    27780
ttactgagtg tttttctagc gacttggctg ctgggctatg gctttgccct ctaactagcg    27840
gtcttggtct tgcacacaac ggtaagccag tggtaatgtc agtgcaagaa ggatattacc    27900
atagcactgt catgagggga acgcagtacc ttttcatcta aaccttgca cgagtaatca     27960 aagatccgct tgacgagcct atatggaaga gcgtgccagg tatttgactc aaggactgtt    28020
agtaactgaa gacctgacgg tgttgatatg gatacacaaa aa                      28062
```

<210> SEQ ID NO 8
<211> LENGTH: 46
<212> TYPE: DNA
<213> ORGANISM: Artificial Sequence
<220> FEATURE:
<223> OTHER INFORMATION: oligonucleotide primer

<400> SEQUENCE: 8

```
atcgaccaca tggctccaac acaccagtcg ttaagcatgg caagct                   46
```

<210> SEQ ID NO 9
<211> LENGTH: 21
<212> TYPE: DNA
<213> ORGANISM: Artificial Sequence
<220> FEATURE:
<223> OTHER INFORMATION: oligonucleotide primer

<400> SEQUENCE: 9

```
cagctcttgc ccatgtagct t                                              21
```

<210> SEQ ID NO 10
<211> LENGTH: 27
<212> TYPE: DNA
<213> ORGANISM: Artificial Sequence
<220> FEATURE:
<223> OTHER INFORMATION: oligonucleotide probe

<400> SEQUENCE: 10

```
cacaccagtc gttaagcatg gcaagct                                        27
```

<210> SEQ ID NO 11
<211> LENGTH: 25406
<212> TYPE: DNA
<213> ORGANISM: Artificial Sequence
<220> FEATURE:
<223> OTHER INFORMATION: full length encoding DNA for PDCoV virus
      USA/Indiana/2014/8501010

<400> SEQUENCE: 11

| | | | | | |
|---|---|---|---|---|---|
| aaaattatag | cattagtcta | taattttatc | tccctagctt | cgctagttct | ctaccgacac | 60 |
| caatccaggt | gcgtctgcca | ccaagttggc | tacccttcct | agggggcgctt | cgcgcttgc | 120 |
| tcaccattag | attacctgga | aaccagccat | tcaggttgga | gtttccccag | gctcttttgt | 180 |
| gtgggcatta | gcggcttgtg | gttttttgcac | aaaatctaag | ctacttaccg | ttcctctgac | 240 |
| catccaccac | ttctatagac | agcactgatt | accgtagggt | ttaagtcaca | ccggtctgca | 300 |
| ccgcccgtca | gcggacacat | tacccagcat | agcactcctt | gcaccgagcc | taggtaggat | 360 |
| aaaacccct | accgggtgac | tcttaaggcg | tttcctccac | gggatagcca | ctagtcacta | 420 |
| ggtgtaagtg | atctgatctg | ggcgtattgt | gttgcgcaag | tgtgataccc | ataggagcgt | 480 |
| ggaatcctat | tctgcggctc | agtgcctgat | atagctgtga | atggccaag | aacaagtcca | 540 |
| agcgcgacgc | tattgcgttg | cctgaaaatg | taccaccacc | tctgcaactt | ttcattcatg | 600 |
| ttgcagctgc | tgaagagggt | caccctaagg | ttactactta | ccttggcaac | tataaccctct | 660 |
| atgccaccaa | ggctccgcct | ggcgtgcagg | ttcttagtgc | taaaacctct | cttactgact | 720 |
| ttgagaatgt | ctttggagct | caacccacct | tgcgatcaat | tcgtaatctg | gtttgtgagg | 780 |
| ctcgctcggc | tgaatggaca | acttccaaga | atgcttttgc | actcaaagcc | actcaacttg | 840 |
| actactctga | tgccgttttg | agggcaatga | ttcgtttctg | ccctccaaag | gtgtccacac | 900 |
| tcgctgcctt | tgctcttttt | ggccgattgg | ttaaaattga | ggacaaggaa | cttgctgagt | 960 |
| tagctcgtga | tactgccctt | gagttggcgt | acacggctaa | aattggtaca | tctcttgctg | 1020 |
| acacgagatc | tgtctcactt | attcataagg | atgcttatct | aactctcagt | aatgaggttg | 1080 |
| ttggcgtaac | ttttactgcc | gcacttatgg | caaaggctac | cactgttaat | ggagcaatgc | 1140 |
| aatactcaaa | cttttacctc | taccctcgtg | ccactattaa | ggtaaccgat | ggtaaggctg | 1200 |
| aagcaattgc | aactaagcct | ctgtctgctg | ccactaaagg | caagcaaatc | acagaggatg | 1260 |
| tcaaccttct | ccctgactat | cagcagctgc | ttgttgatca | agtgactggc | actgaggtta | 1320 |
| aggttggagc | tctaacctat | gttaagacca | ctgattcgcc | acccctttac | tttcccaaag | 1380 |
| tcaagggtgg | tgttattggt | attgcactta | agcagcaggg | cactgcggct | aagaagctca | 1440 |
| atgtagtctt | ccatgctcaa | cctgatgatg | ttctgctagc | cttcatacaa | cttcagcaat | 1500 |
| tcttgaaccg | tacttcggat | tcaagtgttg | aaattactga | ttgccagagt | tatgaagtat | 1560 |
| ctccaactgt | gacggtcaaa | attggcccgt | ctaaacctgg | ggatgtcatc | gtggctactg | 1620 |
| atgaggaata | cctaaatgc | tttgaaaccc | ctgaggtagg | taggctctat | aaggttttcc | 1680 |
| aaactcaatc | ttgggctatc | attgagcgtg | ccttctccag | tttgaagatc | cgcgtgtcca | 1740 |
| aagctttatc | agcatttata | agttttctgc | aaaaccttgc | agataacttt | actgcaataa | 1800 |
| gtggtgttgt | cactgcactc | attcgtgaac | tccaggatct | tacccctggat | gtggcgacac | 1860 |
| gtatcactaa | catacaattt | gtttaccgtg | ccggtaagct | tattgtcgac | acgacaagtg | 1920 |
| tcatagctaa | acttttccag | ccatttttgtg | atttttatatc | acctttccctt | cggaaagttg | 1980 |
| ctggttttgc | aatttacact | gttggtaatc | gcatgcttat | gttaccagc | actggcacct | 2040 |

```
ttcttctcac aaaggcaact actaagatac tcaataaggc aaagtacatc tttgatgtgg    2100
agcctgagta cccagtagat gtaacaacat ccaaagttgt agtacatgaa gcactccagc    2160
aaaccgacac taagcctact agagctctgg aggctgttga tgtcgttgtt ggtaatactg    2220
tactgcaaat ggctactgat ggcactgcgt tctacccatc ggatggtacg cacgcctctc    2280
ttccaggatt caaagcaggt tcggatgagc ttttcataag cttcagctgc gacctctttg    2340
atgatgagac taatgctcaa atcaacgaaa cactcgctgc atatgagctt aaccaactag    2400
tggctccagg tgattctaca ccgcgtcaaa ttgcgacgtt ggttgtcgat acacttgcag    2460
atgctataac agaccacttt ccggagaaaa ccattgatct acctgaagac tatcaagtct    2520
tttctgacca tgatgacctc ccactcgcac aataccacat ccctgatcac ctgagcctgt    2580
atattcaggc tatggaaggt gaagatgata gtggtgatga aatatgtatt gaggacgatg    2640
attacgactg tcctcaagcc gacgaagaca cagaaggagt aattccccaa cagtgggaac    2700
ttcctgatgt tgataaattt ttactcaaga tccaggaacg gaagaccagc agcgacgaag    2760
tacttagcgt cgacgtctat cctaaaccag agccggtcgg caatgttggg attgacgaca    2820
gcgcgtcgga aaagaagcca aatggggact cagtaccgga tcctgaggtc catccaacac    2880
tagagagtgt ggatgttgaa cgaccaaccg aaacagcaaa ccaggctgtt gaagacaaac    2940
cttctgatac cacctttgtg gttgatgagg aacaattaca agaatcaaca ccagaacatg    3000
aactccgctc ctatgaaggg gagtttgatt ctgatgatga aattattatt cctatagtac    3060
cagtaacacc tgcggattta aaaccacaga ctattactat aaaggagtac tttaagtctg    3120
aaaaacttga gactattaac gaaggatcca cagagtcagt tacacaatct gacgattcgt    3180
ttgacgagtc atttgttgat gctgagtctg atgatccaca agatcctgct gtatatgatg    3240
atacaacaat tataacggac agcactgatg taggcgatga gcctgagaca actctagcta    3300
ccatcgttaa cacacctctg acactcgata taacttgcc acctgaagcc attaaacaac    3360
ccagcccaac taaggttgag ttagttgttg gtgaattggc gagtattaaa tttgacaatt    3420
ctgttctagt caaccctgct aatgcgcaat taacaaatgg cggtggagct gctcgtgcaa    3480
ttgcaaaatt agctggtcca aaatatcaag agtactgtaa tagtgtggct cctatctcag    3540
gaccgcttac cacggactct tttgatgcca agaaatttgg tgtagcctgc atcttgcatg    3600
tagtgccacc caaaggttct gaccctaatg tacaagaact cctgtatcaa gcttacaaga    3660
gtatccttac tgaaccagca cactatgtta tacctatact aggtgctggt atctttggat    3720
gcaacccagt ccactctctg gatgcgttca ggaaagcatg tccaagtgac ataggtcgtg    3780
tcacccttgt cactatgaac aaaaaccatt tgcaggtgtg ggatgctctc aataggacca    3840
ttgtacgcac cactactgac tatgatcaag ttaccaccaa ggcccttaca ccccagggag    3900
tgttagaagc caatctcttt gatggtgagg actttgttca agaaccaaaa cccggtcaaa    3960
tctaccttga ggttactgaa gaagttcaga accaagccaa ggaacttgac cttaaccttc    4020
agcaatactg cgtctacctg aagacttgcc accataaatg ggttgtgagt cgtacgaacg    4080
ggttgatgca tctaaaacaa aaagataaca attgttttgt tagtgcaggt gtaaacctgt    4140
ttcaaaacac tgcttatcaa cttagacctg ctattgatgc tctctatagg gagtatctta    4200
atggtaatcc aaatagattt gttgcttgga tctacgcatc cactaaccgt cgtgttggtg    4260
agatgggttg tccacagcaa gttatttctt tgctcgttag taactctgac gcagcatttt    4320
cagcaactac agcctgttgt aacacctact ttaaccacac aggtgttatt tcagtagctc    4380
gtgaatatga cccaatacaa ccaaaggtct actgcatgaa gtgtgatgtg tggactccct    4440
```

```
ttacacccca gagtggaaaa ggtgcagttg caattggtat ttctgcagat gaacctaccg   4500
gtcctgccat taaatttgcc gcagctcact gctggtacac taatggcaag aaaacagtta   4560
atggctatga cactaaagct aatgttgtag ctacctatca taggtttgac gtgcctaagc   4620
ctcaacttgt cgaggacgtg gttgcgctgc ctactaaaaa tgactttgaa gttctcaatg   4680
ttgaagaact gccgcaggat agtgtgctcc atttggaccc acctcctgta caggccttac   4740
aacctaaggc taaccaacac attgagattc tagaaaaccc agattatctg gacattttgg   4800
atctttggat tcgtaaaccc aaaattcatc tcgtaaagtc gtggagtgtt ttgggtagag   4860
cactatgtaa ggcaggtaaa gttgtctttg tcagtgcttc gcttttgacc cgtttctaca   4920
attaccttgt agagattggt gctcttgact caacaataag gttgtcagtc gatcttacct   4980
gtaaatttgt tagaacggtt ctcccatcgt ctaacactgt acacaaaact tgtcttggtc   5040
tgtattattc agcccagaca cttttttgttt ctttagcacc attccttatg ttaccagctg   5100
tagttagtct gcttaattca ggctatacaa ttggcacata tttgtatgca aaaactggct   5160
ggccttgtaa ttacaatgcc acgcaacact ttgattataa ttcttactgt gcaggtgact   5220
tggtttgtca agcctgtttt gacggtcaag actccctaca tttgtatccg catttacgtg   5280
ttaatcagca acccttcag accactgact acactgttta tgcgctttca ctaatactac   5340
tattagctaa catgactctt gtcatgggca cgctaatagt tactttcttt gtgaacttct   5400
atggtgtgca ataccatttt tatggtacac ttttgataga ttatcaatcc gcactggtga   5460
ttactttctc agtgtactac ttttataagg taatgaagtt ttttccgccat ctcacacatg   5520 gatgtaaaat tccaacgtgt gtggtatgtg ccaaacttcg taccccacct actataacag   5580
ttgagactgt cgttcagggc aggaaatacc catctgttat tgaaacaaat ggcgggttta   5640
caatttgtaa agaacacaac ttctattgca aggactgctc tttacaaaca cccggcactt   5700
tcattccgac agaagctatt gagtcgctct cacgagctac caggcttagt gtcaaaccaa   5760
cagcaccagc attcttactt gctagagatg ttgagtgcca aactgatgtt gtcgttgctc   5820
gcgcaatgca taaccaaaat gcgcatgtgt gcatttcaaa atactctgat atccgtaccg   5880
ttgaccaact acttaagcct actccactgt tttcatacac tcccgatgtt atcatcgcgg   5940
cagactttga caacagaggt agtcttaaga cagctaaaga attagctgtg gttttgtcaa   6000
tggaccttaa acgtactata attatcattg atcaggccta ttctagacct attgataatt   6060
atcaggaagt tgcttctcgt attgagaagt attacccagt tgcaaagatc acacccacag   6120
gtgacatctt tacagacatt aagcaagcga ccaatggcca agctagtgac tctgctatta   6180
atgcagctgt tctggctgtc cagcgcggtc ttgattttac aattgacaac cctaacaaca   6240
tattaccaca ttacgccttt gactttcaa ccctcaatgc agaagaccag tctaccattt   6300
tggagagtgg ttgtgctaaa ggcaatctca agggcactaa tgttggtgtt gttctttcag   6360
ctagccttgt tacacgtctt agtcagcagg ctatacgtgt gattgctaat gctgcttcac   6420
gtaatggtgt tacatgtgct gttactcctt ctacacttgt tatgcgtggg aatattgcaa   6480
cacagccctt gactcgcatc aaagctggtg cacctcccat gcgtcaaaaa attttatgtg   6540
ttatcctggc acttgctatt gtgtactttg ctgctatggc ttttgctttt ttggcaagtc   6600
aaattacgct taatacagtg cctacgatta atctgatat ccgcgcctct accttctacg   6660
ttgttagaga tggagtcttg gatactgttc gttcaaatga caagtgcttt gcaaataagt   6720
ttttggcatt tgatagcttc attcaagcac cttcactaa ttcacctgac tgtccagttg   6780
```

```
ttgtgggagt tgttgatgta acgacgcact ctattcctgg aattccagca ggtgtcattc    6840
atagagacgg tctcatactt aacatttatg aacagtctct ttatgaaact catcagcgtc    6900
agtctatggt tagggatgcg ttgtcactca agacagcaaa tctctttaac ctaggcaagc    6960
gtgttgtagt aggatacact caacatgaag ttgttgtggg tacctcctat tttaattctc    7020
ctgcactttt taatgcaaag tgcaccttct tacagtatca ggacactaga caactctatt    7080
gctatgatac tgttcctact gaacataagc tctactctga tgtgcttccg cacgtcgagt    7140
ataaggctat tgacattaat ggtgatcttg ttcctttcaa gataccagag cagataatgt    7200
tctatccaca tattgtgcgc tatactagca attcctattg ccgtatgggg cattgtttta    7260
atactaaccc tggtatttgc atttcattta cggacgaatt tccgtatagt gaaaatgtca    7320
aacctggtgt gtactgtgct gatacctctt tgcagttgtt ttcaaacctc gttttgggca    7380
ctgtatctgg tattcacatc tttacatcaa cagctgcatt gcttggatct actattgtga    7440
tcatactatg cgttgttgct gttcttgcag ttcagcgatt cttcaaggag tacacaactt    7500
ttgttatgta cacttgtggt cttgctcttg tcaacattgt aggcattgca cttatgtaca    7560
agtgccttgt cttcgcgatt ttctattatg caatctacct ttactttgtc cttactttcc    7620
cctcctttaa gaggaatgtg gcattgtttt acttcgctgt agtgatcgtg ccgcacgtga    7680
gtaacatgca attgcttgcg ctcattgtgt gtagcattat ctactttctc tacacctatg    7740
ttcatactgt agctaagaca gctgggaaat tttcttcctt cttagacgca gctaaagcta    7800
cttttgtcat tgacaatgaa aagtacgtgt tgcttaaaga cctcgctggt gctgaatttg    7860
accagtatct ggcctcttac aacaagtaca atattttttc tggtactgct tctgataagg    7920
attatgataa ggtctgtatg gcatttcttg ccaaggcttt gtcatctttt cgtgaaggag    7980
gcggttcaca gttgtacaca ccacctaaat ttgcagttgt tcagagtctt aagaccaagc    8040
tgcaagcagg tatcaaaatc ctcctgcacc cttcaggtgt agttgagcga tgtatggtct    8100
cagttgtcta caatggatct gcattgaatg gcatctggct taagaatgtt gtctactgcc    8160
cacgccatgt aattggaaaa ttccgtggtg accagtggac tcacatggtc tcaattgctg    8220
attgccgcga ctttatagtc aagtgtccaa tacagggtat tcagctaaat gtccaatcag    8280
ttaagatggt aggagctctc ctccagttaa ctgttcatac caacaacaca gccactccag    8340
actataagtt tgaaaggctc caaccaggat catcgatgac aattgcttgt gcttatgatg    8400
gcattgtacg gcatgtctat cacgtggtcc tccaacttaa taatcttatt tatgcaagct    8460
tccttaacgg agcttgtggt agtgtgggtt acactcttaa gggtaaaaca ctctacttac    8520
attacatgca ccacattgag tttaataaca aaactcatag tggtacagat cttgaaggta    8580
acttctatgg cccctatgtg gatgaggaag ttattcagca acaaacagca ttccagtatt    8640
acactgataa tgttgttgct caattatatg cacacttact gactgttgat gctagaccaa    8700
aatggctggc acaatctcag ataagtatcg aggatttcaa ctcatgggct gctaacaatt    8760
cctttgctaa cttcccatgt gaacaaacta atatgtccta cattatggga ctctcgcaaa    8820
cagctcgagt ccctgtagaa cgtatcctca ataccattat acagctaacc accaatagag    8880
atggtgcttg tattatggga tcttatgatt tcgagtgcga ttggacgcca gagatggtat    8940
acaatcaggc tccaatttca ttgcagtcag gagtagttaa gaaaacttgt acgtggttct    9000
tccacttctt gttatggcta attaccatgc tactcgctgc catgcatgtt ttccctgtac    9060
acttgtatcc aatagtactg ccatgcttca ctgtcgtggc attcctgttg acttttaacca   9120
ttaaacacac tgttgtgttt accactacat acttgcttcc gtcacttttg atgatggttg    9180
```

```
taaatgctaa cacttttggg ataccgaaca catttctgcg cacctgctac gaaactatat   9240
tcggttcccc aattgctcag cgactgtatg gttacactgt tgctctttat atgctgatct   9300
atgctggact tgcaatcaac tatacgttga aaacactccg gtatagagca acttcattct   9360 tatcttttg catgcagtgg tttcaatatg gttatgttgc acacattgcg tacaaactgc    9420
ttaataaacc ctggacagaa tcactactct tcacagcctt cacaatgcta accagtcatc   9480
ctttgttggc tgctcttagc tggtggctag ctggtcgcgt aactctgccc attatcatgc   9540
ctgacttagc tattcgtgtt ttggcgtata acgtcattgg ctatgtcata tgtgttcgat   9600
ttggccttat gtggcttgca aatcggttca caactgtacc tatgggcaca taccagtata   9660
tggtgtctgt agagcaactt aagtacatga tggcagttaa gatgtcccca ccgcgtaatg   9720
cgtttgaggt gcttatagcc aacattagac ttcttggttt gggtggaaac cgtaacattg   9780
ctgtttctac tgtccaaaac aaaattcttg atgcaaaagc tactgctgtt gttgttgcta   9840
accttcttga aaaggctggc gtcacaaaca agcacgctat ttgcaaaaag attgtgaaac   9900
tccacaatga taccctaaaa gccaccactt atgaggaggt tgaggtagca cttgtgaaac   9960
ttctttctca cataattgag ttcttgccaa ctgatcaggt agatgctat ctagctgatg   10020 cggccaatgc tcaacatgtt aatacctatt tgacaacttg cttgagaac aaagctgttg    10080 ttcaggctgt tgccgatatc aacattaatc tggattctta tagaatttat aaggaggcag   10140 atgctatta taaacgatct gttgagatga acgaatctcc gcaggagcaa aagaaaaagc    10200
ttaaagctgt taacattgca aaggcggaat gggagcgtga ggctgcttct cagcgtaagc   10260
ttgaaaagct tgctgatgct gctatgaagt ctatgtatct tgcagaacgt gctgaggatc   10320
gtcgcattaa gctaacctct ggacttactg caatgcttta ccatatgctt agacgtcttg   10380
actcagatag ggtaaagct ctgtttgagt gcgctaaggc acaaatcttg ccaatacatg     10440
ctgtagtcgg aatttctaat gacaaccta aagttatttt taacgataag gacagctact    10500
ctcattatgt agagggcaac acacttatac ataagggagt tcgctacact attgtgaaga   10560
aactctcctt agataatgca cctattgaag gcgtaccaga agaattccct gtggtcgttg   10620
agactgttag ggaaggtgtg ccccagttgc aaaataatga gctatgtttg cgcaatgttt   10680
tcactgctca gaacacagct caggacttca atggcaatga atccactgta aaatcttttt   10740
atgttactag aaccggtaag aagattttgg ttgccattac atcaactaaa gacaatctta   10800
agactgtgac ctgccttact gagaccggta agacagtcct taacttggac cccctatgc    10860 gcttcgcaca taccgtaggt ggaaaacagt ctgttgtcta tctctatttt atcagaata   10920 ttagttcact caacagaggt atggttattg ccacatctc tgaaactact atccttcagg   10980
caagtggcac tcaaattgag taccagcaaa atgcctctct ttgacctat ttggctttcg    11040 ctgtagaccc taagacagcc taccttaagc atcttgctga tggtgggtct cctatacagg   11100
gttgtattca gatgattgct actatgggtc ctggattgc agttactact aaaccacaac    11160
ctaatgagca tcagtattct tatggtggtg cttcaatttg tctttattgc cgtgctcata   11220
taccacatcc tggtgttgat ggacggtgcc cctacaaagg ccgctttgtt cacatcgaca   11280
aagataagga acctgtttcc ttcgccttga ctcatgagca atgcagttct tgtcaacggt   11340
gggttaatta tgactgcacc tgcggatcta gtctgcagaa ttcggcttat ttaaacgagt   11400
aacgggttct agtgacgccc ggctagaacc cctgcagcct ggaactcaac cagatgctgt   11460
aaaaagggcc ttccatgtgc ataatgatac cacctctggt atattcttaa gcacaaaatc   11520
```

```
taactgcgct cggtttaaaa ccacacgcag tgccctgcct ttacctaata agggagaggt  11580
tgaattgtac tttgttacta agcagtgtgc agctaaagtc ttcgaaatcg aggaggaatg  11640
ctacaacgct cttagtacag agctttatac tactgatgat acatttggtg tccttgccaa  11700
aactgagttc tttaagtttg acaagatacc taatgtcaat cgccagtatc tgactaaata  11760
tacactcctg gacttggctt atgctctacg tcatttgtca acatctaagg atgttattca  11820
agaaatcttg atcaccatgt gcggaacccc tgaagattgg tttggggaaa attggtttga  11880
tccaattgag aacccatcct tttacaagga gttccataaa cttggggata ttcttaaccg  11940
ttgtgttctt aatgccaata agtttgctag tgcctgtata gacgctggtc ttgttggcat  12000
attaacaccc gacaaccaag acctcctggg tcagatctat gactttggag atttttattat  12060 tacacaacca ggtaatggat gtgtggactt agcatcctat tattcttatt taatgcccat  12120
tatgtccatg actcacatgt taaagtgtga gtgtatggat agtgatggca acccacttga  12180
gtatgatgga tttcagtatg acttcacgga cttcaagctt ggcttgttcg agaagtattt  12240
taagtactgg gaccgtcctt accatcctaa cactgttgaa tgtccagatg accgttgcgt  12300
attgcactgt gcgaacttca atgtgttgtt tgctatgtgt atacctaata cggcatttgg  12360
caatctttgt tcaagagcta ctgttgatgg ccaccttgtg gtccagacag tgggtgtaca  12420
cttgaaagaa ctcggtatag tccttaacca ggacgttacc acacacatgg caaatattaa  12480
tctaaacact ctattgcgat tggttggtga tcccaccact attgcaagtg tctcagacaa  12540
gtgtgtagat ttaagaactc cttgtcagac cttggctact atgtctagcg aattgctaa  12600 acagtcagtc aagcccgggc attttaatca acacttctac aagcatttgc ttgatagtaa  12660
cctattagac caacttggaa tagacattcg ccacttctac tatatgcagg atggtgaagc  12720
ggctatcaca gactacagct actacaggta taatacccc acgatggtag atatcaagat  12780 gttcttatttt tgccttgagg tggcagataa gtatcttgag ccctacgaag gtggatgtat  12840
taatgcacag tcagttgtgg tctctaattt ggacaagtca gcgggctacc cctttaacaa  12900
gctaggtaag gctcgtaact attacgacat gactcatgcc gagcaaaatc aactgtttga  12960
gtatacaaaa cgcaatgttt tgcctacact cactcagatg aaccttaagt atgcaatttc  13020
agccaaggat cgtgctcgca ctgtggcagg agtgtctata attagcacca tgactaacag  13080
gcagtaccat caaaagatgc tgaaatctat ttcacttgca cgcaatcaga ccatcgtgat  13140
tggaacaacc aaattctatg gtggttggga acatatgtta cgacgactga tgtgtaatat  13200
caacaatccc attttagtgg gttgggatta ccctaagtgt gatcgttcta tgccaaacat  13260
gctgcgcatt gccgcttcgt gcttgctagc acgaaaacac acttgctgta accaaagcca  13320
gcgattctac cgtttggcta atgaatgttg ccaagtacta tctgaagtgg tagtctctgg  13380 taacaaccctc tatgtaaaac caggtggcac tagcagtggt gatgcaacca cagcttatgc  13440
caactcggta tttaacatct acaggtggt ttctgctaat gtagccacct tcttatcaac  13500
ttccaccacg acacatctta ataaggacat tgcggacttg catcgtagtc tttatgaaga  13560
tatttatcgt ggtgactcta atgatatcac cgtcatcaat agattctacc agcatctcca  13620
aagttacttt ggactatga tattgtctga tgatggtgtc gcatgcatag actcagccgt  13680
tgcaaaggct ggagctgttg ctgatcttga tggtttccga acattttgt tttaccaaaa  13740 caatgtttac atggcagact caaagtgttg gacagaaact gacatgaatg ttggccctca  13800
tgaattttgc tcacagcata ctgtgttagc agagcatgat ggtaaacctt actacttacc  13860
ttacccagat gtctctcgca ttctgggtgc atgtatcttt gtggatgacg ttaacaaggc  13920
```

```
tgaccctgtt cagaaccttg aacgttacat ctcacttgca attgatgcat atcccttac   13980 caaggttgac cctattaagg gtaaagtctt ttatttgtta ctagactaca tacgtgttct   14040
tgctcaggag ttacaggacg gtatccttga tgctttccaa tcactcactg acatgtcgta   14100
tgtaaataac tttatgaatg aggccttta tgctcagatg tatgagcaaa gtcctacact   14160
acaggccagc ggtgtttgtg tggtgtgtaa ttcacccact atactgcgct gtggtgattg   14220
cattcgtcga ccactacttt gttgcgtctg tgcctaccag catgttacgc agactacaca   14280
taaacgtatc attgctatca acaactacat ctgtagtgtt gagaattgca atgaggacaa   14340
tgttgaaaaa cttttcattt ctggcactgc gatttattgt gagaatcaca acccacgct   14400 gtgcataccc attgtagcta atggttctgt ttttggtatc tatcgccaca ctgcccgtgg   14460
tagtgatgac atagacctct ttaacgagct tgctacatct aactatgaca ctattgaacc   14520
ttatcagaag gccaatcgtg caccttttatc acttatgctc ttcgctgctg aaaccattaa   14580
ggcactcgag gagtctatca agaagtcata tgctaccgca accgtcaagg atgtgtatga   14640
ccaacgcttc attaaacttc tatgggaaca gggtaaaaag ccgccaccca taacgaagaa   14700 ccacatttc actggctacc attttaacaa gaatggaaaa acccaagttg gtgattacat   14760
tcttgctaaa acagatggca gtgacactta cttacaga ggaacatcta cctacaaact   14820
ccaaacaggt gatgttctag tcttaatggc acatgttgtt acaccgctct cagcacccc   14880 tgtgctaacg cagacaacat atgtcagaaa atcactttta cccgactctg ttggtgcgtc   14940
ttattatgtg caacattta agtcatataa tgagatagct atgcagaggg ttacaacagt   15000
attaggtcca ccaggcacag gtaagtcaac ctttgctatt ggtttggcta agtactttcc   15060
cagtgcacgt atttgctaca ctgcgtcttc gcatgcagca atcgatgcac tctgtgaaaa   15120
agctttcaag acaatacctg taggccaatg cagtcgtatc gtacccacac gtacaactgt   15180
tgagtgcttt caggagtttg tcgtaaataa cacaactgca cagtatatct ctcgactat   15240 caatgcctta cctgacatta agtgtgacat tgtagttgta gatgaggttt ctatgttgac   15300
caattatgag ctttcctctg tgaatgctcg tttggtttac aatcacattg tgtatgttgg   15360
tgatccttat cagttacctt cacctagaac tatgcttacg tctggccagc tttcgccagc   15420
tgactataac gtagttactg atataatggt acatgcagga gcggatgtta tgctcgacat   15480
gtgctacaga tgcccacgtg aaatcgttga cacagtgtct aaacttgtct acgataacaa   15540
actaaaagcg gcgaaaccga actcaagaca gtgttacaag accattgtga actttggtcc   15600
tggagacgtt gctcatgagg acaatctgc ctacaacgaa gcacagttgc gtttcgcact   15660
cgcatttaga caacaaaagc ggtgggataa cgtgactttc atatctccat ataatgctat   15720
gaatgtgaaa gcatccttag caggtttctc tactcagacc gttgactctt ctcaaggttc   15780
tgagtatgat tatgttatct tttgcgtgac cactgattca gcacacgcac ttaacatggc   15840
tcgtttgaac gttgcctta cacgcgcaaa gataggtatc cttgtggtgt ttaggcaggc   15900
aaacgaactt tacaatagtt tgcagtttga atctattgat tcacagcttc agtcgagtgc   15960
tgagaaaaac ctcacaccac tgtttaagcg ctgcggctat gagtataatg gcgtccatcc   16020
agctcatgct ttgacctggc atgattgtgg tgcagagtac cgctgtgagg agccacttgc   16080
taaattagta ggagttgccg atggcactct tatatcatac aaaaccctag tatccacact   16140
tgggtttctt ccatcactta aaattgatgc atatcataat atgttcctaa cacgtgacgc   16200
gtgtcgcacc tatgttcaga gttggatcgg catagatgtt gaagcagcac acgccataaa   16260
```

```
acctaacacc gggactaacc tgccattgca aataggtttt agtaccggaa agaattttc   16320
agtcactcca gagggaattt gggtaaacga gcacggatct tgcactgagc ccgtccctgc   16380
caaaatacct cctggagaac aatttcgtca ccttaaaaag gacatgcgcc aggcgcgtcc   16440
ttggaaggtt gttcgacgtg agattgctac tcacattgct gaggtagctc ctcacactga   16500
ttatatatgc tttgtcactt gggctcacca gcttgagcta gcgacaatgc gctactttgt   16560
caaactaggt atgaagagaa aatgcttttg tggcaggcgg gcttgtttca ctaatggaac   16620
tgagttcgct tgcaaagcac accattctct caccattcca caatgtgatt atgtgtacaa   16680
tccattcctc atcgacgtgg ctacgtgggg attctcggga cggctttcca ccaaccatga   16740
cgctgtgtgc acatatcatg ctaatgccca tgttgcatca gctgatgcaa tcatgacggt   16800
atgtttagct atccatgaac tgttcagtac tgttgactgg aactttgaat tccagtaac   16860
tgctgagcaa tcgcaactta caaggcctg tcgcttagta caggcgaatt acttaaatat   16920
actactcact acaaccaaag ccacggtggt tcacgatatt ggtaacccaa aaggtatccc   16980
tatcgtgcgc aaacctggtg ttaaatatca cttctatgat caagcaccca ttgtcaaaca   17040
cgttcaaaaa ctaaagtaca agccagagat ggaggcccgt ttcaccgatg gtttgactat   17100
gttttggaat tgtaatgttg acacataccc tgctaacgcc cttgtgtgcc gctacgcac   17160
tcatcggcag aagcatttaa ttggacctaa tggttcagca ctatatgtta ataagcatgc   17220
ttttctcacc cctgagatgc atacttatgc tacacataaa ctcaacttgg ctccactcat   17280
ctactactcc accacagatt gtagtagtga acagcctatt gttgttacct acagagattg   17340
tgtcacccgg tgcaatactg gaaaaactct ctgtccaaat catgctcttg aataccaaga   17400
gtttatcaat gcatacaatc tcatggctcg ccatggattt aatgtttaca taccacgcaa   17460
tgtcaacgtt tacaactgtt ggcttacttt cactaatctc caaaaccttg aaaacttagc   17520
ttacaactgt tattataaga actgcaatgc tcacgttgat gggcagcttg atgtagttat   17580
taataataac gctgtatatg ctaaggtcga caataatctt gtcaaacttt tcgcaaccg   17640
cactaactta cctgtctcag tggcctttga acattacact aacaggcata cccgttcact   17700
gccaactaca cagctgttat ctggtttagg cgtaaccgcc accagaaatt tcactgtgtg   17760
gttcgacaat gatacaattt ccaatacac tattaatgta tctacgtata ctgacatcga   17820
ccctagtacc catgttgtcc tctgtgatga taggtacgga acagattgga gtcagtttaa   17880
ccaacttcct aatgcagtat tcctcaccaa aactaaggtg aagaaaacag aaccgtttgt   17940
ttgtacagca ctgaccctaa atggcgtcgc cattgacggt gaagagctat acatctatgt   18000
acgctataac aatcaactga ccacatttgc tactacttgt acacagggta gaaatgttga   18060
gcagtttata cctaaaacac ctatggaaag agacttcctt gagatgtctc aacagtcctt   18120
catccagcaa catcaattgc aggaactggg tgttgaacac attatctatg gtgatgattc   18180
cagtccagtc attggcggaa ctcacacact tatctcacta gttaaaaaca gtttgaaca   18240
tcagcttgtc aaccatgttt acaacccagt ccagaactgt gttgttacct cacctaacgc   18300
aagctccaag aacgtttgca ctgttcttga tgttcttctt gatgactaca ttgacatcat   18360
aagacaagca catgccagtt acacaagtaa atccaaagta ttcactgtgt caattgacaa   18420
ccaacaaatt agattcatgc tttggcatga tgagcaagtt aagacttgct acccaatctt   18480
acagtcactt accaatggtt accagatgcc atctgtgtac aaaacattgg ttactgactt   18540
acaacctgct gacatccctta attatcattc ctacacccc cgggtgcctg gagtagtaa   18600
gaatgttatc aagtaccgcc aacttttcaa ctacatagtt aaaaggata ggttggcagt   18660
```

```
accacacaat atgaccgtat tacaccttgg agctgcatct gcactaggta cagcaccagg   18720
ttcttcagtc ataaaacaaa tgtttcctga aggaactgtt cttattgacc tcgatataag   18780
agagttcact tcagatgcta accaaataat agttacagac tacagaactt acataccacc   18840
acaccacgta gacgtcatat tttctgacct ctactgttgt gatgacatac acttctttga   18900
caatctaata aggatagtta aggagaggct cgccctcggt ggttctatct ttgttaagat   18960
aactgaacat tcattctcac ccgaactcta ctcacttgcg ggttggttcg atgattatca   19020
actattttgc acagcagtca atgcctcgtc ttcagaagca tttttatgct gttttaatta   19080
tttggggctt gctaaggaaa acattaatgg ttttaactta catgcttcct atattcaatg   19140
gcgcaatgaa atagcgttga caccaaccta ttctccttta gcggacaacc cggctacggc   19200
ctgtaagcta aaagcaacgc ctattatctc ggctcgtgag ttagagaaga agccattct   19260 tcgctatctc gttgcatcag ggcgccttct tgtgaggcca ccagaatgca gagagctcta   19320
ttgattatga ccttactttg tctcgttcga gcaaagtttg ctgatgatct actcgatttg   19380
ctcaccttcc cgggtgcaca tcgcttctta cataaaccca cgaggaattc cagcagtctc   19440
tactcgcggg ctaataataa ttttgatgtt ggcgttcttc ctggctaccc cactaagaac   19500
gttaacctct tctcaccact tactaactcc actttgccca ttaatggcct tcatcggagt   19560
taccaaccac tcatgctgaa ttgtcttact aaaataacta accacactct cagcatgtat   19620
ctcctaccta gtgagataca aacttatagc tgcggcggtg ccatggttaa ataccagaca   19680
catgatgcag ttcgtatcat tttagaccte actgccactg accacatctc tgttgaagtc   19740
gttggccaac atggtgaaaa ttatgtgttt gtttgcagtg agcagtttaa ctacaccact   19800
gcattacaca aatctacctt cttctcactt aattctgagc tttattgctt tactaataac   19860
aactacttag gtattcttcc acctgattta actgactttα cggtctaccg tactggtcag   19920
ttctatgcta atggttacct tttaggtact ttacctatta cggttaacta tgttaggttg   19980
tatcggggtc atttgtctgc caatagtgcc cactttgccc ttgcaaacct aaccgataca   20040
ctcataacac ttaccaatac tactatatcg caaatcactt attgtgataa gtcagtagtt   20100
gattcaatag catgccagcg ctcttctcac gaagtggagg atgggtttta ctccgaccct   20160
aaatctgccg ttagagctag gcaacgtact attgttacac tacctaagct ccctgagctt   20220
gaagtagtgc agttaaatat ttctgcacac atggattttg gcgaagccag acttgacagc   20280
gttaccatca atggtaacac atcctattgt gtcaccaagc cttactttag gcttgaaact   20340
aactttatgt gtacaggttg cactatgaat ctgcgcactg atacctgtag ttttgacctg   20400
tcagcagtaa acaatggcat gtcattctct caattctgtc taagcactga atctggtgct   20460
tgtgagatga aaattattgt tacctacgta tggaattact tgctaaggca gcgtttgtat   20520
gttactgctg tagagggcca gactcacact ggaaccactt cagtacatgc aacagacact   20580
tctagtgtaa tcactgatgt ctgcactgac tacactatct atggagtctc tggtactggc   20640
attattaagc catcagatct cttattgcac aatggcatag cattcaccte tccaacaggt   20700 gagctttatg catttaaaaa tataaccact ggcaaaaccc ttcaggtctt accgtgtgaa   20760
accccttctc aactgattgt gataaacaac accgttgtcg gtgctatcac atccagtaat   20820
tcaactgaaa ataataggtt tactactact attgtcacac ctactttctt ttattccaca   20880
aatgccacca ctttcaactg cactaagcct gttttgtcct atggacctat cagcgtgtgt   20940
agtgatggtg caattgtggg aacatccaca ttacagaata ctcgaccatc catagtttca   21000
```

```
ctatacgatg gcgaagttga ataccatct gcattttctc tttccgttca gacggagtac   21060
ttgcaagttc aagcagagca agttatagtt gattgtcctc agtatgtatg caatggcaac   21120
agccgttgtc tacaattact ggcacaatac acctcagctt gctctaacat tgaagcagct   21180
ctgcattcct ctgcacagtt ggatagcaga gagattataa atatgtttca acatcaaca    21240
cagtccttgc agttagctaa tattaccaac ttcaagggtg actacaattt tagcagcata   21300
ctaaccacca gaattggtgg cagatctgct attgaagacc ttcttttaa taaagttgtt    21360
actagtggcc ttggcactgt tgatcaggac tacaaatcct gctctagaga catggccatc   21420
gctgacttag tttgttccca gtattacaat ggcatcatgg ttctacctgg tgttgttgat   21480
gctgagaaaa tggcaatgta tactggctct cttactggag ctatggtatt tggaggactg   21540
actgccgcag cggcaatacc atttgccacg gcagtacaag ctcgcctcaa ttatgtcgca   21600
ctgcaaacaa atgtactaca agaaaaccag aaaattcttg cagaatcatt taaccaagca   21660
gttggcaata tatcacttgc actatcttct gttaatgatg ccatccagca aacttctgag   21720
gctcttaaca ccgtagctat tgctattaaa aagattcaaa cagttgttaa ccagcagggc   21780
gaggcattat cacacctgac tgcacagctg tcaaacaatt ttcaagcaat ttcgacttct   21840
attcaagaca tttacatccg tcttgaggaa gtagaggcta accagcaagt tgaccgtctc   21900
atcacaggac ggttggctgc acttaatgca tatgttactc agttactcaa tcagatgtct   21960
cagattagac aatctcgatt gttagctcag caaaagatta tgagtgtgt caaatcacag   22020
tcgtccagat acggtttctg tggaaatggc acacacatct tctcacttac acagactgca   22080
ccaaatggca tatttttcat gcatgcagtg ctagtaccca acaaattcac acgtgtcaac   22140
gcttctgccg gcatttgtgt ggataatacg agaggctact cattgcagcc tcaacttata   22200
ctctaccagt ttaataactc ctggagagtt acacctagaa atatgtatga cccagactg    22260
ccccggcagg ctgatttcat acaattaact gattgcagcg ttactttta caacaccacc   22320
gctgctaatc ttcccaatat tatccctgac attatagatg tcaatcaaac agtcagtgat   22380
attattgaca atttacctac agcaacacct cctcagtggg atgttggtat ctataacaac   22440
actattctca acctcaccgt tgagattaat gatctacaag agcggtctaa aaacctctca   22500
cagattgcag atcgtttaca aaattatatt gacaatctta acaatactct agttgacctt   22560
gaatggctca acagagtgga aacttacctt aaatggccgt ggtatatatg gcttgccatt   22620
gccctggctc ttattgcatt tgtgacaatc ctcataacaa tctttctttg tactggttgt   22680
tgtggtggtt gctttggttg ttgtggcggt tgttttggcc ttttctctaa gaagaaaagg   22740
tataccgacg accaaccaac accgtccttt aagtttaagg aatggtagtc gacgactggg   22800
ccgttaccat ccctggacaa tatattattg ctatactagt tgtcatctgc attggtgtgg   22860
cactactttt tattaatact tgcttagctt gtgttaaatt atttacaag tgctacctag    22920
gggcagcata tcttgttagg cctattatag tgtactactc caagccgaac cccgtacctg   22980
aggatgagtt tgtaaaagta caccaatttc ctagaaacac tcactatgtc tgacgcagaa   23040
gagtggcaaa ttattgtttt cattgcgatc atatgggcgc ttgcgtcat cctccaggga    23100
ggctatgcca cgcgtaatcg tgtgatctat gttattaaac ttattctgct ttggctgctc   23160
caacccttca ccctagtggt gaccatttgg accgcagtcg acagatcatc taagaaggac   23220
gcagttttca ttgtgtccat aatttttgcc gtactgacct tcatatcctg gccaagtac    23280
tggtatgact caattcgttt attaatgaaa accagatctg catgggcact ctcacctgag   23340
agtagactcc ttgcagggat tatggatcca atgggttcat ggaggtgcat tcccatcgac   23400
```

```
cacatggctc caattctcac accagtcgtt aagcatggca agctcaagct acacgggcaa    23460
gagctggcca atggcatatc agtcagaaat ccgccacagg atatggtgat agtgtcacca    23520
agtgacacct ttcactacac ttttaagaaa cctgtggaat caaacaacga tccagaattt    23580
gctgttctga taccagggt gaccgcgct tcaaacgctg acttcacac cataaccact       23640 tcaaaggccg gtgacgctcg cctgtataag tatatgtaat gtgcaactgc catctgcagc    23700
tgcgagattt atatagattg tgcaataagc ggcacatcag aagagaggat gttcctgagc    23760
ttattgaccc tctcgttaaa actcgctgtt ttgcttacag tctcgtggtt cttgctaatg    23820
ctaatccaat tgcatttagc atactacctc ggaaaattct tatcaatggt gagcctttac    23880
tgcttgaata tggtagcata tatggtaaag actttatcat tcgaccatcg ctccaagtca    23940
ttcttgaaga tgaattaaat taagttttg acaccaatct atcatggctg caccagtagt     24000
ccctactact gacgcgtctt ggtttcaggt gctcaaagct caaacaaaa aggctactca     24060 tcctcagttt cgtggcaatg gagttccgct taactccgcc atcaaacccg ttgaaaacca    24120
tggctactgg ctgcgttaca ccagacaaaa gccaggtggt actcccattc ctccatccta    24180 tgcctttttat tatactggca caggtcccag aggaaatctt aagtatggtg aactccctcc    24240
taatgatacc ccagcaacca ctcgtgttac ttgggttaag ggttcgggag ctgacacttc    24300
tattaaacct catgttgcca aacgcaaccc caacaatcct aaacatcagc tgttacctct    24360
ccgattccca accggagatg gcccagctca aggtttcaga gttgaccct tcaacgctag     24420 aggaagacct caggagcgtg gaagtggccc aagatctcaa tctgttaact ccagaggcac    24480
aggcaatcag cccaggaaac gcgaccaatc tgcaccagct gcggtacgtc gtaagaccca    24540
gcatcaagct cccaagcgga ctttacccaa gggtaaaacc atttctcagg tattggcaa    24600 ccggtctcgt actggtgcca atgtcggctc tgcagacact gagaagacgg gtatggctga    24660
tcctcgcatc atggctctag ccagacatgt gcctggtgtt caggaaatgc ttttcgctgg   24720
ccaccttgag agcaactttc aggcggggc aattacccctt accttctcct actcaatcac    24780
agtcaaggag ggttctcctg actatgagag acttaaggat gcgctcaata cggtcgttaa    24840
ccagacctat gagccaccta ccaaaccaac taaggacaag aagcctgaca aacaagacca    24900
gtctgctaaa cccaaacagc agaagaaacc taaaaaggta actctgccag cagacaaaca    24960
ggattgggag tgggatgatg cttttgagat aaagcaggaa tcagcagcgt agacatcaat    25020
ctatgtctgt taaacccacc caactccact caaatatctc tttggttcca gagagtcgta    25080
gtgtatagcc agagagccag tcagagggcg ctatcatgca aactagggct ggctactcta    25140
gcacagaatc acatcccgat aatcaacagt gctagaaggt tgattatacc atttaatatg    25200
ccgaggccac gcggagtacg atcgagggta cagcataatc tcaacttttg ttgagccaca    25260 atttttaatcc taattggaga aagccaaagg actgtactac ttttgtgggt gtagcagtcg    25320
cccagtggga aagcgccaac taggttacaa ttgtggtggg acaaattag gggaaattaa     25380 attggcttat agggggatg gagcgg                                          25406
```

<210> SEQ ID NO 12
<211> LENGTH: 25402
<212> TYPE: DNA
<213> ORGANISM: Artificial Sequence
<220> FEATURE:
<223> OTHER INFORMATION: full length encoding DNA for PDCoV virus NVSL
      USA/Michigan/8977/2014

<400> SEQUENCE: 12

```
ttatagcatt agtctataat tttatctccc tagcttcgct agttctctac cgacaccaat    60
ccaggtgcgt ctgccaccaa gttggctacc cttcctaggg gcgctttcgc gcttgctcac   120
cattagatta cctggaaacc agccattcag gttggagttt ccccaggctc ttttgtgtgg   180
gcattagcgg cttgtggttt ttgcacaaaa tctaagctac ttaccgttcc tctgaccatc   240
caccacttct atagacagca ctgattaccg tagggtttaa gtcacaccgg tctgcaccgc   300
ccgtcagcgg acacattacc cagcatagca ctccttgcac cgagcctagg taggataaaa   360
ccccctaccg ggtgactctt aaggcgtttc ctccacggga tagccactag tcactaggtg   420
taagtgatct gatctgggcg tattgtgttg cgcaagtgtg atacccatag gagcgtggaa   480
tcctattctg cggctcagtg cctgatatag ctgtgaaatg ccaagaaca agtccaagcg   540 cgacgctatt gcgttgcctg aaaatgtacc accctctg caacttttca ttcatgttgc   600
agctgctgaa gagggtcacc ctaaggttac tacttacctt ggcaactata acctctatgc   660
caccaaggct ccgcctggcg tgcaggttct tagtgctaaa acctctctta ctgactttga   720
gaatgtcttt ggagctcaac ccaccttgcg atcaattcgt aatctggttt gtgaggctcg   780
ctcggctgaa tggacaactt ccaagaatgc ttttgcactc aaagccactc aacttgacta   840
ctctgatgcc gttttgaggg caatgattcg tttctgccct ccaaaggtgt ccacactcgt   900
tgcctttgct ctttttggcc gattggttaa aattgaggac aaggaacttg ctgagttagc   960
tcgtgatact gcccttgagt tggcgtacac ggctaaaatt ggtacatctc ttgctgacac  1020
gagatctgtc tcacttattc ataaggacgc ttatctaact ctcagtaatg aggttgttgg  1080
cgtaactttt actgccgcac ttatggcaaa ggctaccact gttaatggag caatgcaata  1140
ctcaaacttt tacctctacc ctcgtgccac tattaaggta accgatggta aggctgaagc  1200
aattgcaact aagcctctgt ctgctgccac taaaggcaag caaatcacag aggatgtcaa  1260
ccttctccct gactatcagc agctgcttgt tgatcaagtg actggcactg aggttaaggt  1320
tggagctcta acctatgtta agaccactga ttcgccaccc ctttactttc ccaaagtcaa  1380
gggtggtgtt attggtattg cacttaagca gcagggcact gcggctaaga agctcaatgt  1440
agtcttccat gctcaacctg atgatgttct gctagccttc atacaacttc agcaattctt  1500
gaaccgtact tcggattcaa gtgttgaaat tactgattgc cagagttatg aagtatctcc  1560
aactgtgacg gtcaaaattg gcccgtctaa acctggggat gtcatcgtgg ctactgatga  1620
ggaatacctt aaatgctttg aaacccctga ggtaggtagg ctctataagg ttttccaaac  1680
tcaatcttgg gctatcattg agcgtgcctt ctccagtttg aagatccgcg tgtccaaagc  1740
tttatcagca tttataagtt ttctgcaaaa ccttgcagat aactttactg caataagtgg  1800
tgttgtcact gcactcattc gtgaactcca ggatcttacc ctggatgtgg cgacacgtat  1860
cactaacata caatttgttt accgtgccgg taagcttatt gtcgacacga caagtgtcat  1920
agctaaactt ttccagccat tttgtgattt tatatcacct ttccttcgga agttgctgg  1980 ttttgcaatt tacactgttg gtaatcgcat gcttatgttt accagcactg gcacctttct  2040
tctcacaaag gcaactacta agatactcaa taaggcaaag tacatctttg atgtggagcc  2100
tgagtaccca gtagatgtaa caacatccaa agttgtagta catgaagcac tccagcaaac  2160
cgacactaag cctactagag ctctggaggc tgttgatgtc gttgttggta atactgtact  2220
gcaaatggct actgatggca ctgcgttcta cccatcggat ggtacgcacg cctctcttcc  2280
aggattcaaa gcaggttcgg atgagctttt cataagcttc aactgcgacc tctttgatga  2340
```

```
tgagactaat gctcaaatca acgaaatact cgctgcatat gagcttaacc aactagtggc    2400
tccaggtgat tctacaccgc gtcaaattgc gacgttggtt gtcgatacac ttgcagatgc    2460
tataacagac cactttccgg agaaaaccat tgatctacct gaagactatc aagtcttttc    2520
tgaccatgat gacctcccac tcgcacaata ccacatccct gatcacctga gcctgtatat    2580
tcaggctatg gaaggtgaag atgatagtgg tgatgaaata tgtattgagg acgatgatta    2640
cgactgtcct caagccgacg aagacacaga aggagtaatt ccccaacagt gggaacttcc    2700
tgatgttgat aaattttac tcaagatcca ggaacggaag accagcagcg acgaagtact    2760
tagcgtcgac gtctatccta aaccagagcc ggtcggcaat gttgggattg acgacagcgc    2820
gtcggaaaag aagccaaatg ggactcagt accggatcct gaggtccatc caacactaga    2880
gagtgtggat gttgaacgac caaccgaaac agcaaaccag gctgttgaag acaaaccttc    2940
tgataccacc tttgtggttg atgaggaaca attacaagaa tcaacaccag aacatgaact    3000
ccgctcctat gaaggggagt ttgattctga tgatgaaatt attattccta tagtaccagt    3060
aacacctgcg gatttaaaac cacagactat tactataaag gagtactta agtctgaaaa    3120 acttgagact attaacgaag gatccacaga gtcagttaca caatctgacg attcgtttga    3180
cgagtcattt gttgatgctg agtctgatga tccacaagat cctgctgtat atgatgatac    3240
aacaattata acggacagca ctgatgtagg cgatgagcct gagacaactc tagctaccat    3300
cgttaacaca cctctgacac tcgataataa cttgccacct gaagccatta acaacccag    3360 cccaactaag gttgagttag ttgttggtga attggcgagt attaaatttg acaattctgt    3420
tctagtcaac cctgctaatg cgcaattaac aaatggcggt ggagctgctc gtgcaattgc    3480
aaaattagct ggtccaaaat atcaagagta ctgtaatagt gtggctccta tctcaggacc    3540
gcttaccacg gactcttttg atgccaagaa atttggtgta gcctgcatct tgcatgtagt    3600
gccacccaaa ggttctgacc ctaatgtaca agaactcctg tatcaagctt acaagagtat    3660
ccttactgaa ccagcacact atgttatacc tatactaggt gctggtatct ttggatgcaa    3720
cccagtccac tctctggatg cgttcaggaa agcatgtcca agtgacatag gtcgtgtcac    3780
ccttgtcact atgaacaaaa accatttgca ggtgtgggat gctctcaata ggaccattgt    3840
acgcaccact actgactatg atcaagttac caccaaggcc cttacacccc agggagtgtt    3900
agaagccaat ctcttttgatg gtgaggactt tgttcaagaa ccaaaacccg gtcaaatcta    3960
ccttgaggtt actgaagaag ttcagaacca agccaaggaa cttgacctta accttcagca    4020
atactgcgtc tacctgaaga cttgccacca taaatgggtt gtgagtcgta cgaacgggtt    4080
gatgcatcta aaacaaaaag ataacaattg ttttgttagt gcaggtgtaa acctgtttca    4140
aaacactgct tatcaactta gacctgctat tgatgctctc tatagggagt atcttaatgg    4200
taatccaaat agatttgttg cttggatcta cgcatccact aaccgtcgtg ttggtgagat    4260
gggttgtcca cagcaagtta tttctttgct cgttagtaac tctgacgcag catttttcagc    4320 aactacagcc tgttgtaaca cctactttaa ccacacaggt gttatttcag tagctcgtga    4380
atatgaccca atacaaccaa aggtctactg catgaagtgt gatgtgtgga ctcccttttac    4440 accccagagt ggaaaggtg cagttgcaat tggtatttct gcagatgaac ctaccggtcc    4500
tgccattaaa tttgccgcag ctcactgctg gtacactaat ggcaagaaaa cagttaatgg    4560
ctatgacact aaagctaatg ttgtagctac ctatcatagg tttgacgtgc ctaagcctca    4620
acttgtcgag gacgtggttg cgctgccta taaaaatgac tttgaagttc tcaatgttga    4680
agaactgccg caggatagtg tgctccattt ggacccacct cctgtacagg ccttacaacc    4740
```

```
taaggctaac caacacattg agattctaga aaacccagat tatctggaca ttttggatct    4800
ttggattcgt aaacccaaat tcatcctcgt aaagtcgtgg agtgttttgg gtagagcact    4860
atgtaaggca ggtaaagttg tctttgtcaa tgcttcgctt ttgacccgtt tctacaatta    4920
ccttgtagag attggtgctc ttgactcaac aataaggttg tcagtcgatc ttacctgtaa    4980
atttgttaga acggttctcc catcgtctaa cactgtacac aaaacttgtc ttggtctgta    5040
ttattcagcc cagacacttt ttgtttcttt agcaccattc cttatgttac cagctgtagt    5100
tagtctgctt aattcaggct atacaattgg cacatatttg tatgcaaaaa ctggctggcc    5160
ttgtaattac aatgccacgc aacactttga ttataattct tactgtgcag gtgacttggt    5220
ttgtcaagcc tgttttgacg gtcaagactc cctacatttg tatccgcatt tacgtgttaa    5280
tcagcagccc cttcagacca ctgactacac tgtttatgcg ctttcactaa tactactatt    5340
agctaacatg actcttgtca tgggcacgct aatagttact ttctttgtga acttctatgg    5400
tgtgcaaata ccatttttatg gtacactttt gatagattat caatccgcac tggtgattac    5460
tttctcagtg tactactttt ataaggtaat gaagtttttc cgccatctca cacatggatg    5520
taaaattcca acgtgtgtgg tatgtgccaa acttcgtacc ccacctacta aacagttga    5580
gactgtcgtt cagggcagga aatacccatc tgttattgaa acaaatggcg ggtttacaat    5640
ttgtaaagaa cacaacttct attgcaagga ctgctcttta caaacacccg gcactttcat    5700
cccgacagaa gctattgagt cgctctcacg agctaccagg cttagtgtca aaccaacagc    5760
accagcattc ttacttgcta gagatgttga gtgccaaact gatgttgtcg ttgctcgcgc    5820
aatgcataac caaaatgcgc atgtgtgcat ttcaaaatac tctgatatcc gtaccgttga    5880
ccaactactt aagcctactc cactgttttc atacactccc gatgttatca tcgcggcaga    5940
cttttgacaac agaggtagtc ttaagacagc taaagaatta gctgtggttt tgtcaatgga    6000
ccttaaacgt actataatta tcattgatca ggcctattct agacctattg ataattatca    6060
ggaagttgct tctcgtattg agaagtatta cccagttgca aagatcacac ccacaggtga    6120
catctttaca gacattaagc aagcgaccaa tggccaagct agtgactctg ctattaatgc    6180
agctgttctg gctgtccagc gcggtcttga ttttacaatt gacaaccta acaacatatt    6240
accacattac gcctttgact tttcaacccct caatgcagaa gaccagtcta ccattttgga    6300
gagtggttgt gctaaaggca atctcaaggg cactaatgtt ggtgttgttc tttcagctag    6360
ccttgttaca cgtcttagtc agcaggctat acgtgtgatt gctaatgctg cttcacgtaa    6420
tggtgttaca tgcgctgtta ctcccttctac acttgttatg cgtgggaata ttgcaacaca    6480
gcccttgact cgcatcaaag ctggtgcacc tcccatgcgt caaaaatttt tatgtgttat    6540
cctggcactt gctattgtgt actttgctgc tatggctttt ggcttttttgg caagtcaact    6600
tacgcttaat acagtgccta cgattaaatc tgatatccgc gcctctacct tctacgttgt    6660
tagagatgga gtcttggata ctgttcgttc aaatgacaag tgctttgcaa ataagttttt    6720
ggcatttgat agcttcattc aagcaccctta cactaattca cctgactgtc cagttgttgt    6780
gggagttgtt gatgtaacga cgcactctat tcctggaatt ccagcaggtg tcattcatag    6840
agacggtctc atacttaaca tttatgaaca gtctctttat gaaactcatc agcgtcagtc    6900
tatggttagg gatgcgttgt cactcaagac agcaaatctc tttaacctag caagcgtgt    6960
tgtagtagga tacactcaac atgaagttgt tgtgggtacc tcctattta attctcctgc    7020
acttttttaat gcaaagtgca ccttcttaca gtatcaggac actagacaac tctattgcta    7080
```

-continued

```
tgatactgtt cctactgaac ataagctcta ctctgatgtg cttccgcacg tcgagtataa    7140
ggctattgac attaatggtg atcttgttcc tttcaagata ccagagcaga taatgttcta    7200
tccacatatt gtgcgctata ctagcaattc ctattgccgt atggggcatt gttttaatac    7260
taaccctggt atttgcattt catttacgga cgaatttccg tatagtgaaa atgtcaaacc    7320
tggtgtgtac tgtgctgata cctctttgca gttgttttca aacctcgttt tgggcactgt    7380
atctggtatt cacatcttta catcaacagc tgcattgctt ggatctacta ttgtgatcat    7440
actatgcgtt gttgctgttc ttgcagttca gcgattcttc aaggagtaca caacttttgt    7500
tatgtacact tgtggtcttg ctcttgtcaa cattgtaggc attgcactta tgtacaagtg    7560
ccttgtcttc gcgattttct attatgcaat ctacctttac tttgtcctta ctttcccctc    7620
ctttaagagg aatgtggcat tgttttactt cgctgtagtg atcgtgccgc acgtgagtaa    7680
catgcaattg cttgcgctca ttgtgtgtag cattatctac tttctctaca cctatgttca    7740
tactgtagct aagacagctg ggaaattttc ttccttctta gacgcagcta aagctacttt    7800
tgtcattgac aatgaaaagt acgtgttgct aaagacctc gctggtgctg aatttgacca    7860
gtatctggcc tcttacaaca agtacaaata ttttctggt actgcttctg ataaggatta    7920
tgataaggtc tgtatggcat tcttgccaa ggctttgtca tcttttcgtg aaggaggcgg    7980
ttcacagttg tacacaccac ctaaatttgc agttgttcag agtcttaaga ccaagctgca    8040
agcaggtatc aaaatcctcc tgcacccttc aggtgtagtt gagcgatgta tggtctcagt    8100
tgtctacaat ggatctgcat tgaatggcat ctggcttaag aatgttgtct actgcccacg    8160
ccatgtaatt ggaaaattcc gtggtgacca gtggactcac atggtctcaa ttgctgattg    8220
ccgcgacttt atagtcaagt gtccaataca gggtattcag ctaaatgtcc aatcagttaa    8280
gatggtagga gctctcctcc agttaactgt tcataccaac aacacagcca ctccagacta    8340
taagtttgaa aggctacaac aggatcatc gatgacaatt gcttgtgctt atgatggcat    8400
tgtacggcat gtctatcacg tggtcctcca acttaataat cttatttatg caagcttcct    8460
taacggagct tgtggtagtg tgggttacac tcttaagggt aaaacactct acttacatta    8520
catgcaccac attgagtttta acaacaaaac tcatagtggt acagatcttg aaggtaactt    8580
ctatggcccc tatgtggatg aggaagttat tcagcaacaa acagcattcc agtattacac    8640
tgataatgtt gttgctcaat tatatgcaca cttactgact gttgatgcta gaccaaaatg    8700
gctggcacaa tctcagataa gtatcgagga tttcaactca tgggctgcta acaattcctt    8760
tgctaacttc ccatgtgaac aaactaatat gtcctacatt atgggactct cgcaaacagc    8820
tcgagtccct gtagaacgta tcctcaatac cattatacag ctaaccacca atagagatgg    8880
tgcttgtatt atgggatctt atgatttcga gtgcgattgg acgccagaga tggtatacaa    8940
tcaggctcca atttcattgc agtcaggagt agttaagaaa acttgtacgt ggttcttcca    9000
cttcttgttt atggctatta ccatgctact cgctgccatg catgtttttcc ctgtacactt    9060
gtatccaata gtactgccat gcttcactgt cgtggcattc ctgttgactt aaccattaa    9120
acacactgtt gtgtttacca ctacatactt gcttccgtca cttttgatga tggttgtaaa    9180
tgctaacact ttttggatac cgaacacatt tctgcgcacc tgctacgaaa ctatattcgg    9240
ttccccaatt gctcagcgac tgtatggtta cactgttgct ctttatatgc tgatctatgc    9300
tggacttgca atcaactata cgttgaaaac actccggtat agagcaactt cattcttatc    9360
tttttgcatg cagtggttc aatatggtta tgttgcacac attgcgtaca aactgcttaa    9420
taaaccctgg acagaatcac tactcttcac agccttcaca atgctaacca gtcatcccttt    9480
```

```
gttggctgct cttagctggt ggctagctgg tcgcgtaact ctgcccatta tcatgcctga    9540
cttagctatt cgtgttttgg cgtataacgt cattggctat gtcatatgtg ttcgatttgg    9600
ccttatgtgg cttgcaaatc ggttcacaac tgtacctatg ggcacatacc agtatatggt    9660
gtctgtagag caacttaagt acatgatggc agttaagatg tccccaccgc gtaatgcgtt    9720
tgaggtgctt atagccaaca ttagacttct tggtttgggt ggaaaccgta acattgctgt    9780
ttctactgtc caaaacaaaa ttcttgatgc aaaagctact gctgttgttg ttgctaacct    9840
tcttgaaaag gctggcgtca caaacaagca cgctatttgc aaaaagattg tgaaactcca    9900
caatgatacc cttaaagcca ccacttatga ggaggttgag gtagcacttg tgaaacttct    9960
ttctcacata attgagttct tgccaactga tcaggtagat gcttatctag ctgatgcggc   10020
caatgctcaa catgttaata cctatttaga caacttgctt gagaacaaag ctgttgttca   10080
ggctgttgcc gatatcaaca ttaatctgga ttcttataga atttataagg aggcagatgc   10140
tatttataaa cgatctgttg agatgaacga atctccgcag gagcaaaaga aaaagcttaa   10200
agctgttaac attgcaaagg cggaatggga gcgtgaggct gcttctcagc gtaagcttga   10260
aaagcttgct gatgctgcta tgaagtctat gtatcttgca gaacgtgctg aggatcgtcg   10320
cattaagcta acctctggac ttactgcaat gctttaccat atgcttagac gtcttgactc   10380
agatagggta aaagctctgt tgagtgcgc taaggcacaa atcttgccaa tacatgctgt   10440
agtcggaatt tctaatgaca accttaaagt tattttaac gataaggaca gctactctca   10500
ttatgtagag ggcaacacac ttatacataa gggagttcgc tacactattg tgaagaaact   10560
ctccttagat aatgcaccta ttgaaggcgt accagaagaa ttccctgtgg tcgttgagac   10620
tgttagggaa ggtgtgcccc agttgcaaaa taatgagcta tgtttgcgca atgttttcac   10680
tgctcagaac acagctcagg acttcaatgg caatgaatcc actgtaaaat cttttatgt    10740 tactagaacc ggtaagaaga ttttggttgc cattacatca actaaagaca atcttaagac   10800
tgtgacctgc cttactgaga ccggtaagac agtccttaac ttggacccc ctatgcgctt    10860 cacacatacc gtaggtggaa aacagtctgt tgtctatctc tattttattc agaatattag   10920
ttcactcaac agaggtatgg ttattggcca catctctgaa actactatcc ttcaggcaag   10980
tggcactcaa attgagtacc agcaaaatgc ctctcttttg acctatttgg ctttcgctgt   11040
agaccctaag acagcctacc ttaagcatct tgctgatggt gggtctccta tacagggttg   11100
tattcagatg attgctacta tgggtcctgg atttgcagtt actactaaac cacaacctaa   11160
tgagcatcag tattcttatg gtggtgcttc aatttgtctt tattgccgtg ctcatatacc   11220
acatcctggt gttgatggac ggtgccccta caaaggccgc tttgttcaca tcgacaaaga   11280
taaggaacct gtttccttcg ctttgactca tgagccatgc agttcttgtc aacggtgggt   11340
taattatgac tgcacctgcg gatctagtct gcagaattcg gcttatttaa acgcgtaacg   11400
ggttctagtg acgcccggct agaaccctg cagcctggaa ctcaaccaga tgctgtaaaa   11460
agggccttcc atgtgcataa tgataccacc tctggtatat tcttaagcac aaaatctaac   11520
tgcgctcggt ttaaaccac acgcagtgcc ctgcctttac ctaataaggg agaggttgaa   11580
ttgtactttg ttactaagca gtgtgcagct aaagtcttcg aaatcgagga ggaatgctac   11640
aacgctctta gtacagagct ttatactact gatgatacat ttggtgtcct tgccaaaact   11700 gagttctttta agtttgacaa gatacctaat gtcaatcgcc agtatctgac taaatataca   11760
ctcctggact tggcttatgc tctacgtcat ttgtcaacat ctaaggatgt tattcaagaa   11820
```

```
atcttgatca ccatgtgcgg aacccctgaa gattggtttg gggaaaattg gtttgatcca   11880
attgagaacc catccttta caaggagttc cataaacttg gggatattct taaccgttgt    11940
gttcttaatg ccaataagtt tgctagtgcc tgtatagacg ctggtcttgt tggcatatta   12000
acacccgaca accaagacct cctgggtcag atctatgact ttggagattt tattattaca   12060
caaccaggta atggatgtgt ggacttagca tcctattatt cttatttaat gcccattatg   12120
tccatgactc acatgttaaa gtgtgagtgt atggatagtg atggcaaccc acttgagtat   12180
gatggatttc agtatgactt cacggacttc aagcttggct tgttcgagaa gtattttaag   12240
tactgggacc gtccttatca tcctaacact gttgaatgtc cagatgaccg ttgcgtattg   12300
cactgtgcga acttcaatgt gttgtttgct atgtgtatac ctaatacggc atttggcaat   12360
ctttgttcaa gagctactgt tgatggccac cttgtggtcc agacagtggg tgtacacttg   12420
aaagaactcg gtatagtcct taaccaggac gttaccacac acatggcaaa tattaatcta   12480
aacactctat tgcgattggt tggtgatccc accactattg caagtgtctc agacaagtgt   12540
gtagatttaa gaactccttg tcagaccttg gctactatgt ctagcggaat tgctaaacag   12600
tcagtcaagc ccgggcattt taatcaacac ttctacaagc atttgcttga tagtaaccta   12660
ttagaccaac ttgaaataga cattcgccac ttctactata tgcaggatgg tgaagcggct   12720
atcacagact acagctacta caggtataat accccacga tggtagatat caagatgttc   12780
ttattttgcc ttgaggtggc agataagtat cttgagccct acgaaggtgg atgtattaat   12840
gcacagtcag ttgtggtctc taatttggac aagtcagcgg gctaccccctt taacaagcta   12900 ggtaaggctc gtaactatta cgacatgact catgccgagc aaaatcaact gtttgagtat   12960
acaaaacgca atgttttgcc tacactcact cagatgaacc ttaagtatgc aatttcagcc   13020
aaggatcgtc tcgcactgt ggcaggagtg tctataatta gcaccatgac taacaggcag   13080
taccatcaaa agatgctgaa atctatttca cttgcacgca atcagaccat cgtgattgga   13140
acaaccaaat tctatggtgg ttgggacaac atgttacgac gactgatgtg taatatcaac   13200 aatccattt agtgggttg gattaccct aagtgtgatc gttctatgcc aaacatgctg   13260
cgcattgccg cttcgtgctt gctagcacga aaacacactt gctgtaacca aagccagcga   13320
ttctaccgtt tggctaatga atgttgccaa gtactatctg aagtggtagt ctctggtaac   13380
aacctctatg taaaccagg tggcactagc agtggtgatg caaccacagc ttatgccaac   13440
tcggtattta acatcttaca ggtggtttct gctaatgtag ccaccttctt atcaacttcc   13500
accacgacac atcttaataa ggacattgcg gacttgcatc gtagtctta tgaagatatt   13560 tatcgtggtg actctaatga tatcaccgtc atcaatagat tctaccagca tctccaaagt   13620
tactttggac ttatgatatt gtctgatgat ggtgtcgcat gcatagactc agccgttgca   13680
aaggctggag ctgttgctga tcttgatggt tccgagaca ttttgttta ccaaaacaat   13740 gtttacatgg cagactcaaa gtgttggaca gaaactgaca tgaatgttgg ccctcatgaa   13800
ttttgctcac agcatactgt gttagcagag catgatggta acccttacta cttaccttac   13860
ccagatgtct ctcgcattct gggtgcatgc atctttgtgg atgacgttaa caaggctgac   13920
cctgttcaga accttgaacg ttacatctca cttgcaattg atgcatatcc cctcaccaag   13980
gttgacccta ttaagggtaa agtctttat ttgttactag actacatacg tgttcttgct   14040
caggagttac aggacggtat ccttgatgct ttccaatcac tcactgacat gtcgtatgta   14100
aataacttta tgaatgaggc cttttatgct cagatgtatg agcaaagtcc tacactacag   14160
gccagcggtg tttgtgtggt gtgtaattca cccactatac tgcgctgtgg tgattgcatt   14220
```

```
cgtcgaccac tactttgttg cgtctgtgcc taccagcatg ttacgcagac tacacataaa    14280
cgtatcattg ctatcaacaa ctacatctgt agtgttgaga attgcaatga ggacaatgtt    14340
gaaaaacttt tcatttctgg cactgcgatt tattgtgaga atcacaaacc cacgctgtgc    14400
atacccattg tagctaatgg ttctgttttt ggtatctatc gccacactgc ccgtggtagt    14460
gatgacatag acctctttaa cgagcttgct acatctaact atgacactat tgaaccttat    14520
cagaaggcca atcgtgcacc tttatcactt atgctcttcg ctgctgaaac cattaaggca    14580
ctcgaggagt ctatcaagaa gtcatatgct accgcaaccg tcaaggatgt gtatgaccaa    14640
cgcttcatta aacttctatg ggaacagggt aaaaagccgc cacccataac gaagaaccac    14700
attttcactg gctaccattt taacaagaat ggaaaaaccc aagttggtga ttacattctt    14760
gctaaaacag atggcagtga cacttatact tacagaggaa catctaccta caaactccaa    14820
acaggtgatg ttctagtctt aatggcacat gttgttacac cgctctcagc accccctgtg    14880
ttaacgcaga caacatatgt cagaaaatca cttttacccg actctgttgg tgcgtcttat    14940
tatgtgcaac attttaagtc atataatgag atagctatgc agagggttac aacagtatta    15000
ggtccaccag gcacaggtaa gtcaacctt gctattggtt tggctaagta ctttcccagt    15060
gcacgtattt gctacactgc gtcttcgcat gcagcaatcg atgcactctg tgaaaaagct    15120
ttcaagacaa tacctgtagg ccaatgcagt cgtatcgtac ccacacgtac aactgttgag    15180
tgctttcagg agtttgtcgt aaataacaca actgcacagt atatcttctc gactatcaat    15240
gccttacctg acattaagtg tgacattgta gttgtagatg aggtttctat gttgaccaat    15300
tatgagcttt cctctgtgaa tgctcgtttg gtttacaatc acattgtgta tgttggtgat    15360
ccttatcagt taccttcacc tagaactatg cttacgtctg gccagcttc gccagctgac    15420 tataacgtag ttactgatat aatggtacat gcaggagcgg atgttatgct cgacatgtgc    15480
tacagatgcc cacgtgaaat cgttgagaca gtgtctaaac ttgtctacga taacaaacta    15540
aaagcggcga aaccgaactc aagacagtgt acaagacca ttgtgaactt tggtcctgga    15600
gacgttgctc atgagggaca atctgcctac aacgaagcac agttgcgttt cgcactcgca    15660
tttagacaac aaaagcggtg ggataacgtg actttcatat ctccatataa tgctatgaat    15720
gtgaaagcat ccttagcagg tttctctact cagaccgttg actcttctca aggttctgag    15780
tatgattatg ttatcttttg cgtgaccact gattcagcac acgcacttaa catggctcgt    15840
ttgaacgttg cccttacacg cgcaaagata ggtatccttg tggtgtttag gcaggcaaac    15900
gaactttaca atagtttgca gtttgaatct attgattcac agcttcagtc gagtgctgag    15960
aaaaacctca caccactgtt taagcgctgc ggctatgagt ataatggcgt ccatccagct    16020
catgctttga cctggcatga ttgtggtgca gagtaccgct gtgaggagcc acttgctaaa    16080
ttagtaggag ttgccgatgg cactcttata tcatacaaaa ccctagtatc cacacttggg    16140
tttcttccat cacttaaaat tgatgcatat cataatatgt tcctaacacg tgacgcgtgt    16200
cgcacctatg ttcagagttg gatcggcata gatgttgaag cagcacacgc cataaaacct    16260
aacaccggga ctaacctgcc attgcaaata ggttttagta ccggaaagaa ttttcagtc    16320 actccagagg gaatttgggt aaacgagcac ggatcttgca ctgagcccgt ccctgccaaa    16380
atacctcctg gagaacaatt tcgtcacctt aaaaaggaca tgcgccaggc gcgtccttgg    16440
aaggttgttc gacgtgagat tgctactcac attgctgagg tagctcctca cactgattat    16500
atatgctttg tcacttgggc tcaccagctt gagctagcga caatgcgcta ctttgtcaaa    16560
```

-continued

```
ctaggtatgg aagagaaatg cttttgtggc aggcgggctt gtttcactaa tggaactgag    16620
ttcgcttgca aagcacacca ttctctcacc attccacaat gtgattatgt gtacaatcca    16680
ttcctcatcg acgtggctac gtggggattc tcgggacggc tttccaccaa ccatgacgct    16740
gtgtgcacat atcatgctaa tgcccatgtt gcatcagctg atgcaatcat gacggtatgt    16800
ttagctatcc atgaactgtt cagtactgtt gactggaact ttgaatttcc agtaactgct    16860
gagcaatcgc aacttaacaa ggcctgtcgc ttagtacagg cgaattactt aaatatacta    16920
ctcactacaa ccaaagccac ggtggttcac gatattggta acccaaaagg tatccctatc    16980
gtgcgcaaac ctggtgttaa atatcacttc tatgatcaag cacccattgt caaacacgtt    17040
caaaaactaa agtacaagcc agagatggag gcccgtttca ccgatggttt gactatgttt    17100
tggaattgta atgttgacac ataccctgct aacgcccttg tgtgccgcta cgacactcat    17160
cggcagaagc atttaattgg acctaatggt tcagcactat atgttaataa gcatgctttt    17220
ctcaccctg agatgcatac ttatgctaca cataaactca acttggctcc actcatctac    17280
tactccacca cagattgtag tagtgaacag cctattgttg ttacctacag agattgtgtc    17340
acccggtgca atactggaaa aactctctgt ccaaatcatg ctcttgaata ccaagagttt    17400
atcaatgcat acaatctcat ggctcgccat ggatttaatg tttacatacc acgcaatgtc    17460
aacgtttaca actgttggct tactttcact aatctccaaa accttgaaaa cttagcttac    17520
aactgttatt ataagaactg caatgctcac gttgatgggc agcttgatgt agttattaat    17580
aataacgctg tatatgctaa ggtcgacaat aatcttgtca aacttttcga caaccgcact    17640
aacttacctg tctcagtggc ctttgaacat acactaaca ggcatacccg ttcactgcca    17700
actacacagc tgttatctgg tttaggcgta accgccacca gaaatttcac tgtgtggttc    17760
gacaatgata caattttcca atacactatt aatgtatcta cgtatactga catcgaccct    17820
agtacccatg ttgtcctctg tgatgatagg tacggaacag attggagtca gtttaaccaa    17880
cttcctaatg cagtattcct caccaaaact aaggtgaaga aaacagaacc gtttgtttgt    17940
acagcactga ccctaaatgg cgtcgccatt gacggtgaag agctatacat ctatgtacgc    18000
tataacaatc aactgaccac atttgctact acttgtacac agggtagaaa tgttgagcag    18060
tttataccta aaacacctat ggaaagagac ttccttgaga tgtctcaaca gtccttcatc    18120
cagcaacatc aattgcagga actgggtgtt gaacacatta tctatggtga tgattccagt    18180
ccagtcattg gcggaactca cacacttatc tcactagtta aaaacaagtt tgaacatcag    18240
cttgtcaacc atgtttacaa cccagtccag aactgtgttg ttacctcacc taacgcaagc    18300
tccaagaacg tttgcactgt tcttgatgtt cttcttgatg actacattga catcataaga    18360
caagcacatg ccagttacac aagtaaatcc aaagtattca ctgtgtcaat tgacaaccaa    18420
caaattagat tcatgctttg gcatgatgag caagtcaaga cttgctaccc aatcttacag    18480
tcacttacca atggttacca gatgccatct gtgtacaaaa cattggttac tgacttacaa    18540
ccagctgaca tccctaatta tcattcctac accccccggg tgcctggagt agttaagaat    18600
gttatcaagt accgccaact tttcaactac atagttaaaa aggataggtt ggcagtacca    18660
cacaatatga ccgtattaca ccttggagct gcatctgcac taggtacagc accaggttct    18720
tcagtcataa acaaatgtt tcctgaagga actgttctta ttgacctcga tataagagag    18780
ttcacttcag atgctaacca aataatagtt acagactaca gaacttacat accaccacac    18840
cacgtagacg tcatattttc tgacctctac tgttgtgatg acatacactt ctttgacaat    18900
ctaataagga tagttaagga gaggctcgcc ctcggtggtt ctatctttgt taagataact    18960
```

```
gaacattcat tctcacccga actctactca cttgcgggtt ggttcgatga ttatcaacta   19020
ttttgcacag cagtcaatgc ctcgtcttca gaagcatttt tatgctgttt taattatttg   19080
gggcttgcta aggaaaacat taatggtttt aacttacatg cttcctatat tcaatggcgc   19140
aatgaaatag cgttgacacc aacctattct cctttagcgg acaacccggc tacggcctgt   19200
aagctaaaag caacgcctat tatctcggct cgtgagttag agaagaagcc tattcttcgc   19260
tatctcgttg catcagggcg ccttcttgtg aggccaccag aatgcagaga gctctattga   19320
ttatgacctt attttgtctc gttcgagcaa agtttgctga tgatctactc gatttgctca   19380
ccttcccggg tgcacatcgc ttcttacata aacccacgag gaattccagc agtctctact   19440
cgcgggctaa taataatttt gatgttggcg ttcttcctgg ctaccccact aagaacgtta   19500
acctcttctc accacttact aactccactt tgcccattaa tggccttcat cggagttacc   19560
aaccactcat gctgaattgt cttactaaaa taactaacca cactctcagc atgtatctcc   19620
tacctagtga gatacaaact tatagctgcg gcggtgccat ggttaaatac cagacacatg   19680
atgcagttcg tatcatttta gacctcactg ccactgacca catctctgtt gaagtcgttg   19740
gccaacatgg tgaaaattat gtgtttgttt gcagtgagca gtctacctac accactgcat   19800
tacacaaatc taccttcttc tcacttaatt ctgagcttta ttgctttact aataacacct   19860
acttaggtat tcttccacct gatttaactg actttacggt ctaccgtact ggtcagttct   19920
atgctaatgg ttacctttta ggtactttac ctattacggt taactatgtt aggttgtatc   19980
ggggtcattt gtctgccaat agtgcccact ttgcccttgc aaacctaacc gatacactca   20040
taacacttac caatactact atatcgcaaa tcacttattg tgataagtct gtagttgatt   20100
caatagcatg ccagcgctct tctcacgaag tggaggatgg gttttactcc aaccctaaat   20160
ctgccgttag agctaggcaa cgtactattg ttacactacc taagctccct gagcttgaag   20220
tagtgcagtt aaatatttct gcacacatgg atttttggcga agccagactt gacagcgtta   20280
ccatcaatgg taacacatcc tattgtgtca ctaagcctta cttcaggctt gaaactaact   20340
ttatgtgtac aggttgcact atgaatctgc gcactgatac ctgtagtttt gacctgtcag   20400
cagtaaacaa tggcatgtca ttctctcaat tctgtctaag cactgaatct ggtgcttgtg   20460
agatgaaaat tattgttacc tacgtatgga attacttgct aaggcagcgt ttgtatgtta   20520
ctgctgtaga gggccagact cacactggaa ccacttcagt acatgcaaca gacacttcta   20580
gtgtaatcac tgatgtctgc actgactaca ctatctatgg agtctctggt actggcatta   20640
ttaagccatc agatctctta ttgcacaatg gcatagcatt ccctctccca acaggtgagc   20700
tttatgcatt taaaaatata accactggca aaacccttca ggtcttaccg tgtgaaaccc   20760
cttctcaact gattgtgata aacaacaccg ttgtcggtgc tatcacatcc agtaattcaa   20820
ctgaaaataa taggtttact actactattg tcacacctac tttctttttat tccacaaatg   20880 ccaccacttt caactgcact aagcctgttt tgtcctatgg acctatcagc gtgtgtagtg   20940
atggtgcaat tgtgggaaca tccacattac agaatactcg accatccata gtttcactat   21000
acgatggcga agttgaaata ccatctgcat tttctctttc cgttcagacg gagtacttgc   21060
aagttcaagc agagcaagtt atagttgatt gtcctcagta tgtatgcaat ggcaacagcc   21120
gttgtctaca attactggca caatacacct cagcttgctc taagattgaa gcagctctgc   21180
attcctctgc acagttggat agcagagaga ttataaatat gttcaaaaca tcaacacagt   21240
ccttgcagtt agctaatatt accaacttca agggtgacta caatttttagc agcatactaa   21300
```

```
ccaccagaat tggtggcaga tctgctattg aagaccttct ttttaataaa gttgttacta    21360
gtggccttgg cactgttgat caggactaca aatcctgctc tagagacatg gccatcgctg    21420
acttagtttg ttcccagtat tacaatggca tcatggttct acctggtgtt gttgatgctg    21480
agaaaatggc aatgtatact ggctctctta ctggagctat ggtatttgga ggactgactg    21540
ccgcagcggc aataccattt gccacggcag tacaagctcg cctcaattat gtcgcactgc    21600
aaacaaatgt actacaagaa aaccagaaaa ttcttgcaga atcatttaac caagcagttg    21660
gcaatatatc acttgcacta tcttctgtta atgatgccat ccagcaaact tctgaggctc    21720
ttaacaccgt agctattgct attaaaaaga ttcaaacagt tgttaaccag cagggcgagg    21780
cattatcaca cctgactgca cagctgtcaa acaattttca agcaatttcg acttctattc    21840
aagacattta caaccgtctt gaggaagtag aggctaacca gcaagttgac cgtctcatca    21900
caggacggtt ggctgcactt aatgcatatg ttactcagtt actcaatcag atgtctcaga    21960
ttagacaatc tcgattgtta gctcagcaaa agattaatga gtgtgtcaaa tcacagtcgt    22020
ccagatacgg tttctgtgga aatggcacac acatcttctc acttacacag actgcaccaa    22080
atggcatatt tttcatgcat gcagtgctag tacccaacaa attcacacgt gtcaacgctt    22140
ctgccggcat ttgtgtggat aatacgagag ctactcatt gcagcctcaa cttatactct    22200
accagtttaa taactcctgg agagttacac ctagaaatat gtatgaaccc agactgcccc    22260
ggcaggctga tttcatacaa ttaactgatt gcagcgttac ttttttacaac caccgctg    22320 ctaatcttcc caatattatc cctgacatta tagatgtcaa tcaaacagtc agtgatatta    22380
ttgacaattt acctacagca acacctcctc agtgggatgt tggtatctat aacaacacta    22440
ttctcaacct caccgttgag attaatgatc tacaagagcg gtctaaaaac ctctcacaga    22500
ttgcagatcg tttacaaaat tatattgaca atcttaacaa tactctagtt gaccttgaat    22560
ggctcaacag agtggaaact taccttaaat ggccgtggta tatatggctt gccattgccc    22620
tggctcttat tgcatttgtg acaatcctca taacaatctt tctttgtact ggttgttgtg    22680
gtggttgctt tggttgttgt ggcggttgtt ttggcctttt ctctaagaag aaaaggtata    22740
ccgacgacca accaacaccg tcctttaagt ttaaggaatg gtagtcgacg actgggccgt    22800
taccatccct ggacaatata ttattgctat actagttgtc atctgcattg gtgtggcact    22860 acttttatt aatacttgct tagcttgtgt taaattattt tacaagtgct acctaggggc    22920
agcatatctt gttaggccta ttatagtgta ctactccaag ccgaacccg tacctgagga    22980 tgagtttgta aaagtacacc aatttcctag aaacactcac tatgtctgac gcagaagagt    23040
ggcaaattat tgttttcatt gcgatcatat gggcgcttgg cgtcatcctc cagggaggct    23100
atgccacgcg taatcgtgtg atctatgtta ttaaacttat tctgctttgg ctgctccaac    23160 ccttcacct agtggtgacc atttggaccg cagtcgacag atcatctaag aaggacgcag    23220
ttttcattgt gtccataatt tttgccgtac tgaccttcat atcctgggcc aagtactggt    23280
atgactcaat tcgtttatta atgaaaacca gatctgcatg ggcactctca cctgagagta    23340
gactccttgc agggattatg gatccaatgg gtacatggag gtgcattccc attgaccaca    23400
tggctccaat tctcacacca gtcgttaagc atggcaagct caagctacat gggcaagagc    23460
tggccaatgg catatcagtc agaaatccgc cacaggatat ggtgatagtg tcaccaagtg    23520
acacctttca ctacttttt aagaaacctg tggaatcaaa caacgatcca gaatttgctg    23580
ttctgatata ccagggtgac cgcgcttcaa acgctggact tcacaccata accacttcaa    23640
aggccggtga cgctcgcctg tataagtata tgtaatgtgc aactgccatc tgcagctgcg    23700
```

-continued

```
agatttatat agattgtgca ataagcggca catcagaaga gaggatgttc ctgagcttat  23760
tgaccctctc gttaaaactc gctgttttgc ttacagtctc gtggttcttg ctaatgctaa  23820
tccaattgca tttagcatac tacctcggaa aattcttatc aatggtgagc ctttactgct  23880
tgaatatggt agcatatatg gtaaagactt tatcattcga ccatcgctcc aagtcattct  23940
tgaagatgaa ttaaattaaa gttttgacac caatctatca tggctgcacc agtagtccct  24000
actactgacg cgtcttggtt tcaggtgctc aaagctcaaa acaaaaaggc tactcatcct  24060
cagtttcgtg gcaatggagt tccgcttaac tccgccatca aacccgttga aaaccatggc  24120
tactggctgc gttacaccag acaaaagcca ggtggtactc ccattcctcc atcctatgcc  24180
ttttattata ctggcacagg tcccagagga aatcttaagt atggtgaact ccctcctaat  24240
gatacccccag caaccactcg tgttacttgg gttaagggtt cgggagctga cacttctatt  24300
aaacctcatg ttgccaaacg caaccccaac aatcctaaac atcagctgct acctctccga  24360
ttcccaaccg gagatggccc agctcaaggt ttcagagttg acccccttcaa cgctagagga  24420
agacctcagg agcgtggaag tggcccaaga tctcaatctg ttaactccag aggcacaggc  24480
aatcagccca ggaaacgcga ccaatctgca ccagctgcgg tacgtcgtaa gacccagcat  24540
caagctccca agcggacttt acccaagggt aaaaccattt ctcaggtatt tggcaaccgg  24600
tctcgtactg gtgccaatgt cggctctgca gacactgaga agacgggtat ggctgatcct  24660
cgcatcatgg ctctagccag acatgtgcct ggtgttcagg aaatgctttt tgctggccac  24720
cttgagagca actttcaggc gggggcaatt acccttacct tctcctactc aatcacagtc  24780
aaggagggtt ctcctgacta tgagagactt aaggatgcgc tcaatacggt cgttaaccag  24840
acctatgagc cacctaccaa accaactaag gacaagaagc ctgacaaaca agaccagtct  24900
gctaaaccca aacagcagaa gaaacctaaa aaggtaactc tgccagcaga caaacaggat  24960
tgggagtggg atgatgcttt tgagataaag caggaatcag cagcgtagac atcaatctat  25020
gtctgttaaa cccacccaac tccactcaaa tatctctttg gttccagaga gtcgtagtgt  25080
atagccagag agccagtcag agggcgctat catgcaaact agggctggct actctagcac  25140
agaatcacat cccgataatc aacagtgcta gaaggttgat tataccattt aatatgccga  25200
ggccacgcgg agtacgatcg agggtacagc ataatctcaa cttttgttga gccacaattt  25260
taatcctaat tggagaaggc caaaggactg tactacttt gtgggtgtag cagtcgccca  25320
gtgggaaagc gccaactagg ttacaattgt ggtggggaca aattagggga aattaaattg  25380
gcttataggg gggatggagc ag                                           25402
```

VACCINE COMPOSITIONS FOR PORCINE EPIDEMIC DIARRHEA VIRUS AND PORCINE DELTACORONAVIRUS

CROSS-REFERENCE TO RELATED APPLICATIONS

The present application is a continuation of U.S. application Ser. No. 16/282,953 filed on Feb. 22 2019, now allowed, which is a continuation of U.S. application Ser. No. 15/324,908, filed Jan. 9, 2017, now issued as U.S. Pat. No. 10,251,950, which represents the U.S. national stage (37 USC 371) of international application PCT/US2015/039475, filed Jul. 8, 2015, and claims the benefit of U.S. Provisional Applications 62/023,302 filed Jul. 11, 2014; 62/037,403 filed Aug. 14, 2014; 62/046,256 filed Sep. 5, 2014; 62/093,657 filed Dec. 18, 2014; 62/102,712 filed Jan. 13, 2015; 62/115,806 filed Feb. 13, 2015; 62/121,193 filed Feb. 26, 2015; and 62/143,412 filed Apr. 6, 2015.

FIELD OF THE INVENTION

The present invention is directed to novel immunogenic compositions that protect swine from disease caused by porcine epidemic diarrhea virus (PEDV). The present invention is also directed to novel immunogenic compositions that protect swine from disease caused by porcine deltacoronavirus (PDCoV), and combination vaccines providing both PDCoV and PEDV antigens.

BACKGROUND OF THE INVENTION

Porcine epidemic diarrhea (PED) is highly contagious and is characterized by dehydration, diarrhea, and high mortality in swine, particularly young piglets. The causative agent, porcine epidemic diarrhea virus (PEDV), is a single stranded, positive sense RNA virus identified to the Alphacoronavirus genus of the family Coronaviridae. PEDV has a total genome size of approximately 28kb and contains 7 open reading frames. Symptoms of PEDV infection are often similar to those caused by transmlssible gastroenteritis virus (TGEV), also a member of the Coronaviridae. It should be noted that cross protection between PEDV and TGEV is not generally observed, the overall viral nucleotide sequences being at most about 60% similar.

PED was likely first observed in Europe circa 1970, and the causative virus was subsequently characterized (see for example M. Pensaert et al. Arch. Virol, v. 58, pp 243-247, 1978 and D. Chasey et al., Res. Vet Sci, v. 25, pp 255-256, 1978). PED disease was generally considered unknown in North America until 2013, at which point widespread outbreaks commenced, and severe economic losses to the swine industry resulted.

Prototype North American isolates have remained genetically closely related (i.e. with overall nucleotide identity generally over 99%), and are similar to Asian strains characterized there within a few years prior to the North American outbreaks. PEDV generally grows poorly in culture, and there is a need to identify both particular strains and culture conditions that are appropriate for the culturing of sufficient virus for commercial vaccine preparation.

Additionally, there is a need to develop vaccines that provide effective cross protection against known isolates of PEDV, and which are expected to provide effective cross protection against evolving, non-prototype PEDV strains.

Additionally, variant strains of PEDV (for example Calaf14, see SEQ ID NOS 1, 4 for S protein sequence) have been recently identified in Europe, which are recognizably different from known European strains. Such variant strains (similar to Calaf14 based on spike protein sequence) have also appeared in North America, and previously in Asia, and may be more similar to each other than to prototype strains. Accordingly, there is a need to identity both vaccine strains and appropriate vaccine compositions that will be effective against current and emerging worldwide outbreaks of PEDV, thus providing needed cross protection.

Porcine deltacoronavirus (PDCoV) is a member of a novel group of coronaviruses which were initially identified as "Group 3c coronaviruses" by Woo et al. (J Virol., 83(2): 908-917, 2009) in various avian species. Subsequently, these viruses were reclassified as "deltacoronaviruses", and have been identified in other avian species, as well as in pigs (Woo et al., J Virol., 86(7):3995-4007, 2012; Marthaler et al., Genome Announc., 2(2):e00278-14, 2014; Li et al., Genome Announc., 2(2):e00278-14, 2014; Wang et al., Genome Announc., 2(2):e00291-14, 2014; Wang et al., Emerg. Infect. Dis., 20(7):1227-1230, 2014). The genome size of deltacoronaviruses (~25-26 kb) is smaller in size than PEDV and other alphacoronaviruses, which can approach 32 kb.

PDCoV has to date been detected at least in Hong Kong, Canada, China and the US, and while the death rate in piglets reported for PDCoV infections (30-40%) is apparently lower than that typically observed with PEDV infection, interpretation of field data is often difficult since co-infections with PEDV and other intestinal pathogens are common (EFSA Journal, 12(10):3877, 2014). While more knowledge on the pathogenesis and clinical implications of PDCoV is needed, this recently-identified virus appears to be an emerging pathogen in pigs. Thus, efficacious vaccine compositions for treating and preventing disease caused by PDCoV are desired, as are combination vaccines that prevent and/or treat both PEDV and PDCoV diseases.

SUMMARY OF THE INVENTION

The present invention encompasses an immunogenic composition comprising inactivated PEDV, one or more adjuvants, and optionally one or more excipients, in an amount effective to elicit production of neutralizing antibodies in swine. The adjuvant preferably provides an oil-in-water emulsion with additional components. The immunogenic compositions of the invention protect swine from infection by PEDV, and are effective in single doses, in two-dose programs, or in vaccination programs involving multiple doses, which may be spread apart by at least a week, and optionally at greater intervals of time, such as one to several months. It should be noted that depending on the level of epidemic threat in a particular swine population, the vaccine dose program of one, two, or multiple doses may be repeated, from time to time, as a precautionary measure. Additionally, it should be noted that vaccinating a mother sow during pregnancy will provide protection to a young piglet, via maternal transfer of antibodies and T-cells in milk, although such protection may need to be followed up with additional vaccination doses to the piglet. Vaccination of all swine including piglets and adults is contemplated.

It should be noted that although the prototype North American PEDV strains used in the practice of the invention are useful in control of North American disease outbreaks (and indeed USA/Colorado/2013, see below, has now been licensed for this purpose), it has been surprisingly discovered that such prototype North American strain vaccines are also cross protective against European and Asian strains generally, and are also effective against emerging isolates of PEDV disease, such as those that appear similar to Calaf14 (and other emerging European, Asian and North American strains) based on spike sequence. One example of such an emerging North American "Calaf14-like" strain is PEDV-INDEL (OH851) first isolated by the Ohio Department of Agriculture (L. Wang et al., Emerg. Infect. Dis., 2014, v. 20, pp. 917-919). Indeed, it appears that circulating North American strains now cluster into 2 distinct clades, the recently emerging clade having insertions and deletions in spike gene (S-INDELS) which all share 98-100% identity at a nucleotide level (spike gene), but such recent isolates only present about 96-97% identity at the nucleotide level (spike gene) with initial (prototype) North American strains (see also A. Vlasova et al. "Distinct Characteristics and Complex Evolution of PEDV Strains, North America, May 2013-February 2014", Emerging Infectious Disease, Vol 20, No. 10, 2014. Such S-INDELs tend to be less virulent, and more readily attenuated for use in live vaccines. The first public disclosure of North American S-INDELs may be that of the Iowa State University Veterinary Diagnostic Laboratory, on Jan. 30, 2014, defined as having only 93.9-94.6% identity to previously identified USA strains, but being nearly identical (99+%) to each other. Useful insertions and deletions need not be confined to the spike gene. ORF3 modifications (particularly deletions) have been correlated with adaptation to cell culture and reduction of pathogenicity (see S-J. Park etal., Virus Genes, 2008, v 36, pp. 95-104; and others (see J. Zhang et al. Journal of Clinical Microbiology, v. 52(9), pp. 3511-3514, 2014) have commented that classification of PEDVs based on ORF3 may be appropriate. INDEL-type strains have also been previously identified in Asia. see for example, D. S. Song et al., Research in Veterinary Science, v 82, pp. 134-140, 2007; S-J Park et al., Virus Genes, v 35, pp..55-64, 2007; and further discussion thereof by D. Song et al. (Virus Genes (2012) v 44 pp. 167-175) referring to the DR13 strain, passaged to level 100, and previously licensed in Korea (see also KR patent 0502008). Finally T. Oka et al., Veterinary Microbiology, 173, pp 258-269 (2014) disclose additional S-INDEL strains, and a PEDV strain related to prototype virulent strains but bearing a large 197 amino acid deletion from the S protein, possibly resulting from passaging.

Thus, according to the practice of the present invention, there are provided vaccines against PEDV based on inactivated virus, such as inactivated USA/Colorado/2013 strain (SEQ ID NO: 7), which are highly effective, including on a worldwide basis (to include North America, Europe and Asia), including against prototype strains and INDELs. In a further important aspect of the invention, there are also provided vaccines against PEDV based on Calaf14 strain (whether inactivated or live) which are similarly worldwide effective. Thus, the vaccinating compositions of the present invention are useful to protect swine from disease or challenge by PEDV generally, on a worldwide basis, including more recent isolates, such as, but not limited to isolates that show homology with S-INDEL North American variants, such as OH851, or other emerging variants. In this regard, protection is accorded against all of the prototype, INDEL, or other variant strains as mentioned in the immediately preceding paragraph. It should also be understood that by use of preferred "TXO" adjuvant compositions (as further defined below) it is possible to provide inactivated vaccine compositions based on nearly any PEDV or PDCoV strain that are effective and protective for challenge in swine with nearly any other PEDV or PDCoV isolate.

The present invention also encompasses an immunogenic composition comprising inactivated PDCoV, one or more adjuvants, and optionally one or more excipients, in an amount effective to elicit production of neutralizing antibodies in swine. The adjuvant preferably provides an oil-in-water emulsion with additional components. The immunogenic compositions of the invention protect swine from infection by PDCoV, and are effective in single doses, in two-dose programs, or in vaccination programs involving multiple doses, which may be spread apart by at least a week, and optionally at greater intervals of time, such as one to several months.

The present invention also encompasses an immunogenic composition comprising both inactivated PEDV and inactivated PDCoV. Additionally, the immunogenic composition can comprise other swine antigens, including *Escherichia coli* and *Clostridium perfringens*, types A-D, the dosages of which would be equivalent to those found in the commercially-available vaccines, Gletvax® and Litterguard®. The vaccines can contain one or more adjuvants, and optionally one or more excipients, in an amount effective to elicit production of neutralizing antibodies in swine. The adjuvant preferably provides an oil-in-water emulsion with additional components. The immunogenic compositions of the invention protect swine from infection by both PEDV and PDCoV, and are effective in single doses, in two-dose programs, or in vaccination programs involving multiple doses, which may be spread apart by at least a week, and optionally at greater intervals of time, such as one to several months.

BRIEF DESCRIPTION OF THE FIGURES

FIGS. 1-3 depict certain aspects of optimized passaging of PEDV in Vero 76 cells based on detection of morphology of infected cells (USA/Colorado/2013 strain, SEQ ID NO: 7).

FIG. 1 shows PEDV-infected Vero cells with "bubble effect" caused by the virus.

FIG. 2 shows PEDV-infected Vero cells that evidence a surrounding "filmy layer".

FIG. 3 shows non-infected Vero cells, instead showing the effect of high trypsin concentration, but without PEDV infection.

FIG. 4 shows the nucleotide sequence for recent Spanish isolate Calaf14 corresponding to the spike protein (SEQ ID NO: 1)

FIG. 5 shows a comparison of amino acid sequence percent identities (spike protein) for various European and North American isolates.

FIG. 7 provides an identity scores table of complete encoding sequences of spike protein for three European PEDV isolates, CV777, Br1-87, and Calaf14.

FIG. 8 provides an identity scores table of complete spike protein amino acid for three European PEDV isolates, CV777, Br1-87 and Calaf14.

FIGS. 9A-9E show full amino acid sequence alignments for full length spike (S) proteins for European strains CV777, BR1-87 and Calaf14. (SEQ ID NOS: 6, 5 and 4, respectively). Starting at the amino terminus, corresponding to FIG. 9A, shown is, consecutively, amino acid sequence ending at, respectively, residues 250, 550, 850, 1150, then ending approximately at position 1383.

FIGS. 10A-10R show full encoding nucleotide sequence alignments for full length spike (S) proteins for European strains CV777, BR1-87 and Calaf14 (SEQ ID NOS: 3, 2 and 1, respectively). Starting at the amino terminus, corresponding to FIG. 10A, shown is, consecutively, nucleic acid residue sequence ending at, respectively, residues 240, 480, 720, 960, 1200, 1440, 1680, 1920, 2160, 2400, 2640, 3120, 3360, 3600, 3840, 4080, then ending approximately at position 4140.

BRIEF DESCRIPTION OF THE SEQUENCE LISTING

Figure 1:
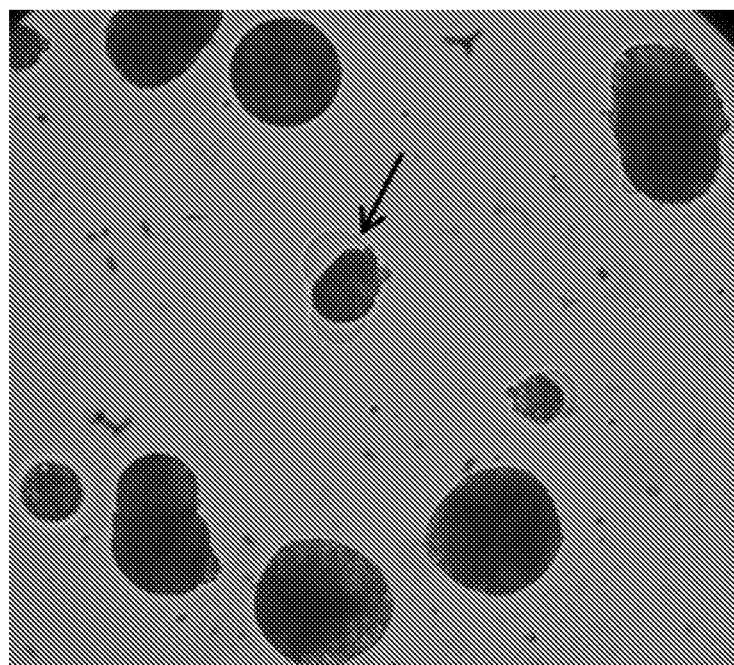

SEQ ID NO: 1 provides, as a DNA version, the nucleotide sequence encoding for the spike protein of PEDV strain Calaf14.

SEQ ID NO: 2 provides, as a DNA version, the nucleotide sequence encoding for the spike protein of PEDV strain Br1-87.

SEQ ID NO: 3 provides, as a DNA version, the nucleotide sequence encoding for the spike protein of PEDV strain CV777.

SEQ ID NO: 4 provides the amino acid sequence of spike protein of PEVD strain Calaf14.

SEQ ID NO: 5 provides the amino acid sequence of spike protein of PEVD strain Br1-87.

SEQ ID NO: 6 provides the amino acid sequence of spike protein of PEVD strain CV777.

SEQ ID NO: 7 provides, as a DNA version, the full nucleotide sequence encoding for the USA/Colorado/2013 PEDV virus.

SEQ ID NOS: 8-10 provide the nucleotide sequence of oligonucleotides used in cloning processes.

SEQ ID NO: 11 provides, as a DNA version, the full nucleotide sequence encoding for the USA/Indiana/2014/8501010 PDCoV virus.

SEQ ID NO: 12 provides, as a DNA version, the full nucleotide sequence encoding for the NVSL USA/Michigan/8977/2014 PDCoV virus.

DETAILED DESCRIPTION OF THE INVENTION

The present invention provides novel and efficacious vaccines useful to preventing disease caused by PEVD and PDCoV.

Definitions

Vaccines can be made more efficacious by including an appropriate adjuvant in the composition. The term "adjuvant" generally refers to any material that increases the humoral or cellular immune response to an antigen. Adjuvants are used to accomplish two objectives: They slow the release of antigens from the injection site, and they enhance stimulation of the immune system. Traditional vaccines are generally composed of a crude preparation of inactivated or killed or modified live pathogenic microorganisms. The impurities associated with these cultures of pathological microorganisms may act as an adjuvant to enhance the immune response. However, the immunity invoked by vaccines that use homogeneous preparations of pathological microorganisms or purified protein subunits as antigens is often poor. The addition of certain exogenous materials such as an adjuvant therefore becomes necessary. Further, in some cases, synthetic and subunit vaccines may be expensive to produce. Also, in some cases, the pathogen cannot be grown on a commercial scale, and thus, synthetic/subunit vaccines represent the only viable option. The addition of an adjuvant may permit the use of a smaller dose of antigen to stimulate a similar immune response, thereby reducing the production cost of the vaccine. Thus, the effectiveness of some injectable medicinal agents may be significantly increased when the agent is combined with an adjuvant.

Many factors must be taken into consideration in the selection of an adjuvant. An adjuvant should cause a relatively slow rate of release and absorption of the antigen in an efficient manner with minimum toxic, allergenic, irritating, and other undesirable effects to the host. To be desirable, an adjuvant should be non-viricidal, biodegradable, capable of consistently creating a high level of immunity, capable of stimulating cross protection, compatible with multiple antigens, efficacious in multiple species, non-toxic, and safe for the host (eg, no injection site reactions). Other desirable characteristics of an adjuvant are that it is capable of micro-dosing, is dose sparing, has excellent shelf stability, is amenable to drying, can be made oil-free, can exist as either a solid or a liquid, is isotonic, is easily manufactured, and is inexpensive to produce. Finally, it is highly desirable for an adjuvant to be configurable so as to induce either a humoral or cellular immune response or both, depending on the requirements of the vaccination scenario. However, the number of adjuvants that can meet the above requirements is limited. The choice of an adjuvant depends upon the needs for the vaccine, whether it be an increase in the magnitude or function of the antibody response, an increase in cell mediated immune response, an induction of mucosal immunity, or a reduction in antigen dose. A number of adjuvants have been proposed, however, none has been shown to be ideally suited for all vaccines. The first adjuvant reported in the literature was Freund's Complete Adjuvant (FCA) which contains a water-in-oil emulsion and extracts of *mycobacterium*. Unfortunately, FCA is poorly tolerated and it can cause uncontrolled inflammation. Since the discovery of FCA over 80 years ago efforts have been made to reduce the unwanted side effects of adjuvants.

Some other materials that have been used as adjuvants include metallic oxides (e.g., aluminum hydroxide), alum, inorganic chelates of salts, gelatins, various paraffin-type oils, synthesized resins, alginates, mucoid and polysaccharide compounds, caseinates, and blood-derived substances such as fibrin clots. While these materials are generally efficacious at stimulating the immune system, none has been found to be entirely satisfactory due to adverse effects in the host (e.g., production of sterile abcesses, organ damage, carcinogenicity, or allergenic responses) or undesirable pharmaceutical properties (e.g., rapid dispersion or poor control of dispersion from the injection site, or swelling of the material).

"Cellular immune response" or "cell mediated immune response" is one mediated by T-lymphocytes or other white blood cells or both, and includes the production of cytokines, chemokines and similar molecules produced by activated T-cells, white blood cells, or both; or a T lymphocyte or other immune cell response that kills an infected cell.

The term "emulsifier" is used broadly in the instant disclosure. It includes substances generally accepted as emulsifiers, e.g., different products of TWEEN® or SPAN® product lines (fatty acid esters of polyethoxylated sorbitol and fatty-acid-substituted sorbitan surfactants, respectively), and different solubility enhancers such as PEG-40 Castor Oil or another PEGylated hydrogenated oil.

"Humoral immune response" refers to one that is mediated by antibodies. "Immune response" in a subject refers to the development of a humoral immune response, a cellular immune response, or a humoral and a cellular immune response to an antigen. Immune responses can usually be determined using standard immunoassays and neutralization assays, which are known in the art.

"Immunologically protective amount" or "immunologically effective amount" or "effective amount to produce an immune response" of an antigen is an amount effective to induce an immunogenic response in the recipient. The immunogenic response may be sufficient for diagnostic purposes or other testing, or may be adequate to prevent signs or symptoms of disease, including adverse health effects or complications thereof, caused by infection with a disease agent. Either humoral immunity or cell-mediated immunity or both may be induced. The immunogenic response of an animal to an immunogenic composition may be evaluated, e.g., indirectly through measurement of antibody titers, lymphocyte proliferation assays, or directly through monitoring signs and symptoms after challenge with wild type strain, whereas the protective immunity conferred by a vaccine can be evaluated by measuring, e.g., reduction in clinical signs such as mortality, morbidity, temperature number, overall physical condition, and overall health and performance of the subject. The immune response may comprise, without limitation, induction of cellular and/or humoral immunity. "Immunogenic" means evoking an immune or antigenic response. Thus an immunogenic composition would be any composition that induces an immune response.

"Therapeutically effective amount" refers to an amount of an antigen or vaccine that would induce an immune response in a subject receiving the antigen or vaccine which is adequate to prevent or reduce signs or symptoms of disease, including adverse health effects or complications thereof, caused by infection with a pathogen, such as a virus or a bacterium. Humoral immunity or cell-mediated immunity or both humoral and cell-mediated immunity may be induced. The immunogenic response of an animal to a vaccine may be evaluated, e.g., indirectly through measurement of antibody titers, lymphocyte proliferation assays, or directly through monitoring signs and symptoms after challenge with wild type strain. The protective immunity conferred by a vaccine can be evaluated by measuring, e.g., reduction in clinical signs such as mortality, morbidity, temperature number, overall physical condition, and overall health and performance of the subject. The amount of a vaccine that is therapeutically effective may vary depending on the particular adjuvant used, the particular antigen used, or the condition of the subject, and can be determined by one skilled in the art.

"$TCID_{50}$" refers to "tissue culture infective dose" and is defined as that dilution of a virus required to infect 50% of a given batch of inoculated cell cultures. Various methods may be used to calculate $TCID_{50}$, including the Spearman-Karber method which is utilized throughout this specification. For a description of the Spearman-Karber method, see B. W. Mahy & H. O. Kangro, Virology Methods Manual, p. 25-46 (1996).

Vaccine & Immunogenic Compositions

The vaccine and immunogenic composition of the present invention induces at least one of a number of humoral and cellular immune responses in a subject swine that has been administered a vaccine composition of the invention. Generally, the vaccine compositions of the invention may be administered to swine of any age, whether male or female, irrespective of reproductive status, and although it is contemplated that a two-dose regimen will be most common, single dose and multiple dose vaccine treatments are also effective in the practice of the invention. A most preferred virus for use according to all aspects of the invention relating to PEDV is USA/Colorado/2013, whose sequence is deposited as GenBank accession No. KF272920, of the NCBI of the United States National Institutes of Health. Bethesda, MD (see SEQ ID NO:7 for encoding sequence as DNA).

A further preferred virus is Calaf14, as further discussed below (see SEQ ID NO: 1,4). Most preferred are viruses encoded from polynucleotide sequence having 99.0, 99.5, and 99.9% identity to the full encoding sequence for Calaf14 or the spike gene thereof.

A preferred virus for use according to all aspects of the invention relating to PDCoV is USA/Michigan/8977/2014, whose sequence is deposited as GenBank accession No. KM012168 (see SEQ ID NO: 12 for encoding sequence as DNA). Another preferred virus for use according to all aspects of the invention relating to PDCoV is USA/Indiana/2014/8501010 (see SEQ ID NO: 11 for encoding sequence as DNA).

GenBank® is the recognized US-NIH genetic sequence database, comprising an annotated collection of publicly available DNA sequences, and which further incorporates submlssions from the European Molecular Biology Laboratory (EMBL) and the DNA DataBank of Japan (DDBJ), see Nucleic Acids Research, January 2013,v 41(D1) D36-42 for discussion.

Viral Isolates

The adjuvanted vaccine compositions of the invention effectively incorporate all recognized strains or isolates of PEDV, including strains isolated from Europe, Asia and North America, including preferably all strains that have at least about 80% overall nucleotide identity to North American strain USA/Colorado/2013, deposited as GenBank accession No. KF272920 (see SEQ ID NO:7 for seed stock therefrom, shown as DNA copy). Preferably, the overall nucleotide homology is 70%, 80%, 90%, 95%, 96%, 97%, 98% or 99% or greater to USA/Colorado/2013, more preferably at least 95% or higher. Accordingly, additional representative strains useful in the practice of all aspects of the invention include, without limitation, strain SDCV/USA/Illinois121/2014; strain USA/Colorado/2013 deposited as GenBank accession No. KF272920; Chinese strain AH2012, deposited as GenBank accession No. KC210145; strain 13-019349, deposited as GenBank accession No. KF267450; strain CH-ZMDZY-11 deposited as GenBank accession No. KC196276; strain OH851 (Ohio); European strain CV777 (see R. Kocherhans et al., Virus Genes, vol 23(2), pp 137-144, 2001; and strains IA2013-KF452322 and IN2013-KF452323 (see G. Stevenson et al. J. Vet. Diagn. Invest., vol 25, pp. 649-654, 2013. Use of strain USA/Colorado/2013 deposited as GenBank accession No. KF272920 is preferred. Additional preferred strains, useful in the practice of all aspects of the invention, all being about 99% or higher identical to USA/Colorado/2013 deposited as GenBank Accession No. KF272920, include: GenBank Accessions KJ645688 (USA/Iowa96/2013); KJ645640 (USA/Oklahoma32/2013); KJ778615 (NPL-PEDv/2013); KJ645647 (USA/Minnesota4l/2013); KJ645637 ((USA/Kansas29/2013); KJ645639 (USA/Texas31/2013); KJ645666 (USA/Iowa70/2013); KJ645646 (USA/North-Carolina40/2013); KM189367 (PEDv ON-018); and KJ645669 (USA/Wisconsin74/2013).

According to the practice of the invention, isolates of PEDV useful in the manufacture of adjuvanted vaccines may also be compared to USA/Colorado/2013 (deposited as GenBank accession No. KF272920) on the basis of spike protein amino acid sequence. Those viral isolates having spike protein sequences that are at least 70%, 80%, 90%, 95%, 96%, 97%, 98% and 99% identical to that provided by KF272920, most preferably 95% or higher, are preferred in the practice of all aspects of the invention. Taking into account that AID56763 represents the GenBank (US NIH/NCBI) Accession number for the spike protein sequence encoded within KF272920, the following PEDV isolates (as identified by their spike protein accessions) are among the reported virus strains or isolates that are most preferred for use in all aspects of the present invention: AID56757.1; AHA38139.1; AGO58924.1; AHA38125.1; AIM47748.1; AID56895.1: AID5669.1: A1120255.1: AGG34694.1; AIE15986.1; AHG05730.1; AHG05733.1 (all being representative of those having above 99% identity to the USA/Colorado/2013 spike sequence), and further, AIC82397.1; AFL02631.1; AHB33810.1; AFQ37598.1; AGG34691.1; AFJ97030.1; AFR11479.1; and AEW22948.1 (all being representative of those having above 98% identity to the USA/Colorado/2013 spike sequence). As noted, the USA-PEDV isolate shown by complete nucleotide sequence as SEQ ID NO:7 is highly preferred as a vaccine for all aspects of the practice of the present invention.

Typically, in the case of adjuvanted vaccines, the virus component is killed, however those skilled in the art will recognize that certain adjuvants are compatible with a live virus vaccine.

It is also generally recognized that evolving strains of PEDV, such as INDELs, are often naturally attenuated compared to older prototype strains, and thus may be used as vaccines wherein the virus is live attenuated, or inactivated. Calaf14 is an example of such strains, where only minimal further passaging may be needed to provide a safe vaccine attenuate. Exemplary vaccine viruses of the invention therefor also include those that have 95, 96, 97, 98, 99 and most preferably 99.5% or higher sequence identify with Calaf14, whether measured amino acid or encoding nucleotide sequence, for the spike protein or based on the full viral sequence.

Besides the various PEDV strains that may be used in an adjuvanted vaccine, recombinant spike protein, including the S1 and/or S2 fragments thereof, may also be used in a vaccine. Spike protein or S1 or S2 fragments may also be employed as diagnostic antigens. Exemplary PEDV spike protein sequences include, but are not limited to, those provided as SEQ ID NOS: 4, 5 6 and as encoded from SEQ ID NO:7.

The adjuvanted vaccine compositions of the invention effectively incorporate all recognized strains or isolates of PDCoV, including strains isolated from North America, including preferably, but not necessarily limited to, all strains that have at least about 80% overall nucleotide identity to isolate KNU14-04, deposited as GenBank accession No. KM820765; isolate USA/IA/2014/8734, deposited as GenBank accession No. KJ567050; isolate HKU15 strain MI6148, deposited as GenBank accession No. KJ620016; isolate HKU15 strain MN3092, deposited as GenBank accession No. KJ584360; isolate HKU15 strain NE3579, deposited as GenBank accession No. KJ584359; isolate HKU15 strain PA3148, deposited as GenBank accession No. KJ584358; isolate HKU15 strain KY4813, deposited as GenBank accession No. KJ584357; isolate HKU15 strain SD3424, deposited as GenBank accession No. KJ584356; isolate HKU15 strain IL2768, deposited as GenBank accession No. KJ584355; isolate OhioCVM1/2014, deposited as GenBank accession No. KJ769231; isolate PDCoV/USA/Illinois121/2014, deposited as GenBank accession No. KJ481931; isolate PDCoV/USA/Ohio137/2014, deposited as GenBank accession No. KJ601780; isolate PDCoV/USA/Illinois136/2014, deposited as GenBank accession No. KJ601779; isolate PDCoV/USA/Illinois134/2014, deposited as GenBank accession No. KJ601778; isolate PDCoV/USA/Illinois133/2014, deposited as GenBank accession No. KJ601777; isolate HKU15 strain IN2847, deposited as GenBank accession No. KJ569769; isolate HKU15 strain OH1987, deposited as GenBank accession No. KJ462462; and isolate HKU15 strain HKU15-155, deposited as GenBank accession No. JQ065043.

Besides the various PDCoV strains that may be used in a vaccine, recombinant spike protein, including the S1 and/or S2 fragments, may also be used in a vaccine. Spike protein or S1 or S2 fragments may also be employed as diagnostic antigens. Exemplary spike protein sequences include, but are not limited to, those of PDCoV isolates USA/IA/2014/8734, USA/Michigan/8977/2014, and USA/Indiana/2014/8501010.

Culturing of Virus

Isolation and propagation of PEDV has been generally difficult. Initial studies using Vero cells for propagation in culture have only been partially effective, and have required a trypsin-containing medium, often with excessive cytopathic effect including cell fusion, synctia formation, and cell detachment (see, for example K. Kusangi et al., J. Vet Med Sci, vol. 54(2), pp. 313-318, 1992, and M. Hofmann et al. J. Clinical Microbiology, vol. 26(11), pp2235-2239, 1988). Accordingly, improved passaging methods were developed for the practice of the present invention. Details of this method are provided in Examples 1 and 2 below. It should be noted that both USA/Colorado/2013 and Calaf14 can be cultured in Vero cells.

Cultivation of PDCoV has also proven not to be a straightforward process. Trypsin-containing medium is also required for propagating PDCoV; however, not all cell lines tested supported growth of the virus. Swine testicular (ST) cells have proven to support replication of SDCoV, though, and are the preferred cell line for propagation of the virus. ST cells can be obtained, for example, from the American Type Culture Collection (ATCC), Manassas, VA, USA, under deposit number CRL-1746.

Inactivation of Virus (for Both PEDV and PDCov)

Inactivated or killed viral strains are those which have been inactivated by methods known to those skilled in the art, including treatment with formalin, betapropriolactone (BPL), binary ethyleneimine (BEI), sterilizing radiation, heat, or other such methods.

Adjuvant Component (for Both PEDV and PDCoV)

The vaccine compositions of the invention are preferably provided as emulsions, with adjuvant components provided from a combination of lecithin in light mineral oil, and also an aluminum hydroxide component. Details concerning the composition and formulation of Amphigen® (as representative lecithin/mineral oil component) are provided in Example 5 below, as are details concerning representative aluminum hydroxide components.

According to the practice of the invention, the oil used in the adjuvant formulations of the instant invention is a light mineral oil. As used herein, the term "mineral oil" refers to a mixture of liquid hydrocarbons obtained from petrolatum via a distillation technique. The term is synonymous with "liquefied paraffin", "liquid petrolatum" and "white mineral oil." The term is also intended to include "light mineral oil," i.e., oil which is similarly obtained by distillation of petrolatum, but which has a slightly lower specific gravity than white mineral oil. See, e.g., Remington's Pharmaceutical Sciences, 18th Edition (Easton, Pa.: Mack Publishing Company, 1990, at pages 788 and 1323). Mineral oil can be obtained from various commercial sources, for example, J. T. Baker (Phillipsburg, Pa.), USB Corporation (Cleveland, Ohio). Preferred mineral oil is light mineral oil commercially available under the name DRAKEOL®.

Typically, the oily phase is present in an amount from 50% to 95% by volume; preferably, in an amount of greater than 50% to 85%; more preferably, in an amount from greater than 50% to 60%, and more preferably in the amount of greater than 50-52% v/v of the vaccine composition. The oily phase includes oil and emulsifiers (e.g., SPAN® 80, TWEEN® 80 etc), if any such emulsifiers are present.

Non-natural, synthetic emulsifiers suitable for use in the adjuvant formulations of the present invention also include sorbitan-based non-ionic surfactants, e.g. fatty-acid-substituted sorbitan surfactants (commercially available under the name SPAN® or ARLACEL®), fatty acid esters of polyethoxylated sorbitol (TWEEN®), polyethylene glycol esters of fatty acids from sources such as castor oil (EMULFOR®); polyethoxylated fatty acid (e.g., stearic acid available under the name SIMULSOL® M-53), polyethoxylated isooctylphenol/formaldehyde polymer (TYLOXAPOL®), polyoxyethylene fatty alcohol ethers (BRIJ®); polyoxyethylene nonphenyl ethers (TRITON® N), polyoxyethylene isooctylphenyl ethers (TRITON® X). Preferred synthetic surfactants are the surfactants available under the name SPAN® and TWEEN®, such as TWEEN®-80 (Polyoxyethylene (20) sorbitan monooleate) and SPAN®-80 (sorbitan monooleate). Generally speaking, the emulsifier(s) may be present in the vaccine composition in an amount of 0.01% to 40% by volume, preferably, 0.1% to 15%, more preferably 2% to 10%.

In an alternative embodiment of the invention, the final vaccine composition contains SP-Oil® and Rehydragel® LV as adjuvants (or other Rehydragel® or Alhydrogel® products), with preferable amounts being about 5-20% SP-Oil (v/v) and about 5-15% Rehydragel LV (v/v), and with 5% and 12%, respectively, being most preferred amounts. In this regard it is understood that % Rehydragel refers to percent dilution from the stock commercial product. (SP-Oil @ is a fluidized oil emulsion with includes a polyoxyethylene-polyoxypropylene block copolymer (Pluronic® L121, BASF Corporation, squalene, polyoxyethylene sorbitan monooleate (Tween®80, ICI Americas) and a buffered salt solution.) In another embodiment of the invention, the final vaccine composition contains TXO as an adjuvant; TXO is generally described in WO 2015/042369. All TXO compositions disclosed therein are useful in the preparation of vaccines of the invention. In TXO, the immunostimulatory oligonucleotide ("T"), preferably an ODN, preferably containing a palindromic sequence, and optionally with a modified backbone, is present in the amount of 0.1 to 5 ug per 50 ul of the vaccine composition (e.g., 0.5-3 ug per 50 ul of the composition, or more preferably 0.09-0.11 ug per 50 ul of the composition). A preferred species thereof is SEQ ID NO: 8 as listed (page 17) in the WO2015/042369 publication. The polycationic carrier ("X") is present in the amount of 1-20 ug per 50 ul (e.g., 3-10 ug per 50 ul, or about 5 ug per 50 ul). Light mineral oil ("O") is also a component of the TXO adjuvant.

In certain embodiments, TXO adjuvants are prepared as follows:
a) Sorbitan monooleate, MPL-A and cholesterol are dissolved in light mineral oil. The resulting oil solution is sterile filtered;
b) The immunostimulatory oligonucleotide, Dextran DEAE and Polyoxyethylene (20) sorbitan monooleate are dissolved in aqueous phase, thus forming the aqueous solution; and
c) The aqueous solution is added to the oil solution under continuous homogenization thus forming the adjuvant formulation TXO.

It should be noted that the present invention may also be successfully practiced using wherein the adjuvant component is only Amphigen. All the adjuvant compositions of the invention can be used with any of the PEDV strains and isolates covered by the present Specification.

Excipients (for Both PEDV and PDCov)

The immunogenic and vaccine compositions of the invention can further comprise pharmaceutically acceptable carriers, excipients and/or stabilizers (see e.g. Remington: The Science and practice of Pharmacy (2005) Lippincott Williams), in the form of lyophilized formulations or aqueous solutions. Acceptable carriers, excipients, or stabilizers are nontoxic to recipients at the dosages and concentrations, and may comprise buffers such as phosphate, citrate, and other organic acids; antioxidants including ascorbic acid and methionine; preservatives (such as Mercury((o-carboxyphenyl)thio)ethyl sodium salt (THIOMERSAL), octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrans; chelating agents such as EDTA; sugars such as sucrose, mannitol, trehalose or sorbitol; salt-forming counter-ions such as sodium; metal complexes (e.g. Zn-protein complexes); and/or non-ionic surfactants such as polyethylene glycol (PEG), TWEEN or PLURONICS.

Dosing (for Both PEDV and PDCov)

A preferred clinical indication is for treatment of both breeding sows and gilts pre-farrowing. In a preferred example (applicable to both sows and gilts), two 2-ML doses of killed vaccine will be used, the first dose being administered as early as pre-breeding to 5-weeks pre-farrowing, with the second dose administered at about 1-3 weeks pre-farrowing. Doses of killed vaccine preferably provide an amount of viral material that would correspond to a $TCID_{50}$ (tissue culture infective dose) of between about $10^6$ and $10^8$, more preferably between about $10^7$ and $10^{7.5}$, if the virus were live, and can be varied, as is recognized in the art. Booster doses can be given two weeks prior to any subsequent farrowings. Intramuscular vaccination (all doses) is preferred, although one or more of the doses could be given subcutaneously, or less preferably, orally.

In a further preferred example, the sow or gilt is vaccinated intramuscularly at 5-weeks pre-farrowing and then 2-weeks pre-farrowing. Under these conditions (from about $TCID_{50}$ $10^7$ to about $10^{7.5}$, a protective immune response was demonstrated in PEDV-negative vaccinated sows in that they developed antibodies (measured via fluorescent focal neutralization titer from serum samples) with neutralizing activity, and these antibodies were passively transferred to their piglets. The protocols of the invention are also applicable to the treatment of already seropositive sows and gilts, and also piglets and boars. Although it is preferred to re-vaccinate a mother sow prior to any subsequent farrowings, the vaccine compositions of the invention nonetheless can still provide protection to piglets via ongoing passive transfer of antibodies, even if the mother sow was only vaccinated in association with a previous farrowing.

It should be noted that piglets may then be vaccinated as early as Day 1 of life. For example, piglets can be vaccinated at Day 1, with a booster dose at 3 weeks of age and re-boost every 6 months, if the parent sow was not vaccinated pre-breeding; however, if the sow was vaccinated pre-breeding, and thus the piglets receives maternal antibody through colostrums, then simply boost the piglets at 3 weeks and every 6 months. Boars (typically kept for breeding purposes) should be vaccinated once every 6 months.

Variation of the dose amounts is well within the practice of the art.

Methods of Use (for Both PDEV and PDCoV)

The invention encompasses methods of preventing PEDV virus infection comprising administering the immunogenic and vaccine compositions of the invention in a swine subject of any age.

When provided therapeutically, the vaccine is provided in an effective amount upon the detection of a symptom of actual infection. A composition is said to be "pharmacologically acceptable" if its administration can be tolerated by a recipient. Such a composition is said to be administered in a "therapeutically or prophylactically effective amount" if the amount administered is physiologically significant.

At least one vaccine or immunogenic composition of the present invention can be administered by any means that achieve the intended purpose, using a pharmaceutical composition as described herein. For example, route of administration of such a composition can be by parenteral, oral, oronasal, intranasal, intratracheal, topical, subcutaneous, intramuscular, transcutaneous, intradermal, intraperitoneal, intraocular, and intravenous administration. In one embodiment of the present invention, the composition is administered by intramuscularly. Parenteral administration can be by bolus injection or by gradual perfusion over time. Any suitable device may be used to administer the compositions, including syringes, droppers, needleless injection devices, patches, and the like. The route and device selected for use will depend on the composition of the adjuvant, the antigen, and the subject, and such are well known to the skilled artisan.

According to the present invention, an "effective amount" of a vaccine or immunogenic composition is one which is sufficient to achieve a desired biological effect, in this case at least one of cellular or humoral immune response to one or more strains of PEDV. It is understood that the effective dosage will be dependent upon the age, sex, health, and weight of the subject, kind of concurrent treatment, if any, frequency of treatment, and the nature of the effect desired. The ranges of effective doses provided below are not intended to limit the invention and represent examples of dose ranges which may be suitable for administering compositions of the present invention. However, the dosage may be tailored to the individual subject, as is understood and determinable by one of skill in the art, without undue experimentation.

EXAMPLES

The following examples illustrate only certain and not all embodiments of the invention, and thus, should not be viewed as limiting the scope of the invention.

Example 1: Protocol for Extraction of PEDV Virus from Tissue Samples

Approximately 1 cm of tissue was used for extraction of PEDV virus. The tissue was chopped into fine pieces using a sterile scalpel and sterile scissors in a sterile Petri dish. Work was done in a Bio-safety cabinet to ensure aseptic conditions. 2 ml of sterile PBS was added to the Petri dish to collect tissue and material was transfer to a 15 ml conical tube. Tissue was homogenized using a Qiagen TissueRuptor at 80% of maximum by pulsing for a total of 30 seconds. Homogenization was performed in an ice bucket to lessen the effect of heat on the PEDV virus. The homogenized material was filtered through a 0.45 uM filter and 60 ul of material was used for RNA isolation and PEDV Q-PCR to confirm the presence of the PEDV virus. The filtered material containing the PEDV virus was further diluted 1:10 in sterile PBS and then filtered through a 0.20 uM filter.

Figure 2:
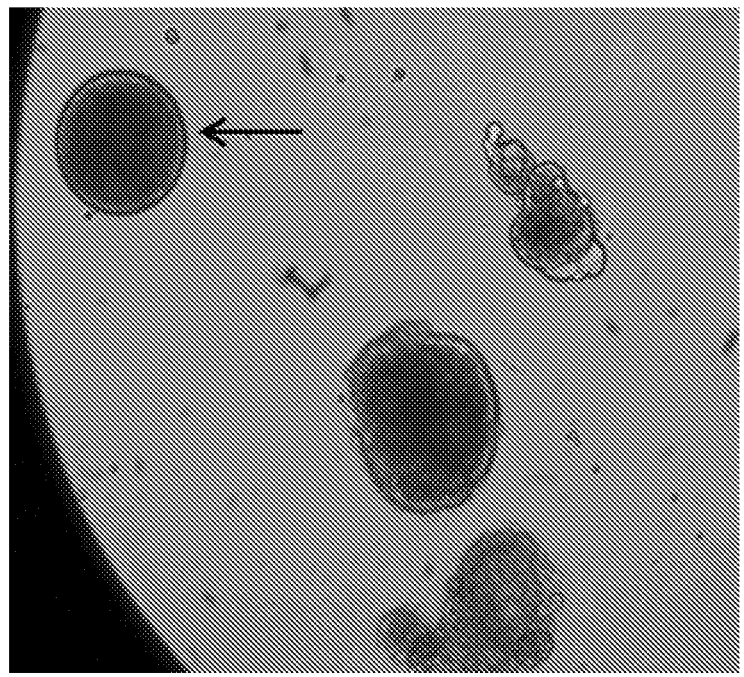

The sterile-filtered PEDV homogenate was used to infect confluent mono-layers of Vero 76 cells by transferring 1 ml of filtered material to a T-25 flask containing 2.8E+06 cells planted 3 to 4 days prior. The T-25 flasks of confluent Vero 76 cells were washed 2× with sterile PBS and 1× with DMEM media containing 10% TPB, 20 ug/ml geneticin and 4 ug/ml TPCK trypsin (equivalent to 18.8 USP units/ml). Cells were infected for 1 hour at 37° C. and 5% $CO_2$ in an incubator with gentle swirling every 15 minutes to ensure virus was evenly distributed to all cells. 5 ml of DMEM media containing 10% TPB, 20 ug/ml geneticin and 4 ug/ml TPCK trypsin (equivalent to 18.8 USP units/ml) was added to flasks and flask were allowed to incubate 2 days. After 2 days, flasks were frozen at −80° C. and thawed at 37° C. This material is considered as Passage 1 of the virus. One milliliter of the total volume from the flask was then used for Passage 2 of the virus. The 1 ml of Passage 1 material is used to infect a T-25 flask containing 2.8E+06 cells seeded 3 to 4 days prior. Cells were first washed 2× with sterile PBS and 1× with DMEM media containing 10% TPB, 20 ug/ml geneticin and 4 ug/ml TPCK trypsin (equivalent to 18.8 USP units/ml). Cells were infected for 1 hour at 37° C. and 5% $CO_2$ in an incubator with gentle swirling every 15 minutes to ensure virus was evenly distributed to cells. 5 ml of DMEM media containing 10% TPB, 20 ug/ml geneticin and 4 ug/ml TPCK trypsin (equivalent to 18.8 USP units/ml) was added to flasks and flask were allowed to incubate for 2 days. This material is Passage 2 of the PEDV virus. Passages are repeated every 2 days until the cells show signs of infection indicated by clusters of cells surrounded by a filmy layer of material and/or a bubble effect on the clustered cells (see FIGS. 1-3). The appearance of PEDV infected cells was confirmed by a decrease in Ct value in the PEDV Taqman assay. The PEDV-infected cells have a rounded up appearance with a layer of shiny film surrounding the rounded up cells.

Example 2: Master Seed Production with Strain USA/Colorado/2013

Porcine Epidemic Diarrhea Virus Isolate PEDv-1 CO-2013 originated from a swine diagnostic specimen sourced from Colorado in 2013 and was acquired by the National Veterinary Services Laboratories in Ames, IA. (GenBank accession No. KF272920). The virus was propagated in Vero 76 cells to passage 5. The virus was then subjected to three rounds of limited dilution cloning in order to obtain a clonal population. Master seed stocks were then prepared. Extraneous agent, sterility, and *Mycoplasma* testing of the PEDV were conducted in accordance with 9 CFR Part 113.55, Part 113.27 and Part 113.28, respectively. The Vero cell line was designated Vero MCS Cells may be used from the MCS up to MCS+20.

For media formulation (for uninoculated cell growth medium), using a roller bottle or bioreactor production process, the cell growth medium is OPTIMEM, DMEM or equivalent cell culture media supplemented with up to 1% glutamine and 0.5 to 3% glucose, and 0.5 to 5% gamma-irradiated fetal bovine serum. Gentamicin is added at a final concentration of 20-30 µg/mL (or as determined by vaccine development experiments). For virus production medium, again for the roller bottle or bioreactor production process, the cell growth medium is OPTIMEM, OPTIPRO or equivalent supplemented with up to a 1% glutamine, >2 Units/literof 2x bovine or porcine trypsin, and 0.5 to 3% glucose. Gentamicin is added at a final concentration of 20-30 µg/mL (or as determined by vaccine development experiments). Roller bottles and bioreactors can be rinsed with cell growth medium (OPTIMEM, OPTOPRO or equivalent) up to 3×prior to infection.

Example 3: Propagation and Harvest

Plastic flasks or roller bottles are used for growing and expanding cell cultures. Roller bottles or bioreactors will be used for virus propagation. Cells may be washed, to remove serum, prior to inoculation with virus. The virus may be diluted in virus production medium and added directly to the cell monolayer. When bioreactors are used for virus propagation, trypsinized cells will be removed from the roller bottles and a final cell passage grown in uninoculated cell growth medium. Microcarriers for the bioreactors are prepared. The seed virus is diluted to an appropriate volume within a multiplicity of infection (MOI) range of 0.0001 to 10.0

The PED virus causes observable cytopathic effect (CPE). Virus is harvested when viral-induced CPE has reached 50-100% and infected cells have begun sloughing off into the medium (cell monolayer loss exceeding 50%). The roller bottle vessels are removed from the incubator and inspected microscopically for both CPE and evidence of microbial contamination. Following the examination, the antigen fluid is harvested into appropriate sterile containers in an aseptic manner. Bioreactor fluids are examined microscopically for evidence of microbial contamination and for the presence of desired cytopathic effects (CPE). A representative seed stock result is reported as SEQ ID NO:7, as DNA)

Following examination, the viral fluids are passed through a ≤100 micron filter or stainless steel mesh screen to remove microcarriers and harvested into appropriate sterile containers in an aseptic manner. Fluids may be stored at 2° C.-7° C. for a maximum of 24 hours until inactivation. The harvested fluids may be used for seed if it is at the proper passage level and has an acceptable infectivity titer.

Example 4: Inactivation and Neutralization

Acceptable harvested antigen production fluids will be pooled into suitable inactivation containers and inactivated using a 5 mM binary ethylenimine (BEI) solution. The mixture is cyclized for 60-80 minutes at 36±2° C. Following the addition of inactivant, the antigen will be thoroughly mixed and transferred to an inactivation vessel for the duration of the process (≥48 hours, with agitation). Neutralization of the inactivated antigen fluids will be facilitated through the addition of sterile 1 M Sodium Thiosulfate to a final concentration of approximately 20 mM-25 mM. Post-inactivated/neutralized antigen production fluids will be tested for sterility and completeness of inactivation and stored at 2-7° C. for future use in vaccine serial formulation. Genatamicin can then be used as preservative. This antibiotic will be added at the lot stage. The concentration of gentamicin in the final product will be ≤30 µg/mL.6.

Example 5: Adjuvant Compositions and Formulation

A preferred adjuvanted vaccine composition was assembled as follows. The killed vaccine provides 7.8 $\log_{10}TCID_{50}$ of killed USA/Colorado/2013 virus per 2 ML dose in a buffered solution further comprising about 5% (v/v) Rehydragel® (aluminum hydroxide gel) and "20% Amphigen" @ at about 25% final (v/v). Doses down to 7.0 $\log_{10}TCID_{50}$ of killed USA/Colorado/2013 are also preferred.

Amphigen® is generally described in U.S. Pat. No. 5,084,269 and provides de-oiled lecithin (preferably soy) dissolved in a light oil, which is then dispersed into an aqueous solution or suspension of the antigen as an oil-in-water emulsion. Amphigen has been improved according to the protocols of U.S. Pat. No. 6,814,971 (see columns 8-9 thereof) to provide a so-called "20% Amphigen" component for use in the final adjuvanted vaccine compositions of the present invention. Thus, a stock mixture of 10% lecithin and 90% carrier oil (DRAKEOL®, Penreco, Karns City, PA) is diluted 1:4 with 0.63% phosphate buffered saline solution, thereby reducing the lecithin and DRAKEOL components to 2% and 18% respectively (i.e. 20% of their original concentrations). Tween 80 and Span 80 surfactants are added to the composition, with representative and preferable final amounts being 5.6% (v/v) Tween 80 and 2.4% (v/v) Span 80, wherein the Span is originally provided in the stock DRAKEOL component, and the Tween is originally provided from the buffered saline component, so that mixture of the saline and DRAKEOL components results in the finally desired surfactant concentrations. Mixture of the DRAKEOL/lecithin and saline solutions was accomplished using an In-Line Slim Emulsifier apparatus, model 405, Charles Ross and Son, Hauppauge, NY, USA.

The vaccine composition also includes Rehydragel® LV (about 2% aluminum hydroxide content in the stock material), as additional adjuvant component (available from Reheis, NJ, USA, and ChemTrade Logistics, USA). With further dilution using 0.63% PBS, the final vaccine composition contains the following compositional amounts: 7.8 $\log_{10}TCID_{50}$ of killed USA/Colorado/2013 virus per 2 ML dose; 5% (v/v) Rehydragel® LV; 25% (v/v) of "20% Amphigen", i.e. it is further 4-fold diluted); and 0.01% (w/v) of merthiolate.

As is understood in the art, the order of addition of components can be varied to provide the equivalent final vaccine composition. For example, an appropriate dilution of killed virus in buffer can be prepared. An appropriate amount of Rehydragel® LV (about 2% aluminum hydroxide content) stock solution can then be added, with blending, in order to permit the desired 5% (v/v) concentration of Rehydragel® LV in the actual final product. Once prepared, this intermediate stock material is combined with an appropriate amount of "20% Amphigen" stock (as generally described above, and already containing necessary amounts of Tween 80 and Span 80) to again achieve a final product having 25% (v/v) of "20% Amphigen". An appropriate amount of 10% merthiolate can finally be added.

The vaccinate compositions of the invention permit variation in all of the ingredients, such that the total dose of antigen may be varied preferably by a factor of 100 (up or down) compared to the antigen dose stated above, and most preferably by a factor of 10 or less (up or down). Similarly, surfactant concentrations (whether Tween or Span) may be varied by up to a factor of 10, independently of each other, or they may be deleted entirely, with replacement by appropriate concentrations of similar materials, as is well understood in the art.

Rehydragel® concentrations in the final product may be varied, first by the use of equivalent materials available from many other manufacturers (i.e. Alhydrogel®,Brenntag; Denmark), or by use of additional variations in the Rehydragel® line of products such as CG, HPA or HS. Using LV as an example, final useful concentrations thereof including from 0% to 20%, with 2-12% being more preferred, and 4-8% being most preferred, Similarly, the although the final concentration of Amphigen (expressed as % of "20% Amphigen") is preferably 25%, this amount may vary from 5-50%, preferably 20-30% and is most preferably about 24-26%.

Other embodiments and uses of the invention will be apparent to those skilled in the art from consideration of the specification and practice of the invention disclosed herein. All references cited herein, including all publications, U.S. and foreign patents and patent applications, are specifically and entirely incorporated by reference. It is intended that the specification and examples be considered exemplary only with the true scope and spirit of the invention indicated by the following claims.

Example 6: Cross Protection

Figure 6:
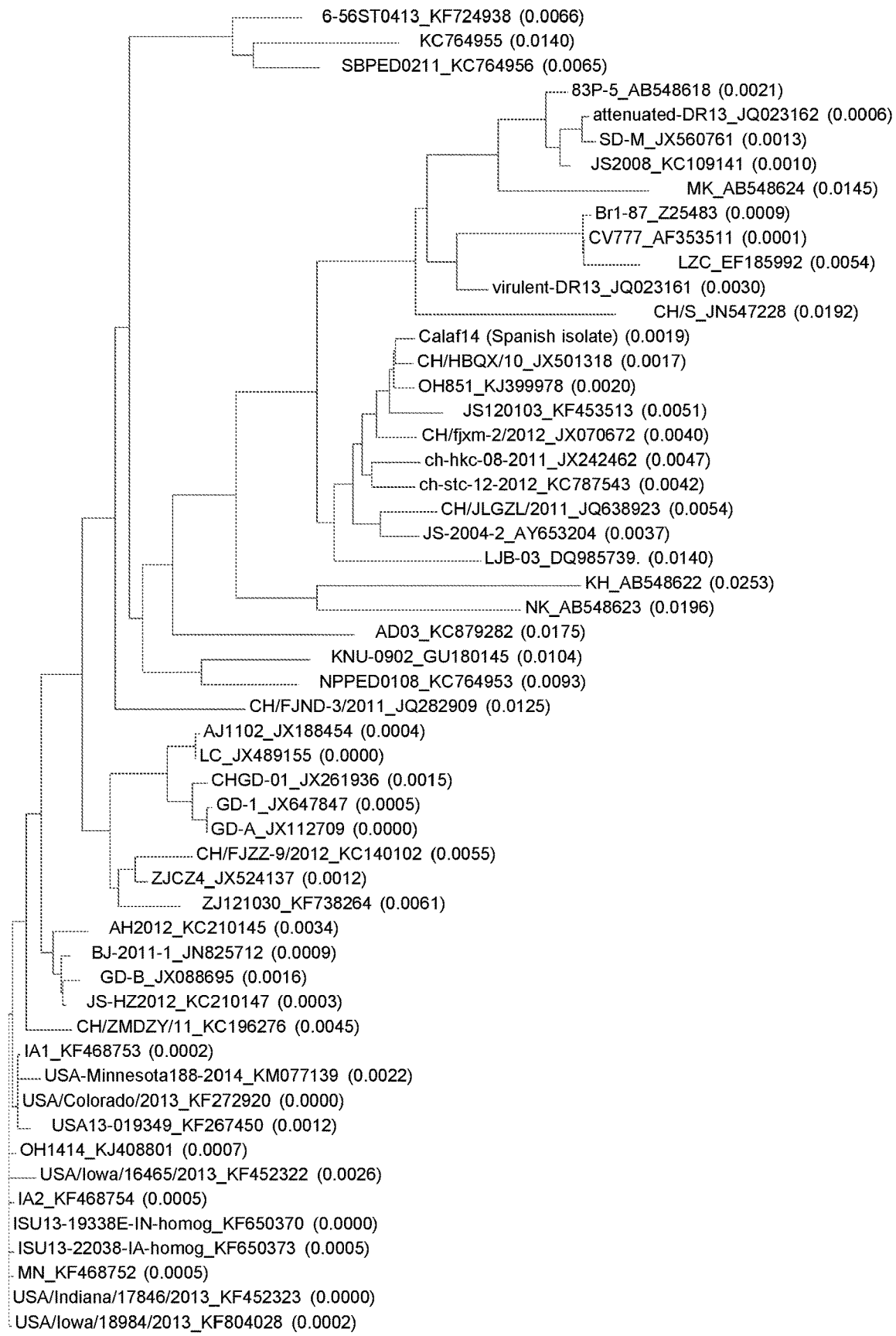
FIG. 6 shows a phylogenetic tree of numerous known PEDV isolates based on spike protein, as identified by their depository record locators.

Porcine Epidemic Diarrhea virus (PEDV) was initially introduced in the United States in April 2013 and subsequently spread all over the country. Sequencing of PEDV isolates revealed similar nucleotide homology (>99%) with a Chinese strain from 2012. In Europe, several outbreaks have been reported since 2014, which are different than prior European outbreaks. The new European strains cluster with the INDEL (insertion-deletion) variants of the PEDV phylogenetic tree (FIG. 6), and warrant significant epidemiological attention.

In order to assess efficacy of an inactivated porcine epidemic diarrhea virus vaccine in pregnant sows, the following experiments were conducted. Strain USA/Colorado/2013 (deposited as GenBank accession No. KF272920) was used, and cultured and prepared as provided for above. The "Porcine Epidemic Diarrhea Vaccine, Killed Virus", manufactured by Zoetis, is intended for pre-farrowing vaccination of sows and gilts against diarrheal disease in their neonatal pigs caused by PEDV. This vaccine was developed using a highly virulent American PEDV strain. In a preferred example, the vaccine is given intramuscularly to pregnant sows as two doses, 2 ML each, three weeks apart, at five and two weeks pre-farrowing.

The objective of the study was to determine the immunogenic efficacy of this killed vaccine, by infecting 4 day old piglets born from vaccinated pregnant sows with a new Spanish PEDV isolate (Calaf14), characteristic of recent European outbreaks, as challenge. An efficacy study of the vaccine in pregnant sows was required to evaluate the maternal antibody protection against Porcine Epidemic Diarrhea virus, since PEDV induces gastro-intestinal disease, and protection against infection and disease against PEDV is mediated by maternally-derived antibodies.

Eight pregnant sows were included in the study. At 5 weeks before farrowing, a dose (IM route) of an experimental batch of the inactivated PEDV vaccine was administered to 5 sows; 3 sows remained non-vaccinated. Three weeks later, vaccinated sows received a second dose. After farrowing, approximately at 4±1 days of age, all piglets were challenged with the Spanish PEDV strain Calaf14 (encoding nucleotides, as DNA, and amino acid sequence for spike protein thereof, are reported as SEQ ID NOS: 1 and 4 respectively), isolated from recent cases of diarrhea in neonatal pigs, and clustered with the PEDV INDEL variants. Three to four days post-challenge, all piglets were euthanized and necropsied. Twice daily after challenge, all piglets were evaluated for the presence of clinical signs, rectal temperature, body weight, and fecal swabs were taken to perform a PEDV-specific RT-qPCR. At day 3 to 4 after challenge, all piglets were euthanized, and gut tissue samples were taken.

Vaccinated sows delivered a total of 32 piglets, while control sows delivered 21 piglets. In control sows, moderate to severe diarrhea was observed in all litters, affecting 19 out of 21 piglets (90.5%). Weight loss during the study affected 12/21 piglets (57.1%), and 4 of them reached the end-point of dehydration and severe gastrointestinal clinical signs and had to be euthanized. In contrast, in vaccinated sows, 3 out of 5 litters were either non-affected by diarrhea, or only one pig in the litter was mildly affected in one single observation; in two litters, several piglets developed mild to moderate diarrhea. In total, 15 piglets born from vaccinated mothers developed diarrhea (46.9%). Weight loss was observed in only 3/32 piglets (6.5%), and none of the piglets had to be euthanized.

The clinical data obtained confirm that the Porcine Epidemic Diarrhea Vaccine, Killed Virus, manufactured by Zoetis, containing a killed US PEDV isolate as antigen, is able to confer cross-protection to piglets born from vaccinated sows, in front of the challenge with a heterologous EU PEDV isolate.

The European Challenge Virus (Spanish isolate Calaf14) was compared to two known and older European isolate on the basis of full spike protein coding sequence. The "Calaf 14" Spanish isolate was obtained from a PEDV case detected in a Spanish farm in 2014. Intestines from a 4-day-old piglet were processed to obtain a clarified intestine homogenate. RNA was extracted and the sample was found to be positive by real-time RT-PCR analysis (PEDV N gene-based real-time RT-PCR assay).

The complete spike (S) gene (4152nt) was sequenced as previously described (Chen, Q., et al. "Isolation and characterization of porcine epidemic diarrhea viruses associated with the 2013 disease outbreak among swine in the United States." J Clin Microbiol 52(1): 234-243 2014). The complete S gene coding sequence of the Calaf14 PEDV (SEQ ID NO:1) currently circulating isolate was compared to those of the two PEDV European reference isolates (CV777, see SEQ ID NO: 3 and Br1/87, see SEQ ID NO:2) available in the GenBank (accession numbers AF353511 and Z25483 respectively). No sequences are published or available in GenBank from the most recent outbreaks occurred in other European countries. For the alignment, both Vector NTI Advance 11.5 and CLUSTAL 2.1 multiple sequence alignment were used. Analysis showed that the two European isolates were practically identical to each other (99.9% nucleotide identity, see Appendix 1). However, when compared to Calaf14 isolate identity scores decreased to 95.71% identity for Br1/87 and 95.81% identity with CV777 isolate (see FIG. 7).

Complete S predicted protein sequences (1383 amino acids) were generated for the three isolates (SEQ ID NOS 4, 5 and 6) using Vector NTI Advance 11.5 software. Protein sequences were aligned using both Vector NTI Advance 11.5 and CLUSTAL 2.1 multiple sequence alignment. No insertions or deletions were detected when Calaf14 S protein (SEQ ID NO:4) was compared to CV777 (SEQ ID NO:6) and Br1/87 (SEQ ID NO:5) European isolates proteins. Nevertheless, analysis showed that identity between the two European reference isolates was of 99.71% whereas Calaf14 S protein showed a 95.81% of identity to Br1/87 and 96.1% to CV777 S protein (See FIG. 8).

It should be noted that Calaf14 is also an excellent strain from which to provide a vaccine (whether attenuated live or killed, in both cases either with or without adjuvant) that protects against PEDV challenge and disease, irrespective of whether the disease/challenge PEDV is: (1) of Asian origin including of INDEL types; (2) of European origin, when the European strain is a prototype strain such as was first detected in the 1970's or is any recently emerging strain, for example similar to North American INDELs; or (3) of North American origin, when the North American strain is a prototype strain, such as was first detected in 2013, or is reflective of emerging North American strains, such as INDELs; or (4) when the disease threat is posed by any combination of Asian, North American and European strains as disclosed herein.

The Calaf14 strain may be provided for use as a killed vaccine, following, for example, the preparatory methods described herein or other methods known in the art, to optionally include an adjuvant such as those adjuvant compositions described in the present specification. The Calaf14 strain may also be provided as an attenuated (i.e. modified) live vaccine, with or without an adjuvant, although those skilled in the art will recognize that only certain adjuvants are compatible with maintaining the viability of the live vaccine virus. Attenuation of the Calaf14 virus for a live vaccine so that it is insufficiently pathogenic to substantially harm the vaccinated target animal may be accomplished by known procedures, typically by serial passaging, as is recited in any of the following references which provide for attenuation of coronaviruses: B. Neuman et al., Journal of Virology, vol. 79, No. 15, pp. 9665-9676, 2005; J. Netland et al., Virology, v 399(1), pp. 120-128, 2010; Y-P Huang et al., "Sequence changes of infectious bronchitis virus isolates in the 3' 7.3 kb of the genome after attenuating passage in embryonated eggs, Avian Pathology, v. 36 (1), (Abstract), 2007; and S. Hingley et al., Virology, v. 200(1) 1994, pp. 1-10. It has also been generally disclosed that INDEL-type strains are often less virulent toward swine (including sows and piglets) compared to prototype PEDV strains, thus permitting Calaf14 to be used as a live vaccine with little or no attenuation.

Generally speaking, it is also within the practice of the present invention to provide vaccines containing more than one PEDV isolate, whether the vaccine is a live or killed vaccine, and/or to vaccinate animals proximally in time with more than one vaccine composition to thus deliver more than one PEDV isolate as antigen. Representative combination vaccines (killed or live) of the invention include (a) use of Calaf14 with CV777 and/or Br1/87 European isolate, or other European isolate(s) whether prototype or emerging; (b) use of Calaf14 in combination with North American USA/Colorado/2013 GenBank No. KF272920, or any other North American prototype(s) and/or emerging North American (INDL) strain(s), (c) use of Calaf 14 with any Asian strain, and (d) use of Calaf14 with all combinations of the foregoing. Further all such multiple combinations may be further combined with a modified live (attenuated) or killed PDCoV virus.

Example 7: Cross Protection Against European Strains, Additional Trial Results

The Porcine Epidemic Diarrhea Vaccine, Killed Virus, manufactured by Zoetis, is intended for pre-farrowing vaccination of sows and gilts against diarrheal disease in their neonatal pigs caused by PEDV. This killed vaccine was developed using a highly virulent American PEDV strain (USA/Colorado/2013) to be administered to intramuscularly to pregnant sows in two ml doses three weeks apart at 5 and 2 weeks pre-farrowing.

The objective of the study was to determine the immunogenicity of this vaccine, by infecting 4-6 day old piglets born from vaccinated pregnant sows with a new Spanish PEDV live isolate, Calaf14, as challenge. An efficacy study of the vaccine in pregnant sows was required to evaluate the maternal antibody protection against Porcine Epidemic Diarrhea virus, since PEDv induces gastro-intestinal disease, and protection against infection and disease against PEDv is mediated by maternally-derived antibodies. See Table 1 Ai B for design.

A total of 31 piglets born from sows vaccinated with the Inactivated PEDV vaccine (T02) and 21 from sows vaccinated with the placebo (T01) were included in the study. All piglets were challenged with the PEDV Spanish isolate at the age of 4 or 6 days. No mortality associated to PEDV challenge was detected in piglets from inactivated PEDV vaccine vaccinated sows (T02) whereas 23.8% challenge-associated mortality was reported for piglets from placebo vaccinated sows (T01).

After challenge, mild to severe digestive disorders including vomiting and aqueous yellow diarrhea were reported in 90.5% of piglets from placebo vaccinated sows; in piglets from PEDV killed virus vaccinated sows digestive disorders were observed in 48.4% of the piglets and ranged from mild to moderate. After challenge, 66.7% of piglets from placebo vaccinated sows experienced a mild to severe loss of general physical condition and/or dehydration whereas these signs were reported in only 3.2% of piglets from PEDV killed virus vaccinated sows and only mild dehydration was observed in these animals.

Body weight loss was detected ever after challenge in 42.9% of piglets from placebo vaccinated sows, ranging from mild to severe, whereas it was detected in 6.5% of animals from PEDV killed virus vaccinated sows as a mild degree.

Summary and frequency distribution of PEDV related clinical signs recorded after challenge with an heterologous PEDV strain (Spanish isolate, Calaf14) suggest that maternal antibody derived protection was obtained for piglets born from vaccinated sows with the PEDV inactivated vaccine. In conclusion, results suggest that the PEDV inactivated vaccine containing a US PEDV isolate as an antigen, is able to confer partial cross-protection to piglets born from vaccinated sows, in front of the challenge with an heterologous new PEDV Spanish isolate. Therefore, results suggest the suitability of the PEDV Vaccine, Killed Virus, manufactured by Zoetis, containing a US PEDV isolate as an antigen, to reduce the impact of an outbreak produced by new EU PEDV isolates.

TABLE 1A

Vaccination phase

| Treatment | Treatment Description | Dosage | Route of Admin | Day(s) of Admin | Animals per Treatment |
|---|---|---|---|---|---|
| T01 | Control (Adjuvant Placebo) | 2 ml | IM | 0 and 21 | 3 |
| T02 | Vaccine (PEDV-1 CO 2013 (PEDV-1 CO 2013 Killed Virus) | 2 ml (Pre-inactivation titer of 7.5 TCID50/dose) | IM | 0 and 21 | 5 |

At 5 weeks before the expected farrowing date, a dose of the CP was administered to T01 sows by IM route, and they were revaccinated 3 weeks later. Also, 5 weeks before the expected date farrowing a dose of the IVP was administered to T02 sows by IM route, and they were revaccinated 3 weeks later.

TABLE 1B

Challenge phase

| Treatment group | Treatment Description | Dosage | Route of Admin | Day of Challenge (DC) | End of Study | Animals per Treatment |
|---|---|---|---|---|---|---|
| T01 | PEDV Calaf14 Spanish isolate | 10 ml of a $10^{-3}$ dilution of intestinal homogenate stock (estimated $10^2$-$10^3$ PEDV genome copies) | Esophageal gavage | 4-6 day-old | 3-4 days post-challenge | All piglets from each litter |
| T02 | PEDV Calaf14 Spanish isolate | 10 ml of a $10^{-3}$ dilution of intestinal homogenate stock (estimated $10^2$-$10^3$ PEDV genome copies) | Esophageal gavage | 4-6 day-old | 3-4 days post-challenge | All piglets from each litter |

At 4 to 6 days of age all pigs from each litter were challenged with PEDv Calaf14 and 3 to 4 days post-challenge (end of the study), they were euthanized and necropsied.

Definition of Day 0: Day 0 was established as the day of first vaccination (5 weeks pre-farrowing). "IVP" means the experimental vaccine product, i.e. the Colorado 2013 killed material, as formulated above. CP means the control material (adjuvants plus diluent) without virus/viral antigen.

Randomization: Sows were grouped in two batches according to the expected farrowing date. Batch-1 included three sows and Batch-2 five. Sows from each batch were randomly allocated to experimental groups according to local internal procedures (function "random" of Microsoft Excel program: random number assigned to each animal, re-ordered in decreasing order, and sequential distribution to treatment group).

Vaccine: As aforementioned, the vaccine used is Zoetis PEDV vaccine, killed virus, "PEDV CO 2013 (NVSL)" adjuvanted with 5% Rehydragel and 5% Amphigen, and was formulated based on a pre-inactivation titer at 7.2 $TCID_{50}$/mL (i.e. 7.5 $TCID_5$/dose) for use as 2 ML intramuscular doses. Control vaccine material contained 5% Rehydragel and 5% Amphigen formulated with diluent rather than PEDv antigen. Vaccinations were conducted intramuscularly at Day 0 (right side of neck) and at Day 21 (left side of neck).

Further information concerning the challenge material: The challenge material was recovered from a clarified intestinal homogenate from a neonate piglet on a local Spanish farm, and was diluted just prior to inoculation to achieve an appropriate concentration, i.e. a targeted titer is $10^7$ to $10^8$ PEDV genome copies/10 mL dose, requiring an approximate 1000-fold dilution of intestinal homogenate, with the 10 ML dose being administered by esophageal gavage (virus named Calaf14).

PEDV Disease-Related Mortality

When mortality was due to clinical signs associated to PEDV disease, it was summarized as challenge related mortality. Results are detailed below in Table 2.

From a total of 21 piglets from T01, 5 were euthanized due to PEDV related clinical signs, thus 23.8% challenge associated mortality was reported for T01 treatment group. No pigs died or were euthanized due to signs consistent with another disease.

No mortality associated to PEDV challenge was detected in T02 treatment group.

TABLE 2

PEDV challenge related mortality: number and % of Animals for Each Treatment

| | PEDV challenge related? | | | | total observations |
|---|---|---|---|---|---|
| | NO | | YES | | |
| treatment number | number | % | number | % | number |
| T01 | 16 | 76.2 | 5 | 23.8 | 21 |
| T02 | 31 | 100.0 | 0 | 0.0 | 31 |
| total observations | 47 | 90.4 | 5 | 9.6 | 52 |

General physical condition and dehydration, digestive disorders, temperature, weight loss, depression and appetite loss were clinical signs associated to PEDV disease thus considered related to challenge, and are compiled in Table 3. Digestive disorders including vomiting and aqueous yellow diarrhea were reported in 90.5% of animals from treatment group T01 whereas it was observed in 48.4% of T02 group piglets. One case from T01 experienced severe digestive disorders reaching the end point criteria that justified its euthanasia for welfare reasons. After challenge, 66.7% of piglets from treatment group T01 experienced a loss of general physical condition and/or dehydration whereas it was reported in only 3.2% of piglets from T02. Reported dehydration for T01 piglets ranged from mild to severe (1 to 3 reported scores) and only mild dehydration was reported in one piglet from T02. None of the piglets from treatment group T02 experienced a loss of appetite ever after challenge whereas 14.3% (3 out of 21) of piglets from T01 did. Weight loss was defined as secondary efficacy variable. Depression was observed after challenge in 66.7% of piglets from treatment group T01. Depressive status ranged from mild to moderate. Depression was also observed in 9.7% of piglets from T02. Abnormal temperature values ($T^a$>40.5° C. or $T^a$<37.0° C.) were recorded ever after challenge in 9.5% of piglets from T01. None of the piglets from treatment group T02 had abnormal temperature values.

PBS, and 1× with PMEM media containing 20 g/ml geneticin and 1 μg/ml TPCK trypsin (equivalent to 4.9 USP units/ml). A total of three T-25 flasks with a confluent monolayer of ST cells were infected for 1 hour at 37° C. in a 5% $CO_2$ incubator, with gentle swirling every 15 minutes to ensure the virus was evenly distributed to all cells. Five mls of PMEM media containing 20 μg/ml geneticin, 2 mM L-glutamine, and either 1 μg/ml TPCK typsin (equivalent to 4.9 USP units/ml), 3 μg/ml TPCK trypsin (equivalent to 14.6 USP units/ml), or 5 μg/ml TPCK trypsin (equivalent to 24.5 USP units/ml) was added to virus-treated flasks. Flasks were allowed to incubate for 3 days, with sampling occurring each day. After 3 days, flasks were frozen at −80° C., then thawed at 37° C., and the flask contents were placed in a 15 ml conical tube and centrifuged to remove cellular debris. The supernatant was collected, and this virus-containing material

TABLE 3 clinical sign ever present: frequency distributions by treatment

| Treatment | Ever present | General physical condition and dehydration | Temperature | Weight loss | Depression | Appetite | Digestive | Traumatisms and locomotors disorders | Respiratory | Other |
|---|---|---|---|---|---|---|---|---|---|---|
| T01 | No | 33.3 | 90.5 | 57.1 | 33.3 | 85.7 | 9.5 | 85.7 | 95.2 | 76.2 |
|  | Yes | 66.7 | 9.5 | 42.9 | 66.7 | 14.3 | 90.5 | 14.3 | 4.8 | 23.8 |
| T02 | No | 96.8 | 100.0 | 93.5 | 90.3 | 100.0 | 51.6 | 96.8 | 100.0 | 96.8 |
|  | Yes | 3.2 | 0.0 | 6.5 | 9.7 | 0.0 | 48.4 | 3.2 | 0.0 | 3.2 |

In summary, the clinical data results from this study indicate that the PEDV inactivated vaccine containing a US PEDV isolate as an antigen, is able to confer at least partial cross-protection to piglets born from vaccinated sows, in front of the challenge with an heterologous new PEDV Spanish isolate, Calf14. Therefore, results suggest the suitability of the PEDV Vaccine, Killed Virus, manufactured by Zoetis, containing a US PEDV isolate as an antigen, to reduce the impact of an outbreak produced by a new EU PEDV isolate Example 8: Isolation, Propagation, and Inoculation of CDCD Pigs with PDCoV USA/Indiana/2014/8501010 and NVSL PDCoV USA/Michigan/8977/2014

Approximately 1 $cm^3$ of tissue was used for extraction of PDCoV virus. The tissue was chopped into fine pieces using a sterile scalpel and scissors in a sterile Petri dish. Work was done in a Bio-safety cabinet to ensure aseptic conditions. Two ml of sterile PBS was added to the Petri dish to collect tissue and material was transferred to a 15 ml conical tube. Tissue was homogenized with a Qiagen TissueRuptor at 80% of maximum by pulsing for a total of 30 seconds. Homogenization was performed in an ice bucket to lessen the effect of heat on the PDCoV virus. The homogenized material was filtered through a 0.45 μM filter and 60 μl of material was used for RNA isolation and PDCoV qPCR to confirm the presence of the PDCoV virus. The filtered material containing PDCoV virus was further diluted 1:2 in sterile PBS, and then filtered through a 0.20 μM filter.

The sterile-filtered PDCoV homogenate was used to infect confluent monolayers of Swine Testicle (ST) cells by transferring 1 ml of filtered material to a T-25 flask containing 2.8×$10^6$ cells, planted 4 days prior to infection. The T-25 flasks of confluent ST cells were washed 2× with sterile is considered as Passage 1 of the virus, PDCoV USA/Indiana/2014/8501010. One ml of the total volume from the all 3 flasks was then used for Passage 2 of the virus onto three separate T-25 flasks of confluent ST cells. One ml of Passage 1 PDCoV material was used to infect a T-25 flask containing 2.8×$10^6$ cells seeded 3 to 4 days prior. Cells were first washed 2× with sterile PBS, and 1× with PMEM media containing 20 g/ml geneticin and 1 μg/ml TPCK trypsin (equivalent to 4.9 USP units/ml). Cells were infected for 1 hour at 37° C. in a 5% $CO_2$ incubator, with gentle swirling every 15 minutes to ensure virus was evenly distributed to cells. Five mls of PMEM media containing 20 g/ml geneticin, 2 mM L-glutamine, and either 1 μg/ml TPCK typsin (equivalent to 4.9 USP units/ml), 3 g/ml TPCK trypsin (equivalent to 14.6 USP units/ml), or 5 μg/ml TPCK trypsin (equivalent to 24.5 USP units/ml), corresponding to the initial trypsin concentration at infection that was added to virus-treated flasks. This procedure was repeated out to Passage 15, with the 3 g trypsin infection media sample and 12 mls of PDCoV USA/Indiana/2014/8501010 at each passage being retained.

Passage 1 material that was sampled daily was used in a PDCoV M gene-based RT-qPCR assay to monitor growth of the virus with the following primers: Forward Primer: 5'-ATCGACCACATGGCTCCAA-3' (SEQ ID NO:8); Reverse Primer: 5'-CAGCTCTTGCCCATGTAGCTT-3' (SEQ ID NO:9); and Probe: 5'/56FAM/-CACACCAGTCGTTAAGCATGGCAAGCT/3BHQ_1/3' (see SEQ ID NO:10). Briefly, 140 μl of each time-point sample virus was used for RNA isolation. Five microliters of extracted RNA was then subjected to RT-qPCR to determine final cycle threshold (Ct) value and copy number of each sample. At day 0, all three infected flasks had a Ct value of between 22 and 23, which corresponds to between 2.34×$10^5$ and 3.24×$10^5$ copies per sample. Each day sampled thereafter results in a decrease in Ct value, which correlates to an increase in viral copy number for each sample, indicating replication and growth of the virus. Summarized in Table 4 are the Ct value and corresponding copy number data for the virus.

TABLE 4

Growth Monitoring of PDCoV USA/Indiana/2014/8501010

| | Cycle Threshold (Ct) Value | | | | Copy Number/5 ul Value | | |
|---|---|---|---|---|---|---|---|
| Day | 1 μg trypsin | 3 μg trypsin | 5 μg trypsin | Day | 1 μg trypsin | 3 μg trypsin | 5 μg trypsin |
| 0 | 23.13 | 22.67 | 22.81 | 0 | 2.32E+05 | 3.47E+05 | 3.24E+05 |
| 1 | 18.34 | 17.97 | 17.50 | 1 | 6.88E+06 | 1.01E+07 | 1.13E+07 |
| 2 | 18.73 | 18.05 | 17.55 | 2 | 4.83E+06 | 8.64E+06 | 1.22E+07 |
| 3 | 18.37 | 17.85 | 17.55 | 3 | 5.38E+06 | 1.19E+07 | 6.3E+07 |

Plastic flasks or roller bottles were used for growing and expanding ST cell cultures. Plastic flasks, roller bottles, and bioreactors were used for PDCoV virus propagation. Cells were washed to remove serum prior to inoculation with virus. The virus was diluted in PMEM media containing 20 g/ml geneticin, 2 mM L-glutamine, and 1 μg/ml TPCK typsin (equivalent to 4.9 USP units/ml), and added directly to the cell monolayer. When bioreactors were used for virus propagation, trypsinized cells were transferred from the roller bottles, and a final cell passage grown in uninoculated cell growth medium was used to seed the bioreactor. Microcarriers for the bioreactors were prepared and added to the ST cells in the bioreactor. The seed virus was diluted to an appropriate volume within a multiplicity of infection (MOI) range of 0.0001 to 10.0. Growth of virus was monitored by visualizing CPE of virus infected cells and by RT-qPCR. The NVSL virus strain, PDCoV USA/Michigan/8977/2014 (see SEQ ID NO:12 for corresponding encoding DNA), was passaged to Passage 22.

The PDCoV virus causes observable cytopathic effect (CPE). Virus was harvested when viral-induced CPE reached 50-100% and infected cells began sloughing off into the medium (cell monolayer loss exceeding 50%). The roller bottle vessels were removed from the incubator, and inspected microscopically for both CPE and evidence of microbial contamination. Following the examination, the antigen fluid was harvested into appropriate sterile containers in an aseptic manner. Bioreactor fluids were examined microscopically for evidence of microbial contamination, and for the presence of desired cytopathic effects (CPE).

Following examination, the viral fluids were passed through a:100 micron filter or stainless steel mesh screen to remove microcarriers, and harvested into appropriate sterile containers in an aseptic manner. Fluids were stored at 2° C.-7° C. for a maximum of 24 hours until inactivation.

In separate tests, (1) original intestinal homogenate (source of PDCoV USA/Indiana/2014/8501010); (2) Passage 4 of strain PDCoV USA/Indiana/2014/8501010 (see SEQ ID NO:11 for corresponding encoding DNA), and (3) Passage 10 of strain PDCoV USA/Michigan/8977/2014 (see SEQ ID NO:12 for corresponding encoding DNA), were injected into 3 day old CDCD (Caesarian-derived, colostrum deprived) pigs to expand the virus material, and PDCoV virulence in pigs was assessed by monitoring clinical signs (diarrhea and vomiting), histopathology, and RT-qPCR of fecal material. Pigs were placed in assigned pens in a BSL-2 facility, with each treatment group being housed in a separate room to avoid cross-contamination. The peak clinical signs and fecal shedding appeared between 16-24 hours for the PDCoV USA/Indiana/2014/8501010 strain (see SEQ ID NO:11), and at 3 days post-inoculation for the PDCoV USA/Michigan/8977/2014 strain (see SEQ ID NO:12).

In addition to being a useful killed vaccine, it should be noted that passage 10 of PDCoV USA/Michigan/8977/2014 is sufficiently attenuated as to define the approximate minimum threshold of a passaged isolate that could be recommended for a live vaccine, although a higher number of passages would be preferred.

Example 9: Preparation and Testing of a Vaccine Based on Porcine Deltacoronavirus Isolate PDCoV USA/Michigan/8977/2014

Harvested PDCoV antigen was concentrated 20×prior to inactivation with a 5 mM binary ethylenimine (BEI) solution. The mixture is cyclized for 60-80 minutes at 36±2° C. Following the addition of inactivant, the antigen was thoroughly mixed and transferred to an inactivation vessel for the duration of the process (≥48 hours, with agitation). Neutralization of the inactivated antigen fluids was facilitated through the addition of sterile 1 M Sodium Thiosulfate, to a final concentration of approximately 20-25 mM. Post-inactivated/neutralized antigen production fluids were tested for sterility and completeness of inactivation, and stored at 2-7° C. for future use in vaccine serial formulation.

A vaccine containing the following components was formulated: 7.42 $\log_{10}TCID_{50}$ of PDCoV USA/Michigan/8977/2014 (see SEQ ID NO:12) virus per 2 ml dose; 5% (v/v) Rehydragel® LV; 25% (v/v) of "20% Amphigen" (i.e. it is further 4-fold diluted); and 0.01% (w/v) of merthiolate.

Killed PDCoV USA/Michigan/8977/2014 virus was also adjuvanted with TXO, and used for vaccination. TXO provided the following components per 1 ml dose of vaccine: 50 ug "CpG 23877" (see SEQ ID NO: 8 as listed in the WO2015/042369 publication), 10 mg DEAE-Dextran, DRAKEOL 6VR (45% w/v), Span-80 (6.3% v/v), Tween-80 (1.45% v/v) and 10 mM PBS.

As is understood in the art, the order of addition of components can be varied to provide the equivalent final vaccine composition. For example, an appropriate dilution of killed virus in buffer can be prepared. An appropriate amount of Rehydragel® LV (about 2% aluminum hydroxide content) stock solution can then be added, with blending, in order to permit the desired 5% (v/v) concentration of Rehydragel® LV in the actual final product. Once prepared, this intermediate stock material is combined with an appropriate amount of "20% Amphigen" stock (as generally described above, and already containing necessary amounts of Tween 80 and Span 80) to again achieve a final product having 25% (v/v) of "20% Amphigen". An appropriate amount of 10% merthiolate can finally be added.

The vaccinate compositions of the invention permit variation in all of the ingredients, such that the total dose of antigen may be varied preferably by a factor of 100 (up or down) compared to the antigen dose stated above, and most preferably by a factor of 10 or less (up or down). Similarly, surfactant concentrations (whether Tween or Span) may be varied by up to a factor of 10, independently of each other, or they may be deleted entirely, with replacement by appropriate concentrations of similar materials, as is well understood in the art.

Porcine serum generated from the pigs vaccinated with inactivated PDCoV adjuvanted with Amphigen®/Rehydragel® LV or TXO were tested in a serum neutralization (SN) assay as follows: Porcine serum from each treatment group was pooled and heat inactivated at 56° C. for 30 minutes. Serum samples were diluted 2-fold by mixing 500 μl of the serum with 500 µl PMEM media supplemented with 20 g/ml geneticin, 2 mM L-glutamine and 1 µg/ml TPCK typsin (equivalent to 4.9 USP units/ml). PDCoV live virus at dilutions ranging from $\log_{10}TCID_{50}=5.0$ to $\log_{10}TCID_{50}=2.0$ were added to the diluted serum and incubated for 1 hour at room temperature. The serum/virus mixture was inoculated onto 96-well plates seeded with confluent ST cells, and incubated for 4 days at 37° C. and 5% $CO_2$ The plates were then fixed with 80% acetone in a water mixture for 15 minutes. The mixture was then removed, and plates were air-dried for 15 minutes to remove the remaining acetone. Plates were stained with rabbit anti-PDCoV S1 serum primary antibody, and goat anti-rabbit Alexa Fluor® 488-labelled secondary antibody (Jackson ImmunoResearch), prior to reading plates on a fluorescent microscope. The serum neutralization titer was calculated by determining the lowest dilution of serum where PDCoV growth was 100% inhibited, and applying the Spearman-Karber method to calculate titer values.

It was determined that the serum from pigs vaccinated with inactivated PDCoV adjuvanted with either Amphigen®/Rehydragel® LV, or TXO, successfully neutralized the growth of PDCoV virus on ST cells at all virus inoculum concentrations tested. In general, the group vaccinated with inactivated PDCoV/TXO adjuvant gave higher SN titers (see Table 5) than the Amphigen®/Rehydragel® LV-adjuvanted group.

either with 5% (v/v) Rehydragel® LV and 25% (v/v) of "20% Amphigen", or with TXO adjuvant, and injected into pigs to generate a humoral immune response through the production of antibodies to the S1 protein.

Porcine serum generated from the pigs vaccinated with PDCoV S1 protein adjuvanted with Amphigen®/Rehydragel® LV or with TXO were tested in a serum neutralization (SN) assay as follows:

Porcine serum from each treatment group was pooled, and heat inactivated at 56° C. for 30 minutes. Serum samples were diluted 2-fold by mixing 500 µl of the serum with 500 µl PMEM media, supplemented with 20 g/ml geneticin, 2 mM L-glutamine, and 1 g/ml TPCK typsin (equivalent to 14.6 USP units/ml). PDCoV virus at dilutions ranging from $\log_{10}TCID_{50}=5.0$ to $\log_{10}TCID_{50}=2.0$ were added to the diluted serum, and incubated for 1 hour at room temperature. The serum/virus mixture was inoculated onto 96-well plates seeded with confluent ST cells, and incubated for 4 days at 37° C. and 5% $CO_2$ The plates were then fixed with 80% acetone in water mixture for 15 minutes, after which the mixture was removed, and plates were air-dried for 15 minutes to remove the remaining acetone. Plates were stained with rabbit anti-PDCoV S1 serum primary antibody, and goat anti-rabbit Alexa Fluor-labelled secondary antibody, prior to reading plates on a fluorescent microscope.

TABLE 5

Serum Neutralising (SN) Titers of Inactivated PDCoV Vaccinated Pigs

| | PDCoV Virus Titer | | | |
| --- | --- | --- | --- | --- |
| Vaccine Treatment | $\log_{10}TCID_{50}=$ 5...0 | $\log_{10}TCID_{50}=$ 4...0 | $\log_{10}TCID_{50}=$ 3...0 | $\log_{10}TCID_{50}=$ 2...0 |
| Saline | <2 | <2 | <2 | <2 |
| PDCoV + Amphigen/Rehydragel | 128 | 128 | 256 | 384 |
| PDCoV + TXO | 256 | 384 | 512 | 1024 |

Example 10: Cloning, Expression, and Inoculation of Pigs with S1 Protein; Expression of N Protein The complete genome sequence of Porcine Deltacoronavirus isolate USA/IA/2014/8734 has been published and deposited in GenBank under the accession number KJ567050. From that sequence, a synthetic S1 gene with a 3' His-tag was generated, and cloned into a proprietary mammalian expression vector. The S1 protein was expressed in Human Embryonic Kidney (HEK) cells, and purified by immobilized metal affinity chromatograpy (IMAC). A 40 µg dose of purified S1 protein was adjuvanted The serum neutralization titer was calculated by determining the lowest dilution of serum where PDCoV growth was inhibited and applying the Spearman-Karber method to calculate titer values.

It was determined that the serum from pigs vaccinated with PDCoV S1 protein advuanted with either Amphigen®/Rehydragel® LV or TXO successfully neutralized the growth of PDCoV virus on ST cells at all virus inoculum concentrations tested. In general, the group vaccinated with PDCoV S1 protein adjuvanted with TXO gave higher SN titers (see Table 6) than the Amphigen®/Rehydragel® LV-adjuvanted group.

TABLE 6

Serum Neutralising (SN) Titers of PDCoV S1 Vaccinated Pigs

| | PDCoV Virus Titer | | | |
| --- | --- | --- | --- | --- |
| Vaccine Treatment | $\log_{10}TCID_{50}=$ 5.0 | $\log_{10}TCID_{50}=$ 4.0 | $\log_{10}TCID_{50}=$ 3.0 | $\log_{10}TCID_{50}=$ 2.0 |
| Saline | <2 | <2 | <2 | <2 |
| PDCoV S1 + Amphigen/Rehydragel | 24 | 32 | 64 | 192 |
| PDCoV S1 + TXO | 128 | 192 | 384 | 536 |

The nucleocapsid (N) nucleotide sequence from PDCoV isolate USA/IA/2014/8734 was used to make a synthetic gene for cloning and expression of the N protein in both a pET100 vector, and a proprietary heat-inducible bacterial expression vector. The pET100 vector contains a 6×His tag for detection and purification of the expressed protein. Both constructs were transformed into E. coli, and expressed by induction with either 1 mM IPTG (pET100) or heat (heat-inducible vector). The bacterial expression resulted in an ~51 kDa protein being expressed. This resulting protein will be purified and used as a reagent for antibody generation.

Example 11: Efficacy of Monovalent PDCoV Vaccine and Bivalent (PDCoV+PEDV)Vaccine In order to assess the efficacy in pregnant sows of a monovalent inactivated PDCoV vaccine, as well as a bivalent inactivated PDCoV/PEDV vaccine, the following experiments are carried out. PDCoV strain USA/Michigan/8977/2014 (see SEQ ID NO:12) is cultured, and vaccines prepared as described previously. A bivalent vaccine containing PEDV strain USA/Colorado/2013 (see SEQ ID NO:7) and PDCoV strain USA/Michigan/8977/2014 is also prepared. The vaccines are given intramuscularly to pregnant sows as two doses, 2 ML each, three weeks apart, at five and two weeks pre-farrowing.

Pregnant sows are included in the study. At 5 weeks before farrowing, a dose of each inactivated vaccine is administered to sows by the IM route; 1 or more sows remain unvaccinated (controls). Three weeks later, vaccinated sows receive a second dose. After farrowing, approximately at 0-5 days of age, all piglets are challenged with either the Spanish PEDV strain Calaf14 (see SEQ ID NO: 1 for S-protein encoding sequence), or the PDCoV strain USA/Indiana/2014/8501010 (see SEQ ID NO:11). Twice daily after challenge, all piglets are evaluated for the presence of clinical signs (including diarrhea); rectal temperatures are taken; body weights are measured; and fecal swabs are taken, to perform either a PEDV-specific or PDCoV-specific RT-qPCR assay. At day 3 to 7 after challenge, all piglets are euthanized and necropsied; gut tissue samples are also removed.

The invention claimed is:

1. A vaccine composition comprising inactivated porcine epidemic diarrhea virus (PEDV), adjuvanted as an oil-in-water emulsion, wherein the adjuvant components include de-oiled lecithin dissolved in a light mineral oil and aluminum hydroxide, wherein said vaccine, upon administration to a swine, elicits production of neutralizing antibodies in the swine.

2. The vaccine composition of claim 1 wherein the inactivated PEDV is strain USA/Colorado/2013, whose genomic sequence is deposited in GenBank as accession No. KF272920 and whose genomic sequence comprises SEQ ID NO: 7.

3. The vaccine composition of claim 1 wherein the final concentration of 20% de-oiled lecithin dissolved in a light mineral oil is 25% (v/v).

4. The vaccine composition of claim 1 further comprising inactivated porcine deltacoronavirus (PDCoV).

5. The vaccine composition of claim 4 wherein the PDCOV is selected from the group consisting of USA/Michigan/8977/2014, whose sequence is deposited as GenBank accession No. KM012168 and whose genomic sequence comprises SEQ ID NO:12, and strain USA/Indiana/2014/8501010, whose genome sequence comprises SEQ ID NO: 11.

6. The vaccine composition of claim 4 wherein the final concentration of 20% de-oiled lecithin dissolved in a light mineral oil is 25% (v/v).

* * * * *